US006448293B1

(12) United States Patent
Andrews et al.

(10) Patent No.: US 6,448,293 B1
(45) Date of Patent: Sep. 10, 2002

(54) DIPHENYL ETHER COMPOUNDS USEFUL IN THERAPY

(75) Inventors: Mark David Andrews; David Hepworth; Donald Stuart Middleton; Alan Stobie, all of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/810,378

(22) Filed: Mar. 16, 2001

Related U.S. Application Data

(60) Provisional application No. 60/197,127, filed on Apr. 14, 2000.

(30) Foreign Application Priority Data

Mar. 31, 2000 (GB) .............................................. 0007884

(51) Int. Cl.[7] ........................ C07C 217/58; A61K 31/35
(52) U.S. Cl. ........................ 514/603; 514/603; 514/655; 548/255; 548/267.2; 548/375.1; 558/422; 564/85; 564/86; 564/162; 564/390
(58) Field of Search ........................... 564/390, 85, 86, 564/162; 514/655, 603; 558/422; 548/255, 267.2, 375.1

(56) References Cited

U.S. PATENT DOCUMENTS

| | | | |
|---|---|---|---|
| 4,161,529 A | 7/1979 | Beregi et al. | |
| 5,190,965 A | 3/1993 | Ruigt et al. | |
| 5,334,748 A | 8/1994 | Buckley et al. | |
| 5,430,063 A | 7/1995 | Ruigt et al. | |

FOREIGN PATENT DOCUMENTS

| | | |
|---|---|---|
| EP | 0394043 | 4/1990 |
| EP | 0402097 | 6/1990 |
| EP | 0415613 | 8/1990 |
| EP | 0516234 | 5/1992 |
| WO | 9623783 | 8/1996 |
| WO | 9637204 | 11/1996 |
| WO | 9717325 | 5/1997 |
| WO | 0050380 | 8/2000 |
| WO | 0127068 | 4/2001 |

OTHER PUBLICATIONS

R.H.F. Manske, et al.—"Synthesis & Reactions of some Dibenzoxepins" Journ. Am. Chem Soc. vol. 72, #10, Oct. 16, 1950, pp. 4797–4799.

T. Kametani, et al.—"The Conformation & Rearrangement Reaction of Derivatives of 10, 11 Dihydrodibenzopin" Journ. The Chem Soc.—Sec. C: Organ. Chem., Nov. 23, 1968, pp. 2877–2883.

G.W. Yeager, et al.—"Umpoled Synthon Approach to the Synthesis of 2–Aryloxphenols", Synthesis, Nov. 1, 1995, pp. 28–30.

Primary Examiner—Robert Gerstl
(74) Attorney, Agent, or Firm—Peter C. Richardson; Paul H. Ginsburg; Jolene W. Appleman

(57) ABSTRACT

A compound of general formula (I), or pharmaceutically acceptable salts, solvates or polymorphs thereof; wherein; $R^1$ and $R^2$, which may be the same or different, are hydrogen, $C_1$–$C_6$alkyl, $(CH_2)_m$ $(C_3$–$C_6$cycloalkyl) wherein m =0, 1, 2 or 3, or $R^1$ and $R^2$ together with the nitrogen to which they are attached form an azetidine ring; each $R^3$ is independently $CF_3$, $OCF_3$, $C_{1-4}$alkylthio or $C_1$–$C_4$alkoxy; n is 1, 2 or 3; and $R^4$ and $R^5$, which may be the same or different, are: A—X, wherein A =—CH=CH— or —$(CH_2)$p— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, S(O)$R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$ alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F, OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and O, optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)$_2$; wherein when $R^1$ and $R^2$ are methyl, $R^4$ and $R^5$ are hydrogen and n is 1, $R^3$is not a —SMe group para to the ether linkage linking rings A and B.

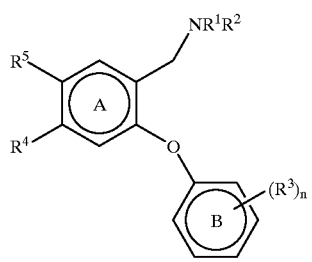

(1)

28 Claims, No Drawings

DIPHENYL ETHER COMPOUNDS USEFUL IN THERAPY

This application claims priority under 35 U.S.C. §119 (a–e) from Great Britain Application No. 0007884.0, filed Mar. 31, 2000 and United States Provisional Application Ser. No. 60/197,127 filed Apr. 14, 2000, which applications are hereby incorporated by reference.

This invention relates to a series of novel diphenyl ether compounds which inhibit monoamine re-uptake. In particular compounds of the present invention exhibit activity as selective serotonin re-uptake inhibitors (SSRIs) and have utility therefore in a variety of therapeutic areas. More notably the compounds of the present invention are useful in the treatment or prevention of a variety of disorders, including those in which the regulation of monoamine transporter function is implicated, such as depression, attention deficit hyperactivity disorder, obsessive-compulsive disorder, post-traumatic stress disorder, substance abuse disorders and sexual dysfunction including premature ejaculation, and to pharmaceutical formulations containing such compounds.

According to a first aspect, the invention provides a compound of general formula (I), or pharmaceutically acceptable salts, solvates or polymorphs thereof;

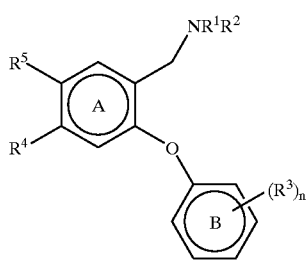

(1)

wherein;

$R^1$ and $R^2$, which may be the same or different, are hydrogen, $C_1$–$C_6$alkyl, $(CH_2)_m(C_3$–$C_6$cycloalkyl) wherein m=0, 1, 2 or 3, or $R^1$ and $R^2$ together with the nitrogen to which they are attached form an azetidine ring;

each $R^3$ is independently $CF_3$, $OCF_3$, $C_{1-4}$alkylthio or $C_1$–$C_4$alkoxy;

n is 1, 2 or 3; and $R^4$ and $R^5$, which may be the same or different, are:

A—X, wherein A=—CH=CH— or —(CH$_2$)$_p$— where p is 0, 1 or 2; X is hydrogen, F, Cl, Br, I, CONR$^6$R$^7$, SO$_2$NR$^6$R$^7$, SO$_2$NHC(=O)R$^6$, OH, C$_{1-4}$alkoxy, NR$^8$SO$_2$R$^9$, NO$_2$, NR$^6$R$^{11}$, CN, CO$_2$R$^{10}$, CHO, SR$^{10}$, S(O)R$^9$ or SO$_2$R$^{10}$; R$^6$, R$^7$, R$^8$ and R$^{10}$ which may be the same or different, are hydrogen or C$_{1-6}$alkyl optionally substituted independently by one or more R$^{12}$; R$^9$ is C$_{1-6}$ alkyl optionally substituted independently by one or more R$^{12}$; R$^{11}$ is hydrogen, C$_{1-6}$ alkyl optionally substituted independently by one or more R$^{12}$, C(O)R$^6$, CO$_2$R$^9$, C(O)NHR$^6$ or SO$_2$NR$^6$R$^7$; R$^{12}$ is F (preferably up to 3), OH, CO$_2$H, C$_{3-6}$cycloalkyl, NH$_2$, CONH$_2$, C$_{1-6}$alkoxy, C$_{1-6}$alkoxycarbonyl or a 5- or 6-membered heterocyclic ring containing 1, 2 or 3 heteroatoms selected from N, S and O optionally substituted independently by one or more R$^{13}$; or R$^6$ and R$^7$, together with the nitrogen to which they are attached, form a 4-, 5- or 6-membered heterocyclic ring optionally substituted independently by one or more R$^{13}$; or a 5- or 6-membered heterocyclic ring containing 1, 2 or 3 heteroatoms selected from N, S and O optionally substituted independently by one or more R$^{13}$;

wherein R$^{13}$ is hydroxy, C$_1$–C$_4$alkoxy, F, C$_1$–C$_6$alkyl, haloalkyl, haloalkoxy, —NH$_2$, —NH(C$_1$–C$_6$alkyl) or —N(C$_1$–C$_6$alkyl)$_2$; and wherein when R$^1$ and R$^2$ are methyl, R$^4$ and R$^5$ are hydrogen and n is 1, R$^3$ is not a —SMe group para to the ether linkage linking rings A and B.

Unless otherwise indicated, any alkyl group may be straight or branched and is of 1 to 6 carbon atoms, preferably 1 to 4 and particularly 1 to 3 carbon atoms.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Preferably R$^1$ and R$^2$, which may be the same or different, are hydrogen or C$_1$–C$_6$alkyl. More preferably hydrogen or methyl.

Preferably each R$^3$ is independently —CF$_3$, —OCF$_3$, methylthio, ethylthio or methoxy.

Preferably at least one R$^3$ is para to the ether linkage linking ring A and B.

Preferably at least one R$^3$ is methylthio.

Preferably R$^4$ and R$^5$, which may be the same or different, are —(CH$_2$)$_p$—X, where p is 0, 1 or 2 (preferably 0 or 1); X is hydrogen, hydroxy, CONR$^6$R$^7$, SO$_2$NR$^6$R$^7$, NR$^8$SO$_2$R$^9$, SR$^{10}$, SOR$^9$ or SO$_2$R$^{10}$ wherein R$^6$, R$^7$, R$^8$, R$^9$ and R$^{10}$ are as defined in the first aspect, or a 5- or 6-membered heterocyclic ring containing 1, 2 or 3 heteroatoms selected from N, S and O (preferably oxadiazolyl, triazolyl, imidazolyl, oxazolyl, pyrazolyl, pyridinyl or pyrimidinyl).

More preferably R$^4$ and R$^5$, which may be the same or different, are: —(CH$_2$)$_p$—X, where p is 0 or 1; X is hydrogen, hydroxy, CONR$^6$R$^7$, SO$_2$NR$^6$R$^7$ or NR$^8$SO$_2$R$^9$; wherein R$^6$ and R$^7$, which may be the same or different, are hydrogen or C$_1$–C$_3$alkyl optionally substituted by hydroxy, —CONH$_2$ or C$_1$–C$_3$alkoxy (preferably methoxy); R$^8$ is hydrogen, hydroxyethyl or methyl; or R$^9$ is methyl, ethyl, isopropyl, trifluoromethyl or methoxyethyl; or triazolyl, imidazolyl or pyrazolyl.

More preferably still R$^4$ and R$^5$ are not both hydrogen. More preferably still R$^4$ is hydrogen.

Preferably R$^6$ and R$^7$, which may be the same or different, are hydrogen, C$_1$–C$_3$alkyl optionally substituted by hydroxy, —CONH$_2$ or C$_1$–C$_3$alkoxy (preferably methoxy). More preferably R$^6$ and R$^7$, which may be the same or different, are hydrogen or methyl, more preferably still hydrogen.

When present, R$^{12}$ is preferably oxadiazolyl, triazolyl, imidazolyl, oxazolyl, pyrazolyl, pyridinyl or pyrimidinyl. More preferably triazolyl, imidazolyl or pyrazolyl.

In the case where R$^6$ and R$^7$, together with the nitrogen to which they are attached, form a heterocyclic ring, preferred rings are pyrrolidine or piperidine rings each of which may be substituted by OH or $CONH_2$ or a morpholine ring which may be substituted by $CONH_2$.

Preferably $R^{11}$ is hydrogen or $C_{1-6}$ alkyl.

Preferably $R^8$ is hydrogen, hydroxyethyl or methyl. More preferably hydrogen.

Preferably $R^9$ is methyl, ethyl, isopropyl, trifluoromethyl or methoxyethyl. More preferably methyl or ethyl (preferably methyl).

Preferably $R^{10}$ is methyl or ethyl.

Preferably p is 1 or 0, more preferably 0.

Preferably $R^1$ and $R^2$, which may be the same or different, are hydrogen or methyl; at least one $R^3$ is para to the ether linkage and is $CF_3$, $OCF_3$, methylthio, ethylthio or methoxy; and $R^4$ and $R^5$, which may be the same or different, are $(CH_2)_p$—X, where p is 0 or 1; X is hydrogen, hydroxy, $CONR^6R^7$, $SO_2NR^6R^7$, $NR^8SO_2R^9$, $SR^{10}$, $SOR^9$ or $SO_2R^{10}$ and wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); or $R^6$ and $R^7$, together with the nitrogen to which they are attached, may form a morpholine, pyrrolidine or piperidine ring each of which may be substituted by OH or $CONH_2$; $R^8$ is hydrogen, hydroxyethyl or methyl (preferably hydrogen); $R^9$ is methyl, ethyl, isopropyl, trifluoromethyl or methoxyethyl; and $R^{10}$ is methyl or ethyl; or an oxadiazolyl, triazolyl, imidazolyl, oxazolyl, pyrazolyl, pyridinyl or pyrimidinyl group.

More preferably $R^1$ and $R^2$, which may be the same or different, are hydrogen or methyl; at least one $R^3$ is para to the ether linkage and is $CF_3$, $OCF_3$, methylthio, ethylthio or methoxy, and at least one $R^3$ is methylthio or ethylthio; and $R^4$ and $R^5$, which may be the same or different, are —$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); $R^8$ is hydrogen, hydroxyethyl or methyl; $R^9$ is methyl, ethyl, isopropyl, trifluoromethyl or methoxyethyl; or triazolyl, imidazolyl or pyrazolyl.

More preferably still $R^1$ and $R^2$, which may be the same or different, are hydrogen or methyl; at least one $R^3$ is para to the ether linkage and is $CF_3$, $OCF_3$, methylthio or methoxy, and at least one $R^3$ is methylthio;

$R^4$ is hydrogen, and $R^5$ is —$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); $R^8$ is hydrogen, hydroxyethyl or methyl; $R^9$ is methyl, ethyl, isopropyl, trifluoromethyl or methoxyethyl; or triazolyl, imidazolyl or pyrazolyl.

More preferably still $R^4$ and $R^5$ are not both hydrogen.

For the avoidance of doubt, unless otherwise indicated, the term substituted means substituted by one or more defined groups. In the case where groups may be selected from a number of alternatives groups, the selected groups may be the same or different.

For the avoidance of doubt, the term independently means that where more than one substituent is selected from a number of possible substituents, those substituents may be the same or different.

Preferred compounds of formula (I) include:

3-[(dimethylamino)methyl]-4-[4-(methylsulfanyl)phenoxy]benzenesulfonamide;

3-[(dimethylamino)methyl]-N-methyl-4-[4-(trifluoromethyl)phenoxy]benzenesulfonamide;

3-[(dimethylamino)methyl]-4-[4-(trifluoromethoxy)phenoxy]benzenesulfonamide;

3-[(dimethylamino)methyl]-N-[(2R)-2-hydroxypropyl]-4-[4-(methylsulfanyl)-phenoxy]benzenesulfonamide;

3-[(dimethylamino)methyl]-N-[(1S)-2-hydroxy-1-methylethyl]-4-[4-(methylsulfanyl)-phenoxy]benzenesulfonamide;

3-[(dimethylamino)methyl]-N-(2-hydroxyethyl)-4-[4-(methylsulfanyl)phenoxy]-benzenesulfonamide;

3-[(dimethylamino)methyl]-4-[4-(methylsulfanyl)phenoxy]benzonitrile;

3-[(dimethylamino)methyl]-4-[4-(methylsulfanyl)phenoxy]benzamide;

3-[(dimethylamino)methyl]-4-[4-(trifluoromethoxy)phenoxy]benzamide;

3-[(methylamino)methyl]-4-[4-(methylsulfanyl)phenoxy]benzamide;

N-{3-[(dimethylamino)methyl]-4-[4-(trifluoromethyl)phenoxy]phenyl}-methanesulfonamide;

4-[3-methoxy-4-(methylsulfanyl)phenoxy]-3-[(methylamino)methyl]benzamide;

N-methyl-3-[(methylamino)methyl]-4-[4-(methylsulfanyl)phenoxy]benzamide;

3-[(dimethylamino)methyl]-4-[3-methoxy-4-(methylsulfanyl)phenoxy]-benzamide;

N-methyl-N-[2-[4-(methylsulfanyl)phenoxy]-5-(1H-1,2,3-triazol-1-yl)benzyl]amine;

N-methyl-N-[2-[4-(methylsulfanyl)phenoxy]-5-(1H-1,2,4-triazol-1-yl)benzyl]amine;

N,N-dimethyl-N-[2-[4-(methylsulfanyl)phenoxy]-5-(1H-1,2,4-triazol-1-yl)benzyl]-amine;

N-[2-[4-(methylsulfanyl)phenoxy]-5-(4H-1,2,4-triazol-4-yl)benzyl]-N,N-dimethylamine; and N-{5-(3-amino-1H-pyrazol-1-yl)-2-[4-(methylsulfanyl)phenoxy]benzyl}-N-methylamine.

The compounds of the invention have the advantage that they are selective inhibitors of the re-uptake of serotonin (SRIs) (and so are likely to have reduced side effects), they have a rapid onset of action (making them suitable for administration shortly before an effect is required), they have desirable potency and associated properties. Compounds that selectively inhibit the re-uptake of serotonin, but not noradrenaline or dopamine, are preferred.

We have found that compounds of formula I which possess these properties have a relatively polar group at $R^4/R^5$. Therefore according to a further aspect, the invention provides a compound of general formula I and pharmaceutically acceptable salts thereof, wherein $R^1$, $R^2$, $R^3$ and n are as defined in the first aspect; and $R^4$ and $R^5$, which may be the same or different, are —$(CH_2)_p$—A', wherein p is 0, 1 or 2 and A' is a polar group. In this aspect, polar groups may be defined as those having a negative π-value (see C Hansch and A Leo, 'Substituent Constants for Correlation Analysis in Chemistry and Biology', Wiley, N.Y., 1979). In this system, H has a π-value of 0.00, —$OCH_3$ has a π-value of –0.02, and —$SO_2NH_2$ has a π-value of –1.82, for example [see Table VI-I, 'Well-Characterized Aromatic Substituents', p 49, ibid]. More preferred polar groups have a more negative π-value: thus, preferred groups have π-values of a greater negative value than –0.1, more preferably a greater negative value than –0.5, and most preferably a greater negative value than –1.0. Even when p is other than zero in the above definition, the definition of A' is based on the above reference as if p was zero.

The pharmaceutically or veterinarily acceptable salts of the compounds of the invention which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For reviews on suitable pharmaceutical salts see Berge et al, *J. Pharm, Sci.*, 66, 1–19, 1977; Bighley et al, *International Journal of Pharmaceutics*, 33 (1986), 201–217; and P L Gould, *Encyclopedia of Pharmaceutical Technology*, Miarcel Debker Inc, New York 1996, Volume 13, page 453–497.

The pharmaceutically acceptable solvates of the compounds of the invention include the hydrates thereof.

Also included within the scope of the compound and various salts of the invention are polymorphs thereof.

Preferred salts are the tartrate salts, particularly the L-tartrate and the D-tartrate salts (and also the racemic D/L-tartrate); the phosphate salt; the hydrochloride salt; the citrate salt; and the sulfate salt. A further preferred salt is the sodium salt (see Example 28).

Hereinafter compounds, their pharmaceutically acceptable salts, their solvates or polymorphs, defined in any aspect of the invention (except intermediate compounds in chemical processes) are referred to as "compounds of the invention".

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, (α-pyridonyl.

The invention also includes radiolabelled compounds. It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in *Drugs of Today*, Volume 19, Number 9, 1983, pp 499–538 and in *Topics in Chemistry*, Chapter 31, pp 306–316 and in *"Design of Prodrugs"* by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Preferred prodrugs for compounds of the invention include : esters, carbonate esters, hemi-esters, phosphate esters, nitro esters, sulfate esters, sulfoxides, amides, carbamates, azo-compounds, phosphamides, glycosides, ethers, acetals and ketals.

Compounds of the invention may be prepared, in known manner in a variety of ways.

In the following reaction schemes and hereafter, unless otherwise stated, $R^1$ to $R^{13}$, n, m and p are as defined in the first aspect. These processes form further aspects of the invention Throughout the specification, general formulae are designated by Roman numerals I, II, III, IV etc. Subsets of these general formulae are defined as Ia, Ib, Ic etc., . . . IVa, IVb, IVc etc.

Compounds of general formula (I) may be prepared from compounds of general formula (II) by a variety of methodologies (see Scheme 1), wherein L is a suitable leaving group such as halogen (F, Cl, Br or I) or a sulfonate ester such as trifluoromethanesulfonate or methanesulfonate, preferably L is F or Cl.

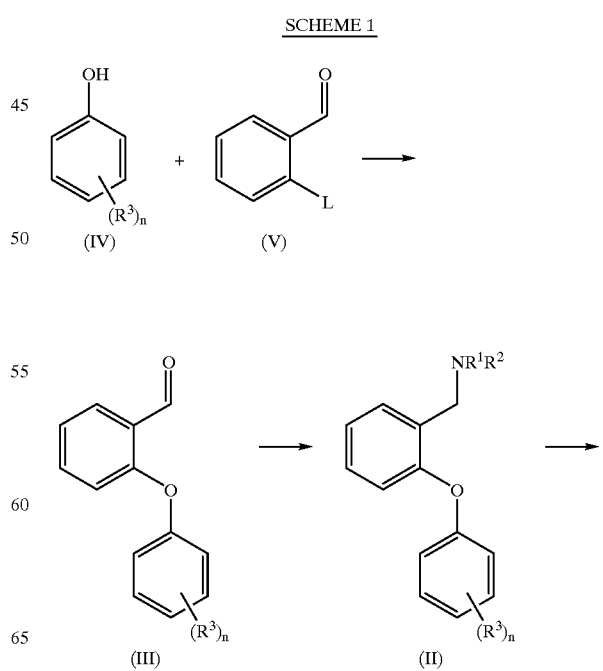

SCHEME 1

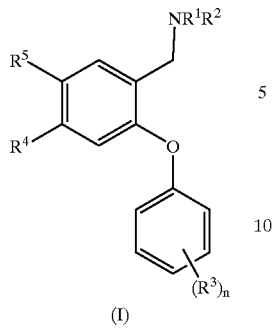

(I)

For example:

i) Where $R^4/R^5$ are halogen, by reaction of (II) with a suitable halogenating agent in an inert solvent which does not adversely affect the reaction. Suitable halogenating agents include trifluoromethanesulfonic acid and N-iodosuccinimide and suitable inert solvents include dichloromethane as illustrated in Example 16 herein;

ii) Where $R^4/R^5$ are —$NO_2$, by reaction of (II) with a suitable nitrating agent, such as an alkali metal nitrate, in an inert solvent which does not adversely affect the reaction at, or below, room temperature. Suitable nitrating agents include trifluoromethanesulfonic acid/ potassium nitrate and suitable inert solvents include trifluoroacetic acid, as illustrated in Example 21 herein; or iii) Transformation to the compounds of formula I where $R^4/R^5$ is —$SO_2NR^6R^7$ by reaction of an intermediate sulfonyl chloride with the requisite amine of formula $HNR^6R^7$ in a suitable solvent. Suitable solvents include ethanol and the reactions are generally performed at or below room temperature. For example, compounds of formula (Ia), where $R^5$ is —$SO_2NR^6R^7$, may be prepared via the intermediate sulfonyl chlorides (XII) from compounds of formula (II) by reaction of (II) with chlorosulfonic acid followed by reaction with $HNR^6R^7$. Reaction conditions typically comprise low temperature. The reaction can take place either neat, i.e. in the absence of solvent, or in the presence of an inert solvent which does not adversely affect the reaction. Suitable inert solvents include dichloromethane and a typical reaction temperature is 0° C., as illustrated in Example 28 herein. The intermediate sulfonyl chloride (XII) may be isolated, purified and then reacted with $HNR^6R^7$, alternatively it may be generated in situ, without isolation, and then reacted with $HNR^6R^7$.

SCHEME 1a

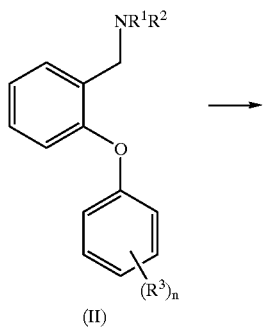

(II)

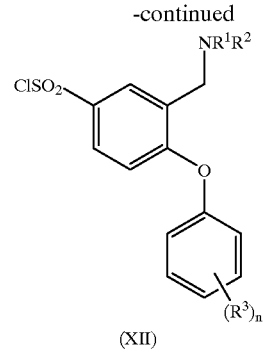

(XII)

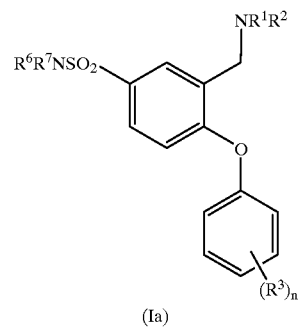

(Ia)

Thus according to a further aspect, the invention provides a process for preparing compounds of general formula (I) from compounds of the general formula (II). In a preferred embodiment, there is provided a process for preparing compounds of formula (Ia) by reacting compounds of formula (II) in a suitable solvent, with chlorosulfonic acid to give compounds of formula (XII) followed by reaction with $HNR^6R^7$ to give compounds of formula (Ia). Preferably compounds of formula (XII) are generated in situ and reacted with $HNR^6R^7$ without isolation.

Compounds of general formula (II) may in turn be prepared from compounds of formula (III) by reaction with an amine of general formula $HNR^1R^2$, or with a suitable salt form thereof, together with a hydride reducing agent in a suitable solvent. When either $R^1$ or $R^2$ is hydrogen, suitable solvents include protic solvents such as ethanol, and sodium borohydride is an appropriate reducing agent. When neither $R^1$ or $R^2$ are hydrogen, tetrahydrofuran/dichloromethane is a suitable solvent system and sodium tri(acetoxy) borohydride is a suitable reducing agent. In such reactions the use of a salt form of $HNR^1R^2$, such as the hydrochloride is preferable, and an auxiliary base, to aid solubility of the $HNR^1R^2$ salt, such as triethylamine may optionally be added.

Compounds of formula (III) may be prepared in turn from the coupling of compounds of general formula (IV) with aldehyde compounds of general formula (V). Such coupling reaction may be accomplished by techniques known in the art, such as, via reaction with potassium carbonate in a suitable solvent such as dimethylformamide under appropriate reaction conditions such as elevated temperature and in an inert atmosphere.

Alternatively, compounds of general formula (I) may be prepared from compounds of general formula (VII) (See Scheme 2) in analogous fashion to the preparation of (II) (see Scheme 1).

SCHEME 2

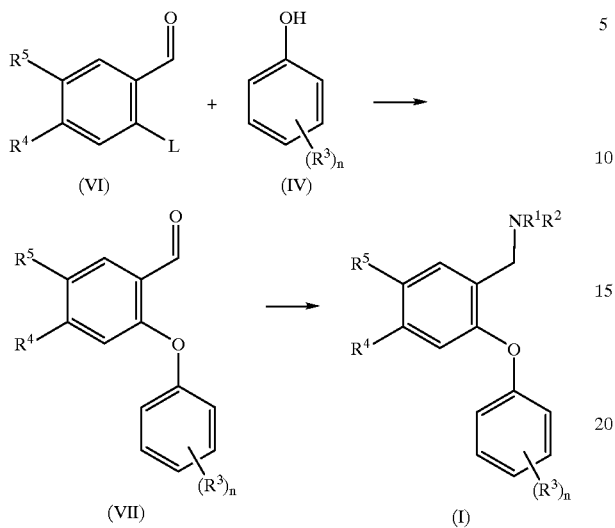

Compounds of general formula (VII) may be prepared from (VI) and (IV) in an analogous fashion to the preparation of (Ill) (see Scheme 1).

Alternatively, compounds of general formula (I) having a particular $R^4/R^5$ substituent may be converted into other compounds of formula (I) using known techniques. For example:

i) When $R^4/R^5$ is halogen such as chloro, bromo or iodo, it may be converted to cyano via reaction with a cyanide salt in the presence of a Pd(0) or (II)catalyst in a high boiling solvent at elevated temperatures. Suitable Pd catalysts include palladium tetrakis (triphenylphosphine), suitable cyanide salts include $Zn(CN)_2$ and suitable high boiling solvents which do not adversely affect the reaction include dimethylformamide as exemplified by Example 81 herein;

ii) When $R^4/R^5$ is halogen such as chloro, bromo or iodo, it may be converted to —$CH_2CN$ via an intermediate cyanoester. The intermediate cyanoesters are formed by reaction with an α-cyanoacetate in the presence of a copper(I) salt and a base, in a high boiling solvent at elevated temperatures. Suitable α-cyanoacetates include ethyl α-cyanoacetate, suitable copper(I) salts include copper(I) bromide, suitable bases include potassium carbonate and suitable high boiling solvents include dimethylsulfoxide. The intermediate cyanoesters may then be hydrolysed and decarboxylated in one step by treatment with a hydroxide salt in a high boiling solvent at elevated temperatures. Suitable hydroxide salts include sodium hydroxide and suitable high boiling solvents include aqueous dioxan, as exemplified by Example 89 herein;

iii) When $R^4/R^5$ is halogen such as chloro, bromo or iodo, it may be converted to the corresponding sulfide —SR by treatment with an alkyl thiolate salt and a Pd(0) or (II)catalyst, in an inert high boiling solvent which does not adversely affect the reaction, at elevated temperatures. Suitable alkyl thiolate salts include sodium methanethiolate, suitable Pd catalysts include palladium tetrakis(triphenylphosphine) and suitable inert high boiling solvents include dimethylsulfoxide as exemplified by Example 141 herein;

iv) When $R^4/R^5$ is halogen such as chloro, bromo or iodo, it may be converted to the corresponding ester —$CO_2R$ by treatment with carbon monoxide at high pressure with a Pd(0) or (II) catalyst, in an alcohol solvent (ROH wherein R is $C_1$–$C_4$ alkyl), in the presence of a base at elevated temperatures. For example the reaction may be carried out at pressures in the region of about 100 p.s.i., whilst suitable Pd catalysts include palladium tetrakis(triphenylphosphine), suitable bases include triethylamine and suitable alcohol solvents include methanol as exemplified by Example 151 herein;

v) When $R^4/R^5$ is halogen such as iodo, it may be converted to the corresponding amide —$CONR^6R^7$ wherein $R^6$ and $R^7$ are as previously defined herein, by treatment with carbon monoxide, the corresponding amine of formula $HNR^6R^7$ and a Pd(0)catalyst in an inert solvent which does not adversely affect the reaction. Suitable catalysts include palladium tetrakis (triphenylphosphine) and suitable solvents include dimethylformamide. The reaction is preferably conducted at an elevated temperature and pressure, as exemplified by Example 100 herein;

vi) When $R^4/R^5$ is halogen such as chloro, bromo or iodo, it may be converted to —$CH_2CN$ by reaction with tributyl(cyanomethyl)stannane [according to M. Kosugi, M. Ishiguro, Y. Negishi, H. Sano, T. Migita, Chem. Lett., 1984, 1511–1512] and a Pd-catalyst in a suitable solvent at elevated temperatures. Suitable catalysts include bis(acetonitrile)dichloro-palladium(II) and suitable solvents include m-xylene, as exemplified by Example 88 herein;

vii) When $R^4/R^5$ is halogen such as bromo, it may be converted to a heterocyclic group, by treatment with copper powder and the desired heterocyclic compound together with a base. Suitable heterocyclic groups are defined herein before and include 1,2,3-triazoles, suitable bases include potassium carbonate and the reaction is preferably carried out at elevated temperatures as exemplified by Example 181 herein;

viii) When $R^4/R^5$ is halogen such as bromo, it may be converted to an α,β-unsaturated sulfonamide, by treatment with vinylsulfonamide, a Pd(0) or (II) catalyst and a suitable base, in an inert solvent which does not adversely affect the reaction, at elevated temperatures. Suitable Pd catalysts include palladium (II) acetate in the presence of tri(o-tolyl)phosphine, suitable bases include triethylamine and suitable inert solvents include acetonitrile as exemplified by Example 67 herein;

ix) When $R^4/R^5$ is halogen such as bromo, it may be converted to an α,β-unsaturated amide, by treatment with acrylamide, a Pd(0) or (II) catalyst and a suitable base, in an inert solvent which does not adversely affect the reaction, at elevated temperatures. Suitable Pd catalysts include palladium (II) acetate in the presence of tri(o-tolyl)phosphine, suitable bases include triethylamine and suitable inert solvents include acetonitrile as exemplified by Example 68 herein;

x) When $R^4/R^5$ is an α,β-unsaturated sulfonamide, it may be converted to —$CH_2CH_2SO_2NH_2$, by treatment with a suitable reducing agent at an appropriate temperature, in an inert solvent which does not adversely affect the reaction. Suitable reducing agents include tosyl hydrazide at elevated temperature and suitable inert solvents include toluene as exemplified by Example 71 herein;

xi) When $R^4/R^5$ is nitro, it may be reduced to the corresponding —$NH_2$ group via treatment with a reducing agent in a protic solvent at, or above, room temperature. Suitable reducing agents include iron powder / calcium chloride, suitable protic solvents include aqueous ethanol and at a typical reaction temperature of from about 70° C. to about 100° C., preferably about 90° C., as exemplified by Example 107 herein;

xii) When $R^4/R^5$ is —$NH_2$, it may be converted to the corresponding —$NHSO_2R^9$ group by reaction with a sulfonylating agent in the presence of a base in an inert solvent which does not adversely affect the reaction at, or below, room temperature. Suitable sulfonylating agents include methanesulfonic anhydride, suitable bases include triethylamine and suitable inert solvents include tetrahydrofuran as exemplified by Example 114 herein;

xiii) When $R^4/R^5$ is —$NH_2$, it may be converted to a triazole by treatment with N'-[(dimethylamino)methylidene]-N,N-dimethylhydrazonoformamide and a suitable acid, in an inert solvent which does not adversely affect the reaction, at elevated temperature. Suitable acids include ρ-toluenesulfonic acid and suitable solvents include toluene as exemplified by Example 189 herein;

xiv) When $R^4/R^5$ is a —$NHSO_2R^9$ group, it may be converted to the corresponding —$NR^8SO_2R^9$ group via treatment with an alkylating agent and a base in a suitable inert solvent. Examples of suitable alkylating agents include 2-bromoethanol, suitable bases include potassium carbonate and suitable inert solvents include acetonitrile, as exemplified by Example 122 herein;

xv) When $R^4/R^5$ is a sulfonamide, it may be converted to an acyl sulfonamide by treatment with an acylating agent and a base in a solvent which does not adversely affect the reaction. Suitable acylating agents include acetic anhydride, suitable bases include triethylamine and suitable solvents include dichloromethane as exemplified by Example 66 herein;

xvi) When $R^4/R^5$ is —CN, it may be converted to the corresponding aldehyde by treatment with a hydride reducing agent in an inert solvent which does not adversely affect the reaction. Examples of suitable reducing agents include lithium aluminium hydride and suitable inert solvents include tetrahydrofuran. Such reactions are preferably carried out at low temperature and in an inert atmosphere as exemplified by Example 157 herein;

xvii) When $R^4/R^5$ is a nitrile —CN, it may be converted to the corresponding —$C(O)NH_2$ group by hydrolysis under basic, oxidative or acid conditions. Basic hydrolysis is preferably conducted with a hydroxide salt such as potassium hydroxide in a protic solvent such as t-butanol at elevated temperatures, as exemplified in Example 91 herein. Oxidative hydrolysis is preferably conducted with hydrogen peroxide in a polar solvent such as dimethylsulfoxide in the presence of a suitable base, such as potassium carbonate at, or below, room temperature, as exemplified by Example 90 herein. Acidic hydrolysis is preferably conducted with a strong acid, such as polyphosphoric acid, at elevated temperatures, as exemplified by Example 92 herein;

xviii) When $R^4/R^5$ is —CN, it may be reduced to the corresponding amine —$CH_2NH_2$ via treatment with a hydride reducing agent, such as lithium aluminium hydride as exemplified by Example 110 herein;

xix) When $R^4/R^5$ is —CHO, it may be reduced to the corresponding alcohol —$CH_2OH$ via treatment with a reducing agent in a suitable solvent. Examples of suitable reducing agents include sodium borohydride, and suitable solvents include ethanol as exemplified by Example 157 herein;

xx) When $R^4/R^5$ is, it may be converted to the corresponding sulfoxide —$S(O)R^9$ via low temperature treatment with an oxidising agent such as oxone (RTM) or hydrogen peroxide in a protic solvent as exemplified by Examples 145 or 149 herein;

xxi) When $R^4/R^5$ is —$SR^{10}$, it may be converted to the corresponding sulfone —$SO_2R^{10}$ via low temperature treatment with an oxidising agent such as oxone (RTM) or hydrogen peroxide in a protic solvent as exemplified by Examples 146 and 150 herein;

xxii) When $R^4/R^5$ is an ester, it may be reduced to the corresponding alcohol group —$CH_2OH$ via treatment with a hydride reducing agent, such as lithium aluminium hydride, as exemplified by Example 154 herein;

xxiii) When $R^4/R^5$ is an ester, it may be converted to the corresponding acid —$CO_2H$ by treatment with a suitable hydroxide salt in the presence of water and a suitable co-solvent. Suitable hydroxide salts include lithium hydroxide and suitable co-solvents include tetrahydrofuran, as exemplified by Example 158 herein; and xxiv) When $R^4/R^5$ is a carboxylic acid, it may be converted to the corresponding amide —$CONR^6R^7$ by treatment with a coupling agent, a base and an amine $HNR^6R^7$ in a suitable inert solvent which does not adversely affect the reaction. Suitable coupling agents include 1-(3-dimethylaminopropyl)-3-ethylcarbodiimide hydrochloride in the presence of 1-hydroxybenzotriazole, suitable bases include triethylamine and suitable solvents include dichloromethane as exemplified by Example 159 herein.

Alternatively, compounds of general formula (I) having a particular $NR^1R^2$ group may be converted into compounds of general formula (I) having a different $NR^1R^2$ group. For example:

i) compounds of formula (I) wherein either $R^1$ or $R^2$ is hydrogen, can be converted into other compounds of formula (I) wherein neither $R^1$ nor $R^2$ are hydrogen, by reaction of the compound of formula (I) with an aldehyde and a hydride reducing agent. Suitable aldehydes include formaldehyde, suitable reducing agents include sodium tri(acetoxy)borohydride and the reaction is preferably conducted in a solvent which does not interfere with the reaction, such as dichloromethane at or below room temperature, as exemplified by Example 183 herein; and ii) compounds of formula (I) wherein $R^1$ is hydrogen, can be converted into other compounds of formula (I) wherein $R^1$ is methyl, by reaction of the compound of formula (I) with a formylating agent in a suitable solvent, followed by subsequent reduction of the intermediate N-formyl compound with a hydride reducing agent in an inert solvent, preferably at elevated temperature. Suitable formylating agents include pentafluorophenyl formate (formed from formic acid, pentafluorophenol and dicyclohexylcarbodiimide) and suitable solvents for the formylation include dichloromethane. Suitable reducing agents include borane-tetrahydrofuran complex and suitable inert solvents for the reduction include tetrahydrofuran as exemplified by Example 128 herein.

Alternatively, compounds of general formula (I) may be prepared from compounds of formula (VIII) (see Scheme 3) wherein L is as defined for Scheme 1 and T is a group which can be converted into $CH_2NR^1R^2$. Examples of suitable T substituents include: carboxy, alkoxycarbonyl, —CN and —C(O)$NR^1R^2$.

SCHEME 3

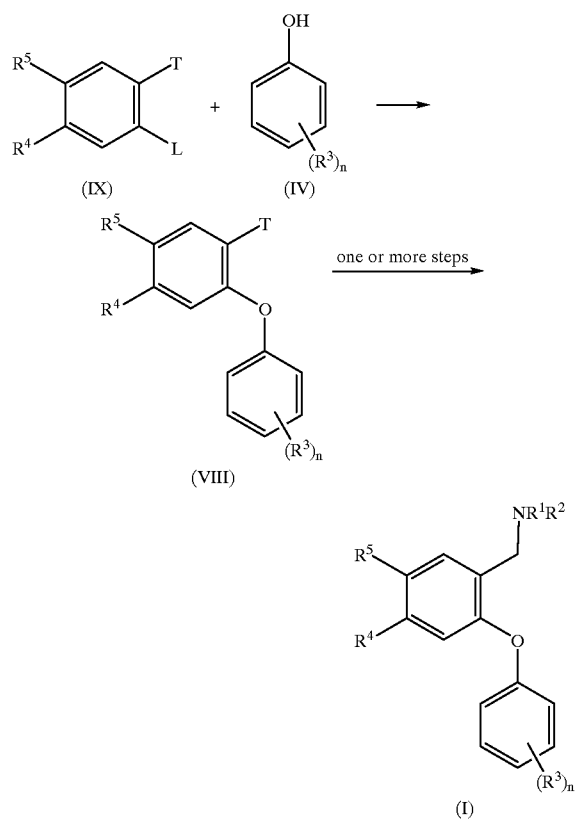

Methodologies for converting compounds of formula (VIII) to (I), include:
i) where T is carboxy or alkoxycarbonyl, by reaction with an amine of general formula $NHR^1R^2$ to form an amide followed by reduction of the amide to provide a compound of formula (I). Such compounds of general formula (I) may be further reacted with a suitable aldehyde and hydride reducing agent, or a formylating agent followed by a hydride reducing agent, to provide a compound of formula (I);
ii) where T is —CN, by reduction to its corresponding amine of formula —$CH_2NH_2$. To provide further compounds of general formula (I), wherein either one or both of $R^1$ or $R^2$ are not hydrogen, the amine can be further reacted with a suitable aldehyde and hydride reducing agent, or a formylating agent followed by a hydride reducing agent, to provide a compound of formula (I); and
iii) where T is —C(O)$NR^1R^2$, by reduction to provide an amine followed optionally by an appropriate conversion of $R^1$ and/or $R^2$ if either is hydrogen into alternative $R^1$ and/or $R^2$ groups via treatment with aldehyde with subsequent reduction, or by treatment with a formylating agent followed by a hydride reducing agent.

Compounds of general formula (VIII) may be prepared in turn by the coupling of compounds of general formula (IX) and compounds of the general formula (IV). Reagents and conditions for such coupling reactions are as previously defined for the coupling of compounds of general formulae (IV) and (V) in Scheme 1.

Compounds of general formula (IX) may be prepared in turn from compounds of general formula (X) (see Scheme 4).

SCHEME 4

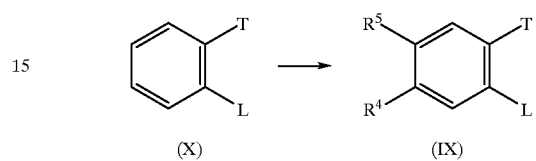

Compounds of formula (IX) may be prepared by aromatic electrophilic substitution of compounds of formula (X) to give compounds of formula IX directly. Alternatively compounds of formula (IX) may be prepared in two or more steps; aromatic electrophillic substitution of compounds of formula (X) to give intermediate compounds which then undergo further reaction to give compounds of formula (IX). The intermediate compounds may be isolated or generated in sitiu without isolation. A preferred route is shown in Scheme 5.

SCHEME 5

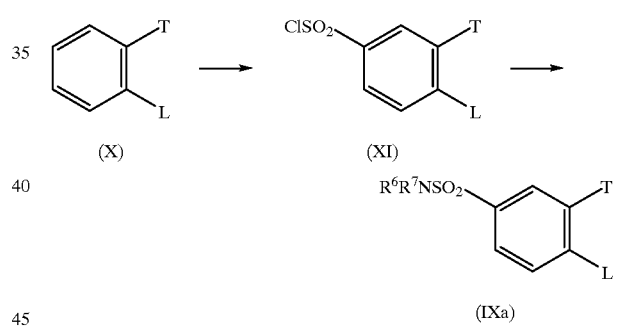

Compounds of formula (X) are reacted with sulfonyl chloride to give compounds of formula (XI) followed by reaction with $NHR^6R^7$ to give compounds of formula (IXa).

A preferred route to compounds of formula (Ia) is shown in Scheme 6. Preferred reaction conditions for the final step involving reduction of compounds of formula (VIIIa) to compounds of formula (Ia), are treatment with borane-tetrahydrofuran complex (see Example 61.)

SCHEME 6

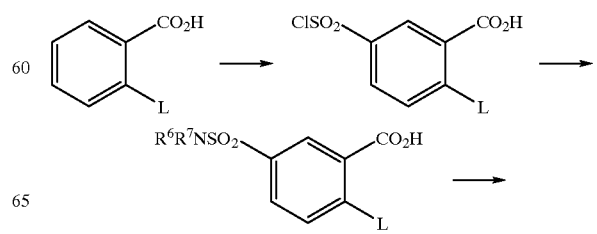

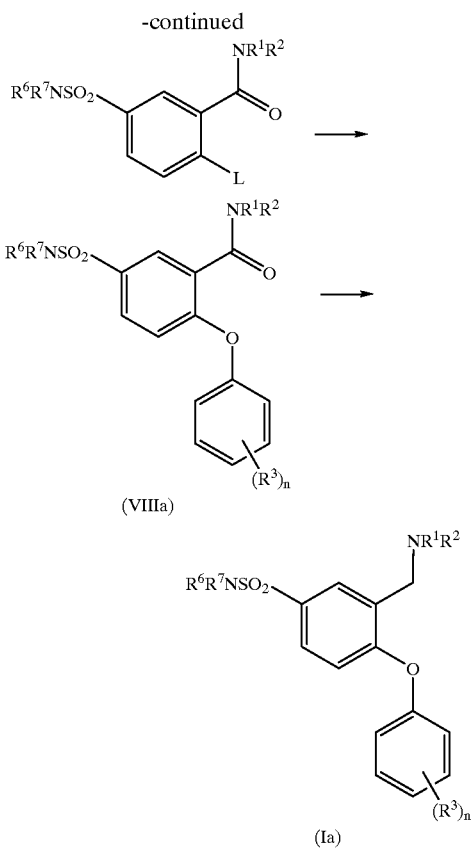

According to further aspects, the invention provides compounds to formulae (II), (III), (VII), (VIII), (VIIIa) and (XII) as defined above. In compounds of general formula (II) when $R^1$ and $R^2$ are methyl, and n is 1, $R^3$ is not a —SMe group para to the ether linkage linking rings A and B.

Compounds of formulae (IV), (V), (VI) or (IX) are either known and available from commercial sources or are available from commercially available materials using known techniques.

It will be apparent to those skilled in the art that sensitive functional groups may need to be protected and deprotected during synthesis of a compound of formula I. This may be achieved by conventional techniques, for example as described in 'Protective Groups in Organic Synthesis', 3rd edition, by T W Greene and P G M Wuts, John Wiley and Sons Inc, 1999. Example 121 provides an example of a protecting group strategy employed in the synthesis of a compound of the present invention.

The skilled chemist will appreciate that diaryl ethers may be prepared using a number of synthetic methodologies. For a review of methodologies see J S Sawyer, *Tetrahedron*, 56 (2000) 5045–5065, incorporated herein by reference.

The compounds of the invention are useful because they have pharmacological activity in mammals, including humans. More particularly, they are useful in the treatment or prevention of a disorder in which the regulation of monoamine transporter function is implicated. Disease states that may be mentioned include hypertension, depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimers disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourettes syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

Disorders of particular interest include depression, attention deficit hyperactivity disorder, obsessive-compulsive disorder, post-traumatic stress disorder, substance abuse disorders and sexual dysfunction including (in particular) premature ejaculation. Premature ejaculation may be defined as persistent or recurrent ejaculation before, upon or shortly after penile penetration of a sexual partner. It may also be defined as ejaculation occurring before the individual wishes [see '*The Merck Manual*', 16th edition, p 1576, published by Merck Research Laboratories, 1992].

Thus, according to further aspects, the invention provides:
i) a compound of formula (I), as defined in the first aspect, or pharmaceutically acceptable salts, solvates or polymorphs thereof, for use as a pharmaceutical;
ii) the use of a compound of formula (I), as defined in the first aspect, or pharmaceutically acceptable salts, solvates or polymorphs thereof, in the manufacture of a medicament for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation;
iii) the use of a compound of general formula (I) as defined in the first aspect, or pharmaceutically acceptable salts, solvates or polymorphs thereof, in the manufacture of a medicament for the treatment or prevention of premature ejaculation, and also provides a method of treatment or prevention of premature ejaculation comprising the administration of this compound to a patient in need of such treatment or prevention;
iv) a method of treatment or prevention of depression, attention deficit hyperactivity disorder, obsessive-compulsive disorder, post-traumatic stress disorder, substance abuse disorders or sexual dysfunction including premature ejaculation, which comprises administering a therapeutically effective amount of a compound of formula (I), as defined in the first aspect, or pharmaceutically acceptable salts, solvates or polymorphs thereof, to a patient in need of such treatment or prevention;
v) a method of increasing ejaculatory latency which comprises the administration of an effective amount of a compound of formula (I), as defined in the first aspect, or pharmaceutically acceptable salts, solvates or polymorphs thereof, to a male desiring increased ejaculatory latency; and vi) a compound of formula (I), as defined in the first aspect, or pharmaceutically acceptable salts, solvates or polymorphs thereof, for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation.

It is to be appreciated that all references herein to treatment include curative, palliative and prophylactic treatment.

The compounds of the invention may be administered alone or as part of a combination therapy. If a combination of active agents are administered, then they may be administered simultaneously, separately or sequentially. In particular, the compounds of the invention may be combined with the following for the treatment of premature ejaculation:

Alpha-blockers (e.g. phentolamine, doxazasim, tansulosin, terazasin, prazasin and Example 19 of WO9830560;

Apomorphine —teachings on the use of apomorphine as a pharmaceutical may be found in U.S. Pat. No. 5,945,117;

Dopamine D2 agonists (e.g. Premiprixal, Pharmacia Upjohn compound number PNU95666);

Melanocortin receptor agonists (e.g. Melanotan II);

PGE1 receptor agonists (e.g. alprostadil);

Mono amine transport inhibitors, particularly Noradrenaline Re-uptake Inhibitors (NRIs) (e.g. Reboxetine), other Serotonin Re-uptake Inhibitors (SRIs) (e.g. paroxetine) or Dopamine Re-uptake Inhibitors (DRIs);

5-HT3 antagonists (e.g. ondansetron and granisetron); and

PDE inhibitors such as PDE2 (e.g. erythro-9-(2-hydroxyl-3-nonyl)-adenine) and Example 100 of EP 0771799-incorporated herein by reference) and in particular a PDE5 inhibitor (e.g. sildenafil, 1-{[3-(3,4-dihydro-5-methyl-4-oxo-7-propylimidazo[5, 1-f]-as-trazin-2-yl)-4-ethoxyphenyl]sulfonyl}-4-ethylpiperazine i.e. vardenafil / Bayer BA 38-9456) and IC351 (see structure below, Icos Lilly).

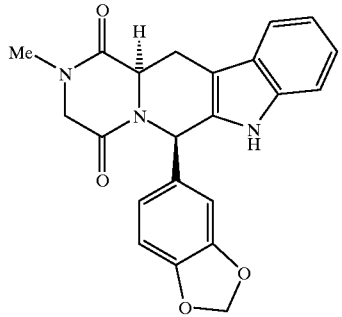

IC351(Icos Lilly)

For human use the compounds of the invention can be administered alone but in human therapy will generally be administered in admixture with a suitable pharmaceutical excipient, diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 2.5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetra- fluoro-ethane, a hydrofluoroalkane such as 1,1,1,2-tetrafluoroethane (HFA 134A [trade mark]) or 1,1,1, 2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of compounds of formula (I), and their pharmaceutically acceptable salts, will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred. Preferably, administration takes place shortly before an effect is required.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of formula (i), as defined in the first aspect, or a pharmaceutically acceptable salt thereof, and a pharmaceutically acceptable adjuvant, diluent or carrier.

The invention is illustrated by the following non-limiting Examples in which the following abbreviations and definitions are used:

| | |
|---|---|
| DMAP | 4-(dimethylamino)pyridine |
| DMF | N,N-dimethylformamide |
| br | broad |
| Celite ® | filter agent, from Aldrich Chemical Company |
| δ | chemical shift |
| d | doublet |
| DCM | dichloromethane |
| DMPU | 1,3-dimethyl-3,4,5,6-tetrahydro-2(1H)-pyrimidinone |
| DMSO | dimethylsulfoxide |
| ES⁺ | electrospray ionisation positive scan |
| ES⁻ | electronspray ionisation negative scan |
| h | hours |
| m/z | mass spectrum peak |
| HPLC | High Pressure Liquid Chromatography |
| min | minutes |
| MS | mass spectrum |
| NMR | nuclear magnetic resonance |
| Oxone ® | potassium peroxymonosulfate, from Aldrich Chemical Company |

-continued

| | |
|---|---|
| q | quartet |
| s | singlet |
| t | triplet |
| Tf | trifluoromethanesulfonyl |
| TFA | trifluoroacetic acid |
| TFAA | trifluoroacetic anhydride |
| THF | tetrahydrofuran |
| TLC | thin layer chromatography |
| TS⁺ | thermospray ionisation positive scan |
| WSCDI | 1-(3-dimethylaminopropyl)-3-ethylcarbodiimide hydrochloride |
| Δ | heat |

Where indicated, compounds were characterised as their hydrochloride salts. A typical procedure for formation of hydrochloride salts is given in Preparation 21. The procedure can be carried out with other solvents e.g. diethyl ether or DCM.

The powder X-ray diffraction (PXRD) patterns were determined using a Siemens D5000 powder X-ray diffractometer fitted with a theta-theta goniometer, automatic beam divergence slits, a secondary monochromator and a scintillation counter. The specimen was rotated whilst being irradiated with copper K-alpha1 X-rays (Wavelength=1.5046 Angstroms) filtered with a graphite monochromator (λ=0.15405 nm) with the X-ray tube operated at 40 kV/40 mA. The main peaks (in degrees 2 θ) of the PXRD patterns for the various solid forms are illustrated.

Melting points were determined using a Perkin Elmer DSC7 at a heating rate of 20° C./minute.

EXAMPLES 1–15

Examples 1–15 were prepared according to the procedure described in preparation 21 herein from the aldehyde indicated and the appropriate amine.

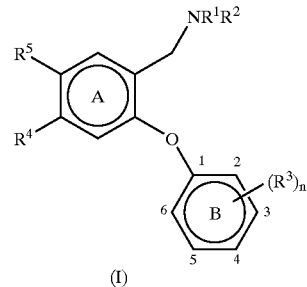

(I)

| Example | Starting Material | R⁴ | R⁵ | (R³)ₙ | R¹ | R² | Data |
|---|---|---|---|---|---|---|---|
| 1 | Prep. 2 | H | Br | 3-CF₃ | Me | Me | δ$_H$(CDCl₃, 300MHz) 2.81(6H, s), 4.30(2H, s), 6.78(1H, d), 7.22 (1H, d), 7.25(1H, s), 7.43–7.57(3H, m), 8.07 (1H, s); MSm/z(TS⁺) 374, 376(MH⁺). |
| 2ᵃ (HCl salt) | Prep 3 | H | Br | 4-CF₃ | —(CH₂)₃— | | δ$_H$(CDCl₃, 300MHz) 2.34(1H, m), 2.80(1H, q), 3.92(2H, m), 4.27 (2H, s), 4.38(2H, m), 6.78(1H, d), 7.18(2H, d), 7.50(1H, d), 7.63 (2H, d), 7.98(1H, s), |

-continued

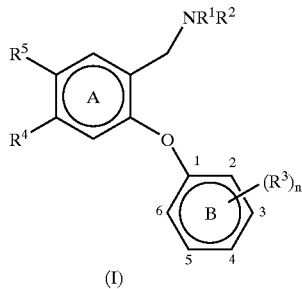

(I)

| Example | Starting Material | R⁴ | R⁵ | (R³)ₙ | R¹ | R² | Data |
|---|---|---|---|---|---|---|---|
| 3 (HCl salt) | Prep 3 | H | Br | 4-CF₃ | Me | Me | 13.20(1H, s); MSm/z (TS⁺)386, 388(MH⁺). |
| | | | | | | | $\delta_H$(CDCl₃, 300MHZ) 2.82(6H, d), 4.28(2H, d), 6.82(1H, d), 7.13 (2H, d), 7.56(1H, d), 7.65(2H, d), 8.05 (1H, s), 12.95(1H, s); MSm/z(TS⁺)374, 376 (MH⁺). |
| 4ᶜ (HCl salt) | Prep 10 | H | F | 4-SMe | Me | H | $\delta_H$(CDCl₃, 400MHz) 2.46(3H, s), 2.60(3H, s), 4.18(2H, s), 6.78 (1H, m), 7.00(3H, m), 7.22(2H, m), 7.52(1H, dd), 9.84(2H, br); MS m/z(TS⁺)278(MH⁺). |
| 5ᵇ | Prep 10 | H | F | 4-SMe | Et | H | $\delta_H$(CDCl₃, 400MHz) 1.08(3H, t), 2.44(3H, s), 2.63(2H, q), 3.77 (2H, s), 6.80–6.92(4H, m), 7.18(1H, dd), 7.23 (2H, d); MSm/z(TS⁺) 292(MH⁺). |
| 6ᵃ | Prep 10 | H | F | 4-SMe | —(CH₂)₃— | | $\delta_H$(CDCl₃, 300MHz) 2.03–2.12 (2H, m), 2.43 (3H, s), 3.30–3.29(4H, m), 3.56(2H, m), 6.79–6.90(4H, m), 7.17–7.23 (3H, m); MSm/z304 (MH⁺) |
| 7 | Prep 7 | H | Br | 4-OCF₃ | Me | Me | $\delta_H$(CDCl₃, 300MHz) 2.23(6H, s), 3.42(2H, s), 6.78(1H, d), 6.91 (2H, m), 7.16(2H, m), 7.35(1H, dd), 7.65(1H, d); MSm/z(TS⁺)390 (MH⁺). |
| 8 | Prep 8 | Br | H | 4-OCF₃ | Me | Me | $\delta_H$(CDCl₃, 300MHz) 2.25(6H, s), 3.40(2H, s), 6.95(2H, d), 7.00 (1H, d), 7.20(2H, d), 7.28(1H, dd), 7.38(1H, d); MSm/z(TS⁺)390 (MH⁺). |
| 9 (HCl salt) | Prep 9 | H | Br | 4-SMe | Me | Me | $\delta_H$(CDCl₃, 300MHz) 2.48(3H, s), 2.82(6H, d), 4.30(2H, d), 6.70 (1H, d), 6.92(2H, d), 7.25(2H, d), 7.42(1H, dd), 7.96(1H, d), 12.55 (1H, br); MSm/z(TS⁺) 352(MH⁺) |

-continued

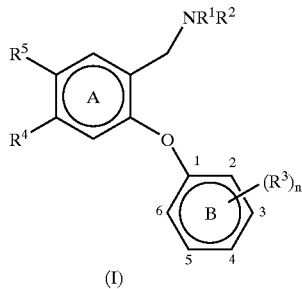

(I)

| Example | Starting Material | R⁴ | R⁵ | (R³)ₙ | R¹ | R² | Data |
|---|---|---|---|---|---|---|---|
| 10 (HCl salt) | Prep 10 | H | F | 4-SMe | Me | Me | δ_H(CDCl₃, 300MHz) 2.48(3H, s), 2.81(6H, m), 4.28(2H, m), 6.86 (3H, m), 7.06(1H, m), 7.18(1H, m), 7.70(1H, dd), 12.78(1H, br); MS m/z(TS⁺)292(MH⁺). |
| 11ᶜ | Prep 5 | Br | H | 4-CF₃ | Me | H | δ_H(d₆-DMSO, 400MHz) 2.53(3H, s), 4.10(2H, s), 7.16(1H, s), 7.26 (2H, d), 7.50(1H, d), 7.65(1H, d), 7.79(2H, d), 9.28(2H, brs); MS m/z360, 361(MH⁺) |
| 12 | Prep 5 | Br | H | 4-CF₃ | Me | Me | δ_H(CD₃OD, 300MHz) 2.93(6H, s), 4.84(2H, s), 7.16(1H, s), 7.30 (2H, d), 7.53(2H, dd), 7.78(2H, d); MSm/z (TS⁺)374, 376(MH⁺). |
| 13 | Prep 14 | Br | H | 4-SMe | Me | Me | Free base: δ_H(CDCl₃, 400MHz)2.25(6H, s), 2.48(3H, s), 3.43(2H, s), 6.89(2H, d), 6.97 (1H, d), 7.23–7.28(3H, m), 7.33(1H, d); MS m/z(TS⁺)352, 354 (MH⁺) |
| 14 | Prep 13 | H | OMe | 4-SMe | Me | Me | HCl salt: δ_H(CD₃OD, 400MHz)2.46(3H, s), 2.90(6H, s), 3.83(3H, s), 4.34(2H, s), 6.92 (1H, d), 6.98(2H, d), 7.05(1H, dd). 7.15(1H, dd), 7.31(2H, d); MS m/z(TS⁺)304, 340 (MH⁺) |
| 15 | Prep 18 | OMe | OMe | 4-SMe | Me | Me | HCl salt: δ_H(CD₃OD, 400MHz)2.46(3H, s), 2.87(6H, s), 3.72(3H, s), 3.87(3H, s), 4.25 (2H, s), 6.60(1H, s), 6.97(2H, d), 7.13(1H, s), 7.31(2H, d); MS m/z(TS⁺)334(MH⁺) |

ᵃAzetidine hydrochloride was used in place of Me₂NH.HCl.
ᵇFree EtNH₂ (as a 2M solution in THF) was used as the amine component, THF alone was the reaction solvent, and Et₃N was omitted from the reaction mixture.
ᶜMeNH₂.HCl was used in place of Me₂NH.HCl.AcOH(1 equiv. relative to Et₃N) was an additional component of the reaction mixture.

EXAMPLE 16

N-{5-Iodo-2-[4-(trifluoromethoxy)phenoxy]benzyl}-N,N-dimethylamine

TfOH, DCM, N-iodosuccinimide

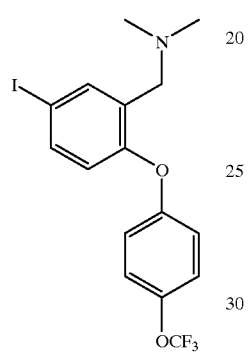

To a stirred solution of the amine of preparation 23 (4.0 g, 12.9 mmol) in DCM (30 mL) at 0° C. was added trifluoromethanesulfonic acid (5.7 mL, 64.5 mmol) followed by portionwise addition of N-iodosuccinimide (2.89 g, 12.9 mmol) over 15 min. After the addition was complete the mixture was allowed to stir at 0° C. for 30 min and then at 10° C. for 1 h. The reaction was quenched by the addition of aqueous sodium hydroxide (2 M) and extracted three times with ethyl acetate. The combined organic extracts were washed with sodium thiosulfate solution, dried (MgSO$_4$) and evaporated to a red oil which was purified by flash chromatography [SiO$_2$; DCM/ MeOH/ 880 NH$_3$ (95:5:0.5)] to afford the desired iodide compound as a red oil (4.16 g, 74%); δ$_H$ (CDCl$_3$, 400 MHz) 2.24 (6 H, s), 3.40 (2 H, s), 6.64 (1 H, d), 6.92 (2 H, m), 7.16 (2 H, m), 7.53 (1 H, dd), 7.83 (1 H, d); MS m/z (TS$^+$) 438 (MH$^+$).

EXAMPLES 17–18

The following iodides were produced in an analogous fashion to the reaction described for the preparation of Example 16.

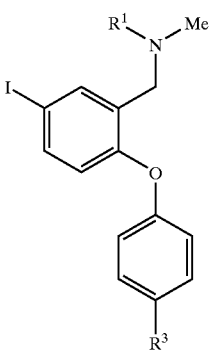

| Example | Starting Material | R$^1$ | R$^3$ | Data |
|---|---|---|---|---|
| 17 | Prep 26 | H | OCF$_3$ | δ$_H$(CDCl$_3$, 300MHz)1.88(1H, br), 2.43(3H, s), 3.73(2H, s), 6.62(1H, d), 6.95(2H, m), 7.17 (2H, m), 7.53(1H, dd), 7.77(1H, d); MSm/z (TS$^+$)423(M$^+$) |
| 18 | Prep 22 | Me | CF$_3$ | δ$_H$(CDCl$_3$, 400MHz)2.23(6H, s), 3.37(2H, s), 6.70(1H, d), 6.95(2H, d), 7.55(2H, d), 7.57(1H, dd), 7.88(1H, d); MSm/z(TS$^+$)422(MH$^+$). |

EXAMPLE 19

N,N-Dimethyl-N-{2-[4-(methylsulfanyl)phenoxy]-5-nitrobenzyl}amine

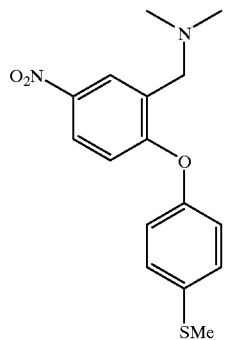

The title compound was prepared from the aldehyde of Preparation 19 according to the procedure used for preparation 21. Acetic acid (1 equiv. relative to trethylamine) was an additional component of the reaction mixture. δH (CDCl$_3$, 400 MHz) 2.33 (6 H, s), 2.50 (3 H, s), 3.60 (2 H, s), 6.79 (1 H, d), 6.98 (2 H, d), 7.29 (2 H, d), 8.03 (1 H, dd), 8.39 (1 H, d); MS m/z (TS$^+$) 319 (MH$^+$).

EXAMPLE 20

N-Methyl-N-{5-nitro-2-[4-(trifluoromethyl)phenoxy]benzyl}amine

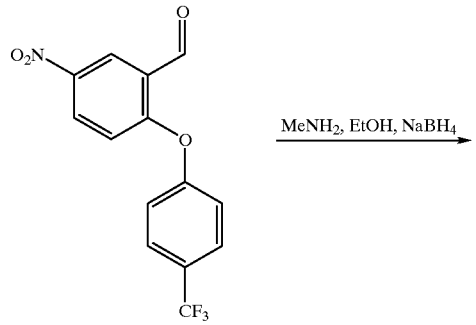

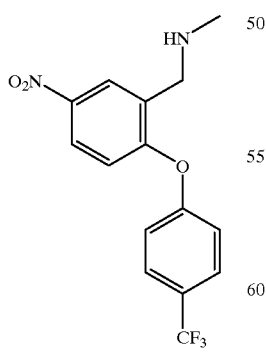

The aldehyde of preparation 20 (5.0 g, 16.07 mmol) was dissolved in a solution of monomethylamine in ethanol (ca. 8 M) (20 mL, 160 mmol), and the mixture stirred for 30 min at room temperature to form an orange solution. Sodium borohydride (3.0 g, 80 mmol) was added portionwise over 10 min and stirring continued for 30 min, by which time the solution had become dark red. The reaction was quenched by cautiously pouring the reaction mixture into hydrochloric acid (2 M, 100 mL). The mixture was basified by pouring this solution into a large excess of potassium carbonate to give a mixture with ca. pH 10, which was extracted with ethyl acetate (3×70 mL). The combined organic fractions were dried (MgSO$_4$) and evaporated to an orange oil which was filtered through a short plug of silic, eluting with DCM/ methanol/ 880 ammonia (93:7:1). After evaporation, the residue was further purified by flash chromatography [SiO$_2$; pentane/ ethyl acetate (2:1) to elute non-basic materials followed by DCM/ methanol/ 880 ammonia (93:7:1)] to afford the desired amine compound as a yellow oil (3.08 g, 59%); δ$_H$ (CDCl$_3$, 400 MHz) 2.49 (3 H, s), 3.89 (2 H, s), 6.89 (1 H, d), 7.12 (2 H, d), 7.67 (2 H, d), 8.10 (1 H, dd), 8.40 (1 H, d); MS m/z (TS$^+$) 327 (MH$^+$).

EXAMPLE 21

N,N-Dimethyl-N-{5-nitro-2-[4-(trifluoromethyl)phenoxy]benzyl}amine

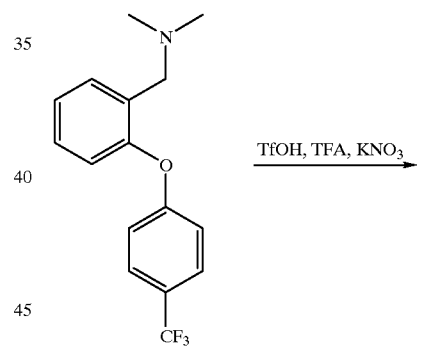

TfOH, TFA, KNO$_3$

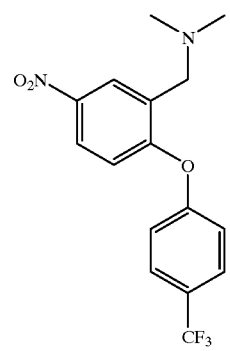

Trifluoromethanesulfonic acid (500 μL) was added dropwise to a solution of the amine of preparation 22 (504 mg, 1.71 mmol) in TFA (4.5 mL) at 0° C. under nitrogen followed by potassium nitrate (173 mg, 1.71 mmol). The mixture was stirred at 0° C. for 75 min then poured onto ice and basified with sodium hydroxide pellets. The aqueous mixture was extracted with ethyl acetate and the organic extract was washed with brine, dried (MgSO₄) and concentrated in vacuo. The residue was purified by flash chromatography [SiO₂; DCM/ methanol/ 880 ammonia (99:1:0.5)] to give the desired nitro compound (400 mg, 69%) as yellow oil; $\delta_H$ (CDCl₃, 300 MHz) 2.30 (6 H, s), 3.55 (2 H, s), 6.92 (1 H, d), 7.08 (2 H, d), 7.65 (2 H, d), 8.10 (1 H, dd), 8.45 (1 H, d); MS m/z (TS⁺) 341 (MH⁺).

EXAMPLE 22

N,N-Dimethyl-N-{5-nitro-2-[4-(trifluoromethoxy)phenoxy]benzyl}amine

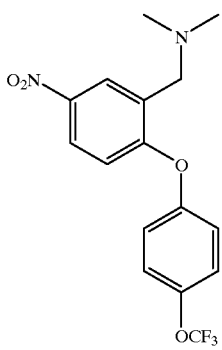

The reaction of example 21 was repeated under similar conditions using the amine of preparation 23 to provide the title nitro compound. $\delta_H$ (CDCl₃, 400 MHz) 2.33 (6 H, s), 3.58 (2 H, s), 6.83 (1 H, d), 7.05 (2 H, m), 7.25 (2 H, m), 8.06 (1 H, d), 8.41 (1 H, s); MS m/z (TS⁺) 357 (MH⁺).

EXAMPLE 23

N-{5-Bromo-2-[4-(methylsulfanyl)phenoxy]benzyl}-N-methylamine

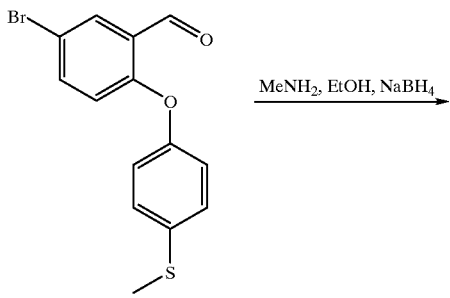

-continued

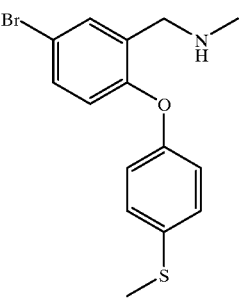

The bromoaldehyde of preparation 9 (39.0 g, 120 mmol), was dissolved in monomethylamine (7.37 mL, 33% in ethanol) and the solution stirred for 10 min before the addition of sodium borohydride (6.8 g, 180 mmol). The reaction mixture was stirred for 3 hrs at room temperature before being added cautiously to 3 M HCl. After the addition was complete the mixture was left for 10 min before adjusting the pH to 14 with sodium hydroxide (3 M). The aqueous phase was extracted with ethyl acetate and the organic layer washed with brine, dried (MgSO₄) and evaporated. The resulting oil was taken up in diethyl ether and treated with excess hydrochloric acid (1 M in di ethyl ether). The salt was collected by filtration and washed with DCM. The washed solid was partitioned between ethyl acetate and sodium hydroxide (3 M), the organic layer separated, washed with brine, dried and evaporated to a colourless oil (24.6 g, 61%); $\delta^H$ (CDCl₃, 300 MHz) 2.43 (3 H, s), 2.47 (3 H, s), 3.76 (2 H, s), 6.72 (1 H, d), 6.87 (2 H, d), 7.24 (2 H, d), 7.30 (1 H, dd), 7.54 (1 H, d); MS m/z (TS⁺) 338/ 340 (MH⁺).

EXAMPLES 24–27

A series of secondary amines was prepared from the requisite aldehyde using the procedure described for example 23.

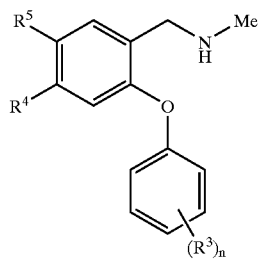

| Example | Starting material | R⁴ | R⁵ | (R³)ₙ | Data |
|---|---|---|---|---|---|
| 24 | Prep 8 | Br | H | 4-OCF₃ | HCl salt: $\delta_H$(CDCl₃, 400MHz)2.59(3H, s), 4.16(2H, s), 6.88(1H, s), 7.18–7.29(5H, m), 7.59(1H, d), 9.82(2H, brs); MSm/z (TS⁺)376, 378(MH⁺) |
| 25 | Prep 13 | H | OMe | 4-SMe | HCl salt: $\delta_H$(CD₃OD, 300MHz)2.47(3H, s), 2.75(3H, s), 3.82(3H, s), 4.20(2H, s), 6.95(4H, m), 7.10(1H, dd), 7.30(2H, d); MSm/z(TS⁺)304(MH⁺) |
| 26 | Prep 16 | H | Br | 3-OMe 4-SMe | Free base: $\delta_H$(CDCl₃, 400MHz)2.43(3H, s), 2.46(3H, s), 3.77(2H, s), 3.87(3H, s), 6.48(1H, dd), 6.56(1H, s)6.78(1H, d), 7.15(1H, d), 7.33(1H, dd), 7.57(1H, d); MSm/z(TS⁺)368/370(MH⁺) |
| 27 | Prep 17 | H | Br | 3-CF₃ 4-SMe | Free base: $\delta_H$(CDCl₃, 300MHz)2.44(3H, s), 2.51(3H, s), 3.75(2H, s), 6.78(1H, d), 7.03(1H, dd), 7.39(2H, t), 7.61(1H, s) |

EXAMPLE 28

3-[(Dimethylamino)methyl]-4-[4-(methylsulfanyl)phenoxy]benzenesulfonamide

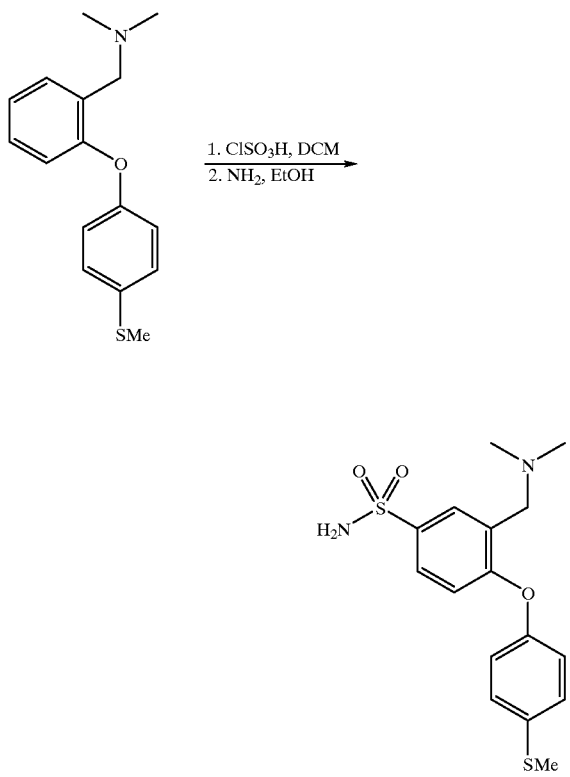

Chlorosulfonic acid (48.1 mL, 724 mmol) was added cautiously to a solution of the compound of preparation 21 (19.8 g, 72.4 mmol) in DCM (290 mL) cooled to 0° C. and the mixture was stirred for 4 h before being poured into ice-water (1000 mL) and extracted with DCM (300 mL). This crude solution of sulfonyl chloride was treated with saturated ethanolic ammonia (1160 mL) and stirred at room temperature overnight before being concentrated in vacuo. The reaction was repeated twice more under identical conditions and the material from the three runs was combined. Purification of the combined residues by flash chromatography [SiO₂; (MeOH/ 880 NH₃) (9:1)} (0→5%) in DCM] gave a clean sample of the desired sulfonamide (3.96 g, 5%) as well as slightly contaminated sulfonamide (19.73 g, 26%). For pure free base; $\delta_H$ (CDCl₃, 300 MHz) 2.24 (6 H, s), 2.48 (3 H, s), 3.56 (2 H, s), 5.25 (2 H, br), 6.81 (1 H, d), 6.92 (2 H, d), 7.27 (2 H, d), 7.70 (1 H, dd), 8.04 (1 H, d); MS m/z (TS⁺) 353 (MH⁺). Each sample was converted to the hydrochloride salt by stirring a suspension in diethyl ether with excess ethereal hydrochloric acid for 30 mins, the precipitate was collected and dried, and then recrystallised from hot ethanol/ ethyl acetate (1:1) (m.p. 193–194° C.) to afford 2.69 g and 15.63 g of the hydrochloride of the desired sulfonamide from each batch respectively; $\delta_H$ (d₆-DMSO, 400 MHz) 2.48 (3 H, s), 2.78 (6 H, s), 4.43 (2 H, s), 6.86 (1 H, d), 7.19 (2 H, d), 7.31–7.38 (4 H, m), 7.82 (1 H, dd), 8.11 (1 H, dd), 10.44 (1 H, brs); MS m/z(TS⁺) 353 (MH⁺).

Alternatively, the title compound can be prepared via the secondary amine of Example 42, which itself is also available by borane reduction of the amide from preparation 31 using the method described for Example 61.

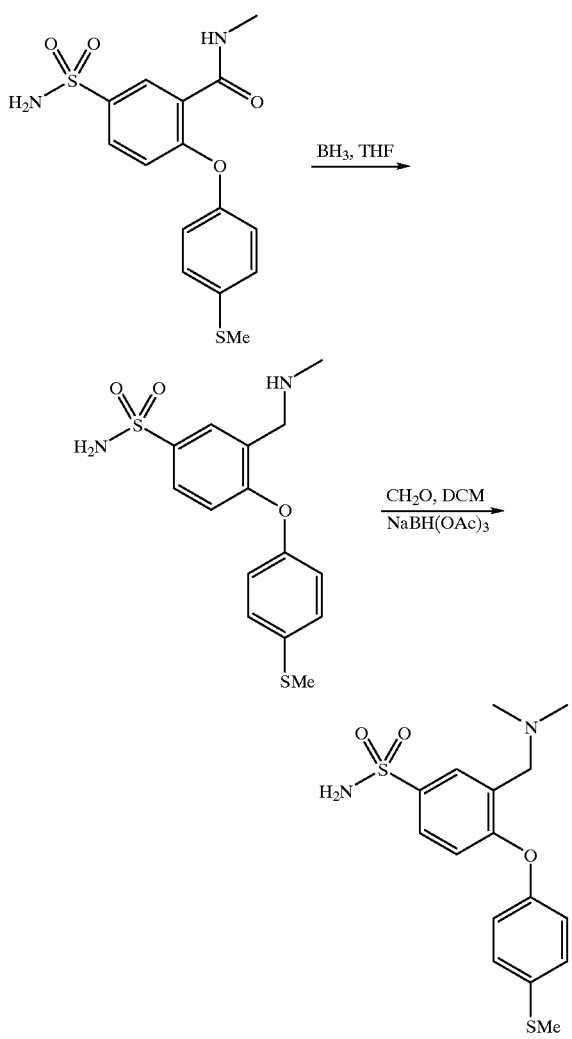

Alternatively the title compound may be prepared as follows:

A solution of the hydrochloride salt of the title product from preparation 21 (113 g) in dichloromethane (1130 mL) was slowly added to a solution of chlorosulfonic acid (428 g) in dichloromethane (230 mL) keeping the temperature between 0 and 5° C. After 1 h at 0–5° C., the reaction mixture was quenched slowly into 5% trifluoroacetic acid in water (1200 mL), keeping the temperature between 0–10° C. The two phases were separated and the dichloromethane layer removed in vacuo to give an oil. Acetonitrile (1360 mL) was added and to this solution was slowly added POCl$_3$ (140 g). The resulting slurry was heated at reflux at which point it became a solution. After 1 h the reaction mixture was cooled to room temperature and quenched into ice/water (1200 mL) keeping the temperature below 20° C. The mixture was extracted with dichloromethane (1×1400 mL and 1×400 mL) and the combined extracts stirred at room temperature while adding aqueous ammonia (250 mL). After 1 h the layers were separated and the aqueous layer further extracted with dichloromethane (400 ml). The combined dichloromethane layers were concentrated in vacuo. Water (539 ml) was added and to this mixture was added aquesou sodium hydroxide solution (108 ml; 46–48%w/w) and the slurry stirred for 1 h at room temperature and a further 1 h at 10° C. The solid was filtered and reslurried in water (500 mL) and the pH adjusted to 6–6.5 by addition of 1:1, water:concentrated hydrochloric acid. The resulting slurry was stirred for 1 h at 10° C. or below. The solid was filtered, washed with water (107 mL) and the damp solid reslurried in 9:1, water:acetone (289 mL:32 mL) for 1 h below 10° C. This slurry was filtered and dried in a vacuum oven at 50° C. overnight. A solution of the above solid in acetone (565 mL) was slurried with carbon (Norit SX plus, 50%w/w) filtered and treated with another charge of carbon (Norit SX plus, 50%w/w). This was again filtered and the solution concentrated, replacing with water (1130 mL). The slurry was granulated, filtered and vacuum dried overnight to give the product as a white solid (78.6 g, 61%), m.p. 119° C.

The main peaks (in degrees 2 θ) of the PXRD pattern are as follows:

| Angle 2-Theta ° | Intensity % | Angle 2-Theta ° | Intensity % | Angle 2-Theta ° | Intensity % |
|---|---|---|---|---|---|
| 4.891 | 9.6 | 22.267 | 89.7 | 31.964 | 9.2 |
| 8.221 | 2.3 | 23.305 | 14.4 | 32.738 | 10.2 |
| 10.305 | 7.8 | 23.964 | 49.6 | 33.161 | 17.6 |
| 10.416 | 20.3 | 24.686 | 7.6 | 35.203 | 11.0 |
| 11.476 | 46.3 | 25.192 | 13.2 | 35.316 | 11.4 |
| 14.720 | 36.6 | 25.593 | 16.5 | 35.534 | 11.7 |
| 16.301 | 11.6 | 26.177 | 10.5 | 35.858 | 11.5 |
| 16.581 | 43.1 | 26.650 | 26.0 | 36.427 | 12.2 |
| 18.011 | 43.8 | 27.744 | 7.6 | 36.820 | 8.0 |
| 19.373 | 44.3 | 28.098 | 37.9 | 38.360 | 11.1 |
| 19.668 | 51.3 | 29.737 | 6.1 | 39.471 | 8.4 |
| 20.568 | 18.3 | 30.262 | 12.9 | 39.996 | 9.6 |
| 20.943 | 19.7 | 30.814 | 9.9 | 40.984 | 9.9 |
| 21.235 | 77.6 | 31.141 | 7.8 | 41.907 | 9.7 |
| 21.509 | 100.0 | 31.493 | 15.5 | 43.787 | 10.2 |

Alternatively the title compound may be prepared as follows:

Chlorosulfonic acid (706 mL) was added very slowly to a cold (−5° C. to 0° C.) solution of the title product from preparation 21 (290 g, 1.06 mol) in dichloromethane (2.9 L) The reaction mixture was stirred at 0° C. overnight. The mixture was added slowly into 3 M HCl (2.9 L) keeping the temperature between −5 and 0° C. Dichloromethane (2.9 L) was added and the layers separated. Aqueous ammonia (580 mL) was added to the dichloromethane layer at 0° C., and stirred overnight. Water was added (2 L) and the layers separated The aqueous layer was washed with dichloromethane. The dichloromethane layers were combined and concentrated under vacuum to give a brown oil which solidified on standing. The residue was purified by flash chromatography [SiO$_2$; DCM:0–6% (MeOH:NH$_3$, 9:1)] to give a pale yellow solid which was further purified by stirring in 9:1, water:acetone (1.3). The slurry was filtered, washed and dried overnight in a vacuum oven at 55° C. to give the product as a white solid (57 g, 15%), m.p. 129° C.

The main peaks (in degrees 2 θ) of the PXRD pattern are as follows

| Angle 2-Theta ° | Intensity % | Angle 2-Theta ° | Intensity % | Angle 2-Theta ° | Intensity % |
|---|---|---|---|---|---|
| 8.807 | 4.7 | 23.265 | 17.5 | 34.425 | 4.3 |
| 9.088 | 20.6 | 23.876 | 4.3 | 35.326 | 3.3 |
| 11.580 | 4.4 | 24.416 | 4.6 | 35.750 | 6.0 |
| 11.887 | 2.5 | 24.640 | 8.4 | 36.189 | 2.8 |
| 14.068 | 8.5 | 25.318 | 10.2 | 36.715 | 4.1 |

-continued

| Angle 2-Theta ° | Intensity % | Angle 2-Theta ° | Intensity % | Angle 2-Theta ° | Intensity % |
|---|---|---|---|---|---|
| 14.489 | 1.9 | 25.622 | 3.4 | 36.946 | 7.0 |
| 14.978 | 8.5 | 26.077 | 6.6 | 37.500 | 4.2 |
| 15.918 | 2.2 | 26.746 | 20.8 | 38.534 | 3.1 |
| 16.558 | 2.3 | 26.974 | 6.8 | 39.065 | 4.4 |
| 17.021 | 8.3 | 27.259 | 13.4 | 39.468 | 5.3 |
| 18.254 | 100.0 | 27.948 | 13.6 | 39.695 | 4.3 |
| 18.787 | 8.0 | 29.197 | 4.1 | 40.850 | 5.1 |
| 19.388 | 4.2 | 29.530 | 11.1 | 41.596 | 6.5 |
| 19.759 | 4.2 | 30.284 | 6.7 | 42.460 | 6.9 |
| 20.079 | 5.2 | 30.952 | 11.5 | 43.120 | 7.2 |
| 20.476 | 72.1 | 31.779 | 3.4 | 43.506 | 4.5 |
| 20.743 | 5.2 | 32.224 | 6.0 | 44.103 | 5.1 |
| 21.323 | 76.2 | 32.690 | 5.4 | 44.530 | 3.9 |
| 22.005 | 8.8 | 33.708 | 2.6 | | |

The Intermediate Sulfonyl Chloride

3-[(Dimethylamino)methyl]-4-[4-(methylsulfanyl)phenoxy]benzenesulfonyl chloride

In the above methods of preparing Example 28, the intermediate sulfonyl choride was not isolated, but was generated in situ. This is the preferred method of preparing Example 28. However, in the course of a repeat experiment, a portion of the intermediate sulfonyl choride was isolated; $^1$H NMR $\delta_H$ (d$_6$—DMSO, 300 MHz) 3.6 (3 H, br s), 4.3 (6 H, br s), 8.3 (1 H, br s), 8.6 (2 H, brs), 8.9 (2 H, brs), 9.2 (1 H, brs), 9.4 (1 H, brs). $^1$H NMR $\Delta_H$ (d6—DMSO+D$_2$O, 300 MHz) 2.4 (3 H, s), 2.8 (6 H, s), 6.8 (1 H, d), 7.1 (2 H, d), 7.4 (2 H. d), 7.7 (1 H, dd), 7.9 (1 H, s).

Salts i) L-Tartrate salt

A solution of L-tartaric acid (2.81, 18.7 mmol) in water (6 mL) was added to a hot (40° C.) solution of the title product (6.0, 17.0 mmol) in acetone (54 mL). The slurry was then heated at 60° C. for 30 min, and allowed to cool to room temperature. After stirring at room temperature for 1–2 h, the mixture was cooled to 0° C. After a further 3 h, the mixture was filtered, washed with acetone (2×10 mL), and dried in a vacuum oven at 55° C. overnight to give the desired salt as a white crystalline solid (8.4 g, 98%), m.p. 179° C.

The main peaks (in degrees 2 θ) of the PXRD pattern are as follows:

| Angle 2-Theta ° | Intensity % | Angle 2-Theta ° | Intensity % | Angle 2-Theta ° | Intensity % |
|---|---|---|---|---|---|
| 4.330 | 21.9 | 25.156 | 12.0 | 34.663 | 6.7 |
| 12.165 | 5.6 | 25.787 | 6.1 | 35.071 | 5.6 |
| 12.425 | 10.1 | 26.057 | 12.4 | 35.674 | 15.2 |
| 12.543 | 5.4 | 26.114 | 14.5 | 35.788 | 14.7 |
| 13.218 | 12.7 | 26.408 | 11.6 | 36.228 | 10.7 |
| 14.368 | 6.3 | 26.642 | 25.5 | 36.517 | 8.6 |
| 14.463 | 6.3 | 26.830 | 25.4 | 36.975 | 13.3 |
| 16.849 | 7.3 | 27.130 | 26.7 | 37.618 | 17.4 |
| 17.149 | 57.2 | 27.540 | 12.6 | 37.799 | 19.7 |
| 17.469 | 49.5 | 28.001 | 20.7 | 38.242 | 16.2 |
| 17.623 | 66.1 | 29.122 | 17.7 | 38.882 | 15.5 |
| 18.498 | 9.5 | 29.772 | 28.7 | 39.432 | 8.1 |
| 19.403 | 47.2 | 30.394 | 13.5 | 39.577 | 9.0 |
| 20.422 | 12.4 | 30.983 | 12.8 | 40.198 | 18.4 |
| 20.733 | 15.7 | 31.259 | 32.9 | 41.451 | 8.2 |
| 20.923 | 28.2 | 32.085 | 14.6 | 42.109 | 14.6 |
| 21.914 | 100.0 | 32.258 | 9.5 | 42.816 | 8.7 |
| 23.542 | 19.0 | 32.818 | 5.2 | 43.969 | 11.5 |
| 23.776 | 20.0 | 33.433 | 6.5 | 44.213 | 14.2 |
| 24.958 | 30.8 | 34.085 | 20.3 | | 11.9 | ii) D-Tartrate salt

A solution of D-tartaric acid (2.81 g, 18.7 mmol) in water (6 mL) was added to a hot (40° C.) solution of the title compound (6.0, 17.0 mmol) in acetone (54 mL). The slurry was then heated at 60° C. for 30 min, and allowed to cool to room temperature. After stirring at room temperature for 1–2 h, the mixture was cooled to 0° C. After a further 3 h, the mixture was filtered, washed with acetone (2×10 mL), and dried in a vacuum oven at 55° C. overnight to give the desired salt as a white crystalline solid (8.4 g, 98%), m.p. 182° C.

The main peaks (in degrees 2 θ) of the PXRD pattern are as follows:

| Angle 2-Theta ° | Intensity % | Angle 2-Theta ° | Intensity % | Angle 2-Theta ° | Intensity % |
|---|---|---|---|---|---|
| 4.320 | 23.3 | 25.153 | 11.8 | 34.701 | 5.1 |
| 12.147 | 5.0 | 25.776 | 5.4 | 35.066 | 4.9 |
| 12.414 | 11.1 | 26.058 | 7.2 | 35.693 | 13.8 |
| 12.539 | 4.8 | 26.135 | 11.8 | 35.794 | 11.5 |
| 13.219 | 11.9 | 26.405 | 10.1 | 36.241 | 11.5 |
| 14.368 | 5.8 | 26.635 | 25.4 | 36.525 | 8.5 |
| 14.480 | 6.0 | 26.825 | 24.3 | 37.044 | 8.8 |
| 16.854 | 7.0 | 27.133 | 27.8 | 37.632 | 15.2 |
| 17.161 | 58.2 | 27.547 | 13.3 | 37.806 | 18.8 |
| 17.452 | 52.8 | 28.005 | 19.1 | 38.264 | 15.3 |
| 17.631 | 68.8 | 29.125 | 18.2 | 38.880 | 14.1 |
| 18.516 | 8.5 | 29.788 | 26.8 | 39.454 | 9.1 |
| 19.407 | 50.3 | 30.408 | 12.2 | 39.542 | 8.4 |
| 20.425 | 12.3 | 30.984 | 10.2 | 40.193 | 17.2 |
| 20.733 | 17.0 | 31.273 | 26.4 | 41.530 | 5.8 |
| 20.912 | 26.5 | 32.093 | 12.5 | 42.108 | 12.1 |
| 21.919 | 100.0 | 32.268 | 7.5 | 42.854 | 5.2 |
| 23.566 | 20.2 | 32.821 | 4.8 | 43.930 | 7.9 |
| 23.787 | 17.5 | 33.461 | 5.4 | 44.243 | 11.7 |
| 24.974 | 32.1 | 34.084 | 17.3 | | | iii) Hydrochloride Salts a) Lower melting point form

A solution of hydrochloric acid /isopropanol (7.02 M, 0.41 mL, 2.86 mmol) was added to a solution of the title compound (1.0 g, 2.84 mmol) in methyl ethyl ketone (10 mL). After stirring at room temperature for 3 h the mixture was filtered, washed and dried in a vacuum oven at 55° C. overnight to give the desired salt, m.p. 176° C.

The main peaks (in degrees 2 θ) of the PXRD pattern are as follows:

| Angle 2-Theta ° | Intensity % | Angle 2-Theta ° | Intensity % | Angle 2-Theta ° | Intensity % |
|---|---|---|---|---|---|
| 4.365 | 10.4 | 18.749 | 23.5 | 25.485 | 37.9 |
| 8.758 | 22.3 | 19.031 | 42.1 | 26.443 | 40.8 |
| 11.591 | 19.0 | 19.374 | 20.8 | 26.634 | 36.1 |
| 13.184 | 10.0 | 20.096 | 47.2 | 27.345 | 13.4 |
| 14.438 | 20.5 | 20.904 | 15.0 | 27.846 | 34.0 |
| 14.522 | 14.2 | 21.408 | 20.4 | 29.280 | 17.9 |

-continued

| Angle 2-Theta | Intensity % | Angle 2-Theta | Intensity % | Angle 2-Theta | Intensity % |
|---|---|---|---|---|---|
| 14.948 | 10.6 | 21.710 | 74.1 | 30.117 | 13.9 |
| 15.512 | 18.7 | 22.012 | 100.0 | 31.281 | 21.4 |
| 15.886 | 9.7 | 22.157 | 42.7 | 33.336 | 16.5 |
| 16.716 | 23.7 | 22.485 | 27.9 | 34.024 | 11.0 |
| 16.975 | 36.5 | 22.614 | 31.6 | 35.172 | 16.2 |
| 17.568 | 22.3 | 23.967 | 11.9 | 37.237 | 14.6 |
| 18.506 | 16.4 | 24.503 | 19.6 |  | 11.4 | b) Higher melting point form

A solution of hydrochloric acid /isopropanol (7.02 M, 0.41 mL, 2.86 mmol) was added to a solution of the title compound (1.0 g, 2.84 mmol) in methyl ethyl ketone (10 mL). After stirring at room temperature for 7 h the mixture was filtered, washed and dried in a vacuum oven at 55° C. overnight to give the desired salt, m.p. 192° C.

The main peaks (in degrees 2 θ) of the PXRD pattern are as follows:

| Angle 2-Theta | Intensity % | Angle 2-Theta | Intensity % | Angle 2-Theta | Intensity % |
|---|---|---|---|---|---|
| 6.511 | 1.5 | 23.777 | 8.7 | 33.939 | 10.0 |
| 10.198 | 2.6 | 24.218 | 19.1 | 34.326 | 6.5 |
| 11.969 | 2.9 | 24.288 | 24.1 | 35.190 | 6.6 |
| 12.081 | 6.0 | 25.086 | 20.8 | 36.183 | 6.9 |
| 12.500 | 2.1 | 25.973 | 6.2 | 36.674 | 5.9 |
| 12.948 | 17.7 | 26.342 | 13.0 | 37.061 | 4.8 |
| 14.111 | 2.6 | 26.825 | 13.8 | 37.365 | 4.3 |
| 15.313 | 4.9 | 27.357 | 8.2 | 37.918 | 3.9 |
| 16.477 | 13.2 | 27.600 | 5.7 | 38.491 | 7.4 |
| 16.587 | 15.0 | 27.942 | 5.2 | 38.680 | 5.6 |
| 17.261 | 3.8 | 28.322 | 20.0 | 39.283 | 2.9 |
| 18.009 | 22.0 | 28.895 | 13.7 | 39.915 | 3.9 |
| 19.104 | 15.6 | 30.097 | 9.2 | 40.271 | 6.8 |
| 20.174 | 100.0 | 30.192 | 10.2 | 40.686 | 7.4 |
| 21.435 | 11.7 | 30.567 | 11.1 | 41.448 | 4.9 |
| 21.961 | 26.1 | 31.493 | 7.3 | 42.435 | 5.3 |
| 22.554 | 4.7 | 31.776 | 4.8 | 43.170 | 4.3 |
| 22.860 | 21.3 | 32.417 | 17.4 | 43.612 | 11.1 |
| 23.059 | 11.2 | 32.931 | 5.5 |  | 12.1 |
| 23.126 | 13.5 | 33.516 | 7.5 | 44.077 | 5.8 |
| 23.425 | 17.0 |  |  |  |  | iv) Citrate Salt

Citric acid (0.30 g, 1.56 mmol) was added to a solution of the title compound (0.50 g, 1.42 mmol) in acetone (5 mL). After stirring at room temperature for 3 h the mixture was filtered, washed and dried in a vacuum oven at 55° C. overnight to give the desired salt, m.p. 110° C.

The main peaks (in degrees 2 θ) of the PXRD pattern are as follows:

| Angle 2-Theta | Intensity % | Angle 2-Theta | Intensity % | Angle 2-Theta | Intensity % |
|---|---|---|---|---|---|
| 5.516 | 11.7 | 17.246 | 39.6 | 23.513 | 48.2 |
| 5.731 | 25.7 | 17.307 | 44.3 | 24.114 | 39.9 |
| 7.279 | 7.7 | 17.587 | 52.4 | 24.737 | 50.0 |
| 9.057 | 8.2 | 18.186 | 44.3 | 25.403 | 38.8 |
| 10.733 | 25.1 | 19.089 | 100.0 | 25.986 | 37.5 |
| 11.522 | 15.3 | 19.596 | 51.9 | 26.182 | 42.2 |
| 11.957 | 13.8 | 19.815 | 68.6 | 27.333 | 23.8 |
| 13.115 | 11.2 | 20.286 | 56.9 | 30.030 | 31.2 |
| 13.429 | 12.2 | 20.553 | 81.1 | 30.250 | 40.4 |
| 14.311 | 13.3 | 20.713 | 63.0 | 30.396 | 39.5 |
| 14.702 | 23.6 | 21.342 | 34.4 | 31.830 | 24.5 |
| 16.515 | 17.8 | 21.666 | 42.6 | 34.066 | 27.4 |
| 16.813 | 17.6 | 21.830 | 51.1 | 37.320 | 23.2 | v) Sulfate Salt

Concentrated sulfuric acid (0.04 mL) was added to a solution of the title compound (0.50 g, 1.42 mmol) in acetone (5 mL). After stirring at room temperature for 2 h, the mixture was stirred at 0° C. for a further 3 h. The mixture was then filtered, washed and dried overnight in a vacuum oven at 55° C. to give the desired salt as a white solid (0.31 g, 48%), m.p. 233° C.

The main peaks (in degrees 2θ) of the PXRD pattern are as follows:

| Angle 2-Theta ° | Intensity % | Angle 2-Theta ° | Intensity % | Angle 2-Theta ° | Intensity % |
|---|---|---|---|---|---|
| 4.770 | 7.1 | 21.291 | 9.5 | 29.923 | 15.5 |
| 9.354 | 10.5 | 21.610 | 45.1 | 31.761 | 10.5 |
| 9.906 | 8.0 | 22.019 | 11.0 | 32.221 | 8.3 |
| 12.435 | 6.2 | 22.611 | 52.2 | 32.690 | 9.0 |
| 14.406 | 12.9 | 23.168 | 12.2 | 33.983 | 9.3 |
| 16.040 | 8.2 | 23.567 | 39.0 | 34.610 | 10.2 |
| 16.563 | 3.4 | 23.855 | 16.6 | 35.098 | 11.2 |
| 17.145 | 26.5 | 24.096 | 12.7 | 35.420 | 16.7 |
| 17.322 | 48.9 | 24.521 | 33.7 | 36.212 | 9.4 |
| 17.945 | 7.3 | 24.951 | 53.7 | 36.942 | 14.4 |
| 18.292 | 35.2 | 25.341 | 9.7 | 37.618 | 9.6 |
| 18.794 | 100.0 | 25.790 | 13.6 | 38.349 | 9.9 |
| 19.234 | 7.1 | 26.276 | 13.5 | 38.856 | 11.6 |
| 19.780 | 46.3 | 26.815 | 12.8 | 39.126 | 8.3 |
| 20.026 | 50.0 | 28.030 | 22.5 | 40.321 | 10.0 |
| 20.365 | 10.9 | 28.739 | 21.7 | 40.948 | 12.5 |
| 20.513 | 11.6 | 29.274 | 8.8 |  | 7.5 | vi) Phosphate Salt

Phosphoric acid (4.63 mL, 67.7 mmol) was added dropwise to a suspension of the title compound (21.7 g, 61.6 mmol) in water (149 mL). The slurry was then heated on a steam bath until a clear solution was produced. This solution was then allowed to cool to room temperature and stirred for 2 h. The mixture was then cooled to 0° C., and stirred for a further 3 h. The precipitate was filtered, washed with water (2×50 mL) and dried in a vacuum oven at 55° C. overnight to give the desired salt as a white crystalline solid (23.1 g, 83%), m.p. 196° C.

The main peaks (in degrees 2 θ) of the PXRD are as follows:

| Angle 2-Theta ° | Intensity % | Angle 2-Theta ° | Intensity % | Angle 2-Theta ° | Intensity % |
|---|---|---|---|---|---|
| 4.336 | 18.7 | 22.157 | 13.9 | 31.877 | 5.7 |
| 11.698 | 8.5 | 22.729 | 22.5 | 32.521 | 13.0 |
| 13.047 | 14.5 | 23.034 | 16.2 | 32.702 | 6.9 |
| 13.479 | 9.4 | 23.219 | 17.3 | 33.213 | 7.2 |
| 14.330 | 13.5 | 23.506 | 79.0 | 33.960 | 8.9 |
| 15.217 | 69.4 | 23.915 | 11.9 | 34.334 | 10.5 |
| 15.440 | 10.6 | 25.456 | 17.3 | 34.717 | 22.6 |
| 16.205 | 12.4 | 25.691 | 27.0 | 35.586 | 10.7 |
| 17.440 | 70.9 | 26.317 | 12.5 | 36.184 | 16.7 |

-continued

| Angle 2-Theta ° | Intensity % | Angle 2-Theta ° | Intensity % | Angle 2-Theta ° | Intensity % |
|---|---|---|---|---|---|
| 17.899 | 5.4 | 26.508 | 21.9 | 36.722 | 6.8 |
| 18.300 | 30.6 | 26.838 | 14.9 | 37.819 | 6.4 |
| 18.750 | 22.5 | 26.976 | 25.5 | 38.412 | 8.7 |
| 19.120 | 12.6 | 27.115 | 22.6 | 38.773 | 13.3 |
| 19.740 | 100.0 | 27.971 | 32.6 | 39.078 | 9.5 |
| 19.930 | 30.8 | 28.902 | 12.5 | 39.848 | 11.5 |
| 20.291 | 15.6 | 29.351 | 8.6 | 40.076 | 10.7 |
| 20.581 | 58.2 | 29.987 | 22.1 | 41.269 | 9.9 |
| 21.617 | 39.9 | 31.022 | 8.0 | 43.921 | 12.8 |
| 21.832 | 10.4 | 31.368 | 11.6 | | 9.8 |

EXAMPLES 29–60

The following sulfonamides were prepared in an analogous fashion to that described herein for Example 28, replacing ammonia with the requisite amine where appropriate.

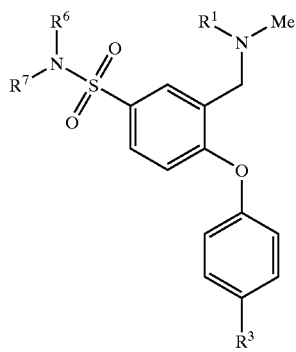

| Example | Starting Material | $R^6$ | $R^7$ | $R^1$ | $R^3$ | Data |
|---|---|---|---|---|---|---|
| 29 | Prep 27 | Me | Me | H | $CF_3$ | $\delta_H$(CDCl$_3$, 400MHz) 2.45 (3H, s), 2.75(6H, s), 3.85 (2H, s), 6.96(1H, d), 7.07(2H, d), 7.64(3H, d), 7.88(1H, s); MSm/z (ES$^+$)389(MH$^+$). |
| 30 | Prep 22 | Me | H | Me | $CF_3$ | $\delta_H$(CDCl$_3$, 400MHz)2.59 (2H, s), 2.97(3H, s), 4.58 (1H, s), 4.81(6H, s), 7.08 (1H, d), 7.40(2H, d), 7.80(2H, d), 7.92(1H, d), 8.15(1H, s) |
| 31 | Prep 22 | HO~~~~ | H | Me | $CF_3$ | $\delta_H$(CDCl$_3$, 300MHz)2.31 (6H, s), 3.18(2H, t), 3.56 (2H, s), 3.68(2H, t), 6.97 (1H, d), 7.06(2H, d), 7.63(2H, d), 7.78(1H, d), 8.12(1H, s); MSm/z (TS$^+$) 419(MH$^+$) |
| 32 | Prep 22 | Me | Me | Me | $CF_3$ | $\delta_H$(CDCl$_3$, 300MHz) 2.77 (6H, s), 2.83(6H, s), 4.20 (2H, s), 6.96(1H, d), 7.22(2H, d), 7.71(2H, d), 7.78(1H, d), 8.18 (1H, s); MSm/z(TS$^+$) 403(MH$^+$). |
| 33 | Prep 22 | H | H | Me | $CF_3$ | $\delta_H$(CDCl$_3$, 300MHz)2.28 (6H, s), 3.54(2H, s), 6.98 (1H, d), 7.04(2H, d), 7.61(2H, d), 7.80(1H, d), 8.16(1H, s); MSm/z (TS$^+$) 375(MH$^+$). |
| 34 | Prep 27 | Me | H | H | $CF_3$ | $\delta_H$(CDCl$_3$, 300MHz)2.44 (3H, s), 2.68(3H, s), 3.84 (2H, s), 6.94(1H, d), 7.08(2H, d), 7.62(2H, |

-continued

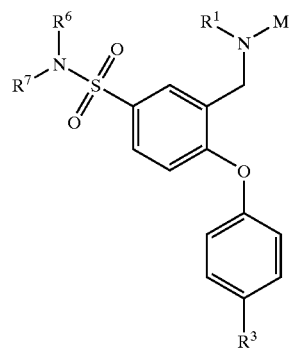

| Example | Starting Material | R⁶ | R⁷ | R¹ | R³ | Data |
|---|---|---|---|---|---|---|
| 35 | Prep 26 | H | | H | H | —OCF₃ | d), 7.76(1H, d), 8.00 (1H, s), MSm/z(TS⁺) 375(MH⁺). $\delta_H$(CDCl₃, 300MHz) 2.48(3H, s), 2.65(3H, br), 3.89(2H, s), 6.84 (1H, d), 7.03(2H, m), 7.23(2H, m), 7.77(1H, dd), 8.03(1H, d); MSm/z (TS⁺)377(MH⁺). |
| 36 (HCl salt) | Prep 23 | H | H | Me | —OCF₃ | $\delta_H$(d₆-DMSO, 300MHz) 2.80(6H, s), 4.43(2H, s), 6.98(1H, d), 7.37(4H, m), 7.50(2H, m), 7.86 (1H, dd), 8.13(1H, d), 10.18(1H, br); MSm/z (TS⁺)391(MH⁺). |
| 37 | Prep 23 | Me | H | Me | OCF₃ | $\delta_H$(d₆-DMSO, 300MHz) 2.43(3H, d), 2.80(6H, s), 4.46(2H, s), 6.99(1H, d), 7.37(2H, m), 7.48 (3H, m), 7.80(1H, dd), 8.12(1H, d), 10.37(1H, br); MSm/z(TS⁺)405 (MH⁺) |
| 38 (HCl salt) | Prep 28 | HO⁀ | H | H | SMe | $\delta_H$(DMSO-D₆, 400MHz) 2.47(3H, s), 2.63(3H, s), 2.79(2H, q), 3.36(2H, m), 4.29(2H, s), 4.71 (1H, t), 6.86(1H, d), 7.17 (2H, d), 7.38(2H, d), 7.60(1H, t), 7.75(1H, dd), 8.01(1H, d), 8.95 (2H, br); MSm/z(ES⁺) 383(MH⁺). |
| 39 (HCl salt) | Prep 28 | HO⁀ | Me | H | SMe | $\delta_H$(DMSO-D₆, 400MHz) 2.48(3H, s), 2.61(3H, s), 2.72(3H, s), 3.00(2H, t), 3.49(2H, m), 4.29(2H, s), 4.83(1H, t), 6.83(1H, d), 7.21(2H, d), 7.38 (2H, d), 7.71(1H, dd), 8.03(1H, d), 9.37(2H, br), MSm/z(ES⁺) 397 (MH⁺) |
| 40 (HCl salt) | Prep 28 | HO⁀⁀ | H | H | SMe | $\delta_H$(DMSO-D₆, 400MHz) 1.51(2H, m), 2.48(3H, s), 2.61(3H, s), 2.79(2H, m), 3.35(2H, m), 4.28 (2H, s), 4.44(1H, br), 6.85(1H, d), 7.19(2H, d), 7.37(2H, d), 7.53 (1H, t), 7.74(1H, dd), 8.02(1H, d), 9.11(2H, br); MSm/z(ES⁺) 397 (MH⁺). |

-continued

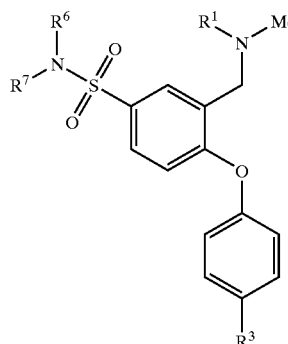

| Example | Starting Material | R⁶ | R⁷ | R¹ | R³ | Data |
|---|---|---|---|---|---|---|
| 41 | Prep 28 | HO-CH(Me)- (R) | H | H | SMe | δ_H(CD₃OD, 300MHz) 1.00(3H, d), 2.43(3H, s), 2.48(3H, s), 3.26–3.34(2H, m), 3.38–3.46 (1H, m), 3.89(2H, s), 6.87(1H, d), 7.04(2H, d), 7.35(2H, d), 7.72 (1H, dd), 7.92(1H, d); MSm/z(ES⁺) 397(MH⁺). |
| 42 (HCl salt) | Prep 28 | H | H | H | SMe | δ_H(CDCl₃, 400MHz)2.49 (6H, s), 3.89(2H, s), 6.81 (1H, d), 6.96(2H, d), 7.29(2H, d), 7.72(1H, dd), 7.99(1H, d); MSm/z (TS⁺)339(MH⁺). |
| 43 | Prep 28 | Me | H | H | SMe | δ_H(CDCl₃, 400MHz) 2.49 (3H, s), 2.50(3H, s), 2.65 (3H, s), 3.90(2H, s), 6.82 (1H, d), 6.97(2H, d), 7.30(2H, d), 7.66(1H, dd), 7.91(1H, d); MSm/z (TS⁺)353(MH⁺). |
| 44 (HCl salt) | Prep 28 | Me | Me | H | SMe | δ_H(CD₃OD, 400MHz) 2.49(3H, s), 2.70(6H, s), 2.83(3H, s), 4.45(2H, s), 6.86(1H, d), 7.16(2H, d), 7.41(2H, d), 7.78 (1H, dd), 7.98(1H, d); MSm/z(TS⁺)367(MH⁺). |
| 45 (HCl salt) | Prep 21 | Me | H | Me | SMe | δ_H(CD₃OD, 400MHz) 2.51(3H, s), 2.55(3H, s), 2.97(6H, s), 4.57(2H, s), 6.96(1H, d), 7.17(2H, d), 7.41(2H, d), 7.86 (1H, dd), 8.06(1H, d); MSm/z(ES⁺)368(MH⁺). |
| 46 (HCl salt) | Prep 21 | CH(OH)CH(Me)- | H | Me | SMe | δ_H(CD₃OD, 400MHz) 1.15(3H, d), 2.52(3H, s), 2.84(2H, m), 3.00 (6H, s), 3.76(1H, m), 4.56(2H, s), 6.95(1H, d), 7.16(2H, d), 7.40 (2H, d), 7.89(1H, dd), 8.06(1H, d); MSm/z (ES⁺) 412(MH⁺). |
| 47 (HCl salt) | Prep 21 | HOCH₂CH₂- | Me | Me | SMe | δ_H(CD₃OD, 400MHz) 2.51(3H, s), 2.84(3H, s), 2.97(6H, s), 3.17(2H, t), 3.68(2H, t), 4.57(2H, s), 6.97(1H, d), 7.17(2H, d), 7.40(2H, d), 7.85 (1H, dd), 8.06(1H, d); MSm/z(ES⁺) 412(MH⁺). |

-continued

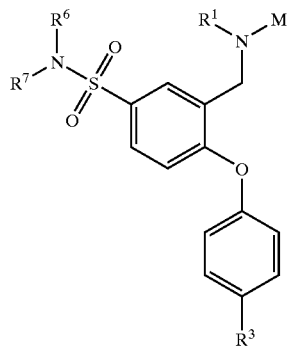

| Example | Starting Material | R⁶ | R⁷ | R¹ | R³ | Data |
|---|---|---|---|---|---|---|
| 48 (HCl salt) | Prep 21 | MeO~~~~ | H | Me | SMe | δ_H(CD₃OD, 400MHz) 2.51(3H, s), 2.96(6H, s), 3.06(2H, t)(, 3.25(3H, s), 3.39(2H, t), 4.55(2H, s), 6.95(1H, d), 7.16(2H, d), 7.40(2H, d), 7.89 (1H, d), 8.06(1H, d); MSm/z(ES⁺) 412(MH⁺). |
| 49 (HCl salt) | Prep 21 | HO-CH(Me)- | H | Me | SMe | δ_H(CD₃OD, 400MHz) 1.02(3H, d), 2.51(3H, s), 2.96(6H, s), 3.30(3H, m), 4.55(2H, s), 6.94 (1H, d), 7.16(2H, d), 7.40(2H, d), 7.90(1H, dd), 8.09(1H, d); MSm/z (ES⁺) 412(MH⁺). |
| 50 (HCl salt) | Prep 21 | Et | H | Me | SMe | δ_H(CD₃OD, 400MHz) 1.08(3H, t), 2.51(3H, s), 2.91(2H, q), 2.97(3H, s), 4.56(2H, s), 6.95(1H, d), 7.16(2H, d), 7.40 (2H, d), 7.87(1H, dd), 8.06(1H, d); MSm/z (ES⁺)382(MH⁺). |
| 51 (HCl salt) | Prep 21 | cyclopropyl-CH₂- | H | Me | SMe | δ_H(CD₃OD, 400MHz) 0.11(2H, m), 0.44(2H, m), 0.86(1H, m), 2.51 (3H, s), 2.76(2H, d), 2.96(6H, s), 4.56(2H, s), 6.94(1H, d), 7.16(2H, d), 7.40(2H, d), 7.88 (1H, dd), 8.06(1H, d); MSm/z(ES⁺) 408(MH⁺). |
| 52 (HCl salt) | Prep 21 | 1-(hydroxymethyl)cyclopentyl | H | Me | SMe | δ_H(CD₃OD, 400MHz) 1.15–1.63(6H, m), 1.81 (2H, m)(, 2.51(3H, s), 2.96(6H, s), 3.50(2H, s), 4.55(2H, s), 6.93(1H, d), 7.15(2H, d), 7.39 (2H, d), 7.93(1H, dd), 8.09(1H, d); MSm/z (ES⁺) 452(MH⁺). |
| 53 | Prep 21 | HO-CH₂-CH(Me)- | H | Me | SMe | δ_H(CDCl₃, 400MHz) 1.10 (3H, d), 2.31(6H, s), 2.50(3H, s), 3.37(2H, m), 3.49(1H, m), 3.60 (2H, s), 4.78(1H, br), 6.84(1H, d), 6.94(2H, d), 7.29(2H, d), 7.70 (1H, dd), 8.05(1H, s), MSm/z(TS⁺) 411(MH⁺) |
| 54 (HCl salt) | Prep 21 | —CH₂CH₂CH₂— | | Me | SMe | δ_H(CDCl₃, 400MHz) 2.11 (2H, m), 2.51(3H, s), |

-continued

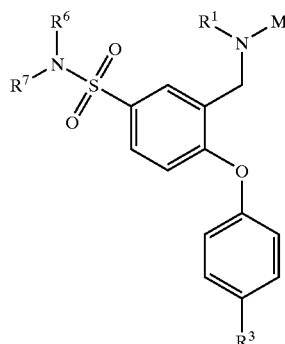

| Example | Starting Material | R⁶ | R⁷ | R¹ | R³ | Data |
|---|---|---|---|---|---|---|
| | | | | | | 2.98(6H, s), 3.58(1H, m), 3.79(3H, t), 4.60 (2H, s), 7.02(1H, d), 7.18(2H, d), 7.41(2H, d), 7.88(1H, d), 8.07 (1H, s); MSm/z(T⁺) 393(MH⁺) |
| 55 | Prep 21 | H₂N-C(=O)-CH₂- | H | Me | SMe | $\delta_H$(CDCl₃, 400MHz) 2.32 (6H, s), 2.48(3H, s), 3.30 (2H, s), 3.52(2H, s), 3.68 (2H, s), 6.88(1H, d), 7.03(2H, d), 7.35(2H, d), 7.72(1H, d), 7.93 (1H, s); MSm/z(ES⁺) 410(M⁺) |
| 56 | Prep 21 | CH₃CH(OH)CH₂- | H | Me | SMe | $\delta_H$(CDCl₃, 400MHz) 1.15 (3H, d), 2.31(6H, s), 2.49(3H, s), 2.80(1H, dd), 3.09(1H, d), 3.23 (1H, t), 3.59(2H, s), 3.85 (1H, m), 5.16(1H, br), 6.82(1H, d), 6.95(2H, d), 7.29(2H, d), 7.66 (1H, d), 8.02(1H, s); MS m/z(ES⁺) 413(MH⁺) |
| 57 (HCl salt) | Prep 21 | HO-(CH₂)₃- | H | Me | SMe | $\delta_H$(CD₃OD, 400MHz) 1.66 (2H, m), 2.51(3H, s), 2.97(6H, m), 3.30(1H, s), 3.57(2H, t), 4.57(2H, s), 6.95(1H, d), 7.16(2h, d), 7.39(2H, d), 7.87 (1H, dd), 8.08(1H, s); MSm/z(ES⁺) 411(MH⁺) |
| 58 (HCl salt) | Prep 21 | HO-CH₂CH₂- | H | Me | SMe | $\delta_H$(CD₃OD, 400MHz) 2.51 (3H, s), 2.96(6H, s), 3.00 (2H, t), 4.56(2H, t), 4.97 (2H, s), 6.94(1H, d), 7.16 (2H, d), 7.40(2H, d), 7.88(1H, dd), 8.09 1H, s); MSm/z(ES⁺) 411 (MH⁺) |
| 59 (HCl salt) | Prep 21 | Me | Me | Me | SMe | $\delta_H$(CD₃OD, 400MHz) 2.51 (3H, s), 2.72(6H, s), 2.96 (6H, s), 4.57(2H, s), 6.99 (1H, d), 7.17(2H, d), 7.40(2H, d), 7.83(1H, dd), 8.02(1H, s); MSm/z (ES⁺)381(M⁺) |
| 60 (HCl salt) | Prep 29 | H | H | Me | SEt | $\delta_H$(d₆-DMSO, 400MHz) 1.22(3H, t), 2.78(6H, s), 2.97(2H, q), 4.42(2H, s), 6.91(1H, d), 7.17 (2H, d), 7.39(2H, d), 7.42(2H, d), 7.83(1H, |

-continued

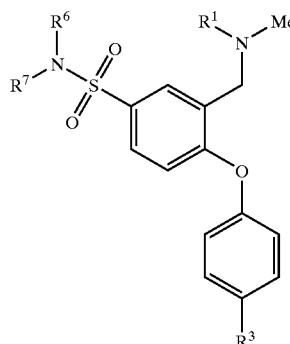

| Example | Starting Material | R⁶ | R⁷ | R¹ | R³ | Data |
|---|---|---|---|---|---|---|
| | | | | | | dd), 8.07(1H, s); MSm/z (ES⁺)367(MH⁺) |

EXAMPLE 61

4-[4-Methoxy-3-(methylsulfanyl)phenoxy]-3-[(methylamino)methyl]-benzenesulfonamide

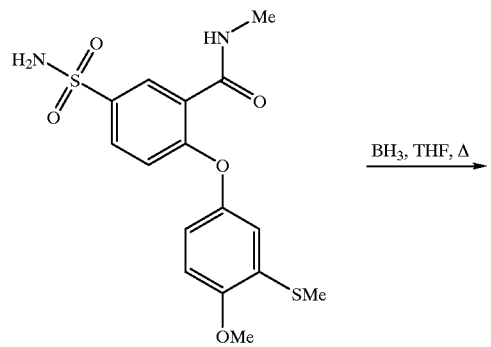

Borane-tetrahydrofuran complex (1 M in THF, 10 mL, 10 mmol) was added dropwise to the amide from preparation 32 (450 mg, 1.18 mmol). The mixture was then stirred at reflux for 4 hours. After cooling to room temperature the reaction was quenched by the addition of methanol (10 mL) and the mixture evaporated to a white foam. This residue was treated with hydrochloric acid (6 M, 10 mL) and the mixture heated to reflux once more for 1 hour. After cooling to room temperature the mixture was neutralised to pH ca. 7 by treatment with excess sodium hydroxide (2 M) and then saturated aqueous ammonium chloride. The mixture was then extracted with ethyl acetate (3×50 mL), DCM (2×50 mL) and the combined organics were dried (MgSO₄) and evaporated to a colourless oil. This oil was redissolved in ethyl acetate (20 mL) and treated with 1 M hydrochloric acid in diethyl ether (2 mL, 2 mmol) to form the hydrochoride salt which was collected by filtration and dried (346 mg, 73%); $\delta_H$ (CD₃OD, 400 MHz) 2.34 (3 H, s), 2.78 (3 H, s), 3.86 (3 H, s), 4.39 (2 H, s) 6.83 (1 H, d), 6.90 (1 H, m), 6.98 (2 H, m), 7.84 (1 H, dd), 8.01 (1 H, d); MS m/z (ES⁺) 369 (MH⁺).

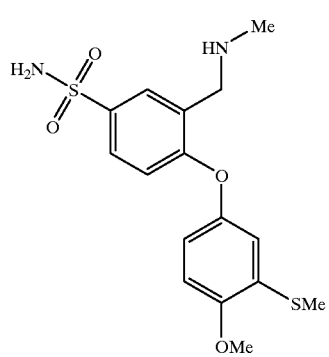

EXAMPLES 62–63

The following sulfonamides were prepared in an analogous fashion to that in Example 61 starting from the appropriate amide.

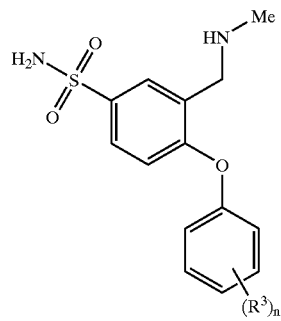

| Example | Starting Material | $(R^3)_n$ | Data |
|---|---|---|---|
| 62 (HCl salt) | Prep 30 | 3-OMe 4-SMe | (248 mg, 43%); $\delta_H$(DMSO-D$_6$, 400MHz)2.35(3H, s), 2.60(3H, s), 3.76(3H, s), 4.24(2H, s), 6.75(1H, dd), 6.84(1H, d), 6.90(1H, d), 7.19(1H, d), 7.31(2H, s), 7.77(1H, d), 8.00(1H, s), 9.10(2H, br); MSm/z(TS$^+$) 369(MH$^+$). |
| 63 (HCl salt) | Prep 33 | 3-CF$_3$ 4-SMe | HCl salt: $\delta_H$(d$_6$-DMSO, 400MHz)2.38(3H, s), 3.08(3H, s), 4.50(2H, s), 6.87(1H, d), 6.97(2H, d), 7.11(2H, brs), 7.43(2H, d), 7.58(1H, d); MSm/z(ES$^+$)407(MH$^+$) |

The sulfonamide of example 42 can also be prepared using this method starting from the amide of preparation 31.

EXAMPLES 64–65

The following tertiary amine sulfonamides were prepared via reductive methylation using the method described for Example 178 and the appropriate secondary amine as starting material.

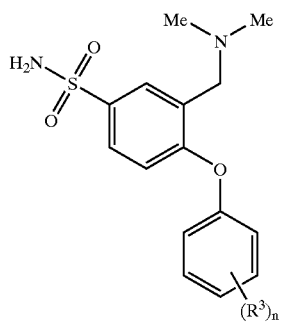

| Example | Starting Material | $(R^3)_n$ | $^1$H NMR Data |
|---|---|---|---|
| 64 | Example 62 | 3-OMe 4-SMe | $\delta_H$(CDCl$_3$, 400MHz)2.27(6H, s), 2.40(3H, s), 3.55 (2H, s), 3.82(3H, s), 6.53(2H, m), 6.84(1H, d), 7.13 (1H, d), 7.70(1H, dd), 8.04(1H, d); MSm/z(ES$^+$)383 (MH$^+$). |
| 65 (HCl salt) | Example 61 | 3-SMe 4-OMe | $\delta_H$(CD$_3$OD, 400MHz)2.38(3H, s), 2.96(6H, s), 3.89 (3H, s), 4.51(2H, s), 6.92(2H, m), 7.01(2H, m), 7.94 (1H, d), 8.05(1H, s); MSm/z(TS$^+$)383(MH$^+$). |

The product of example 28 can also be prepared by this method from the secondary amine of example 42.

EXAMPLE 66

N-Acetyl-3-[(dimethylamino)methyl]-4-[4-(methylsulfanyl)phenoxy]-benzenesulfonamide

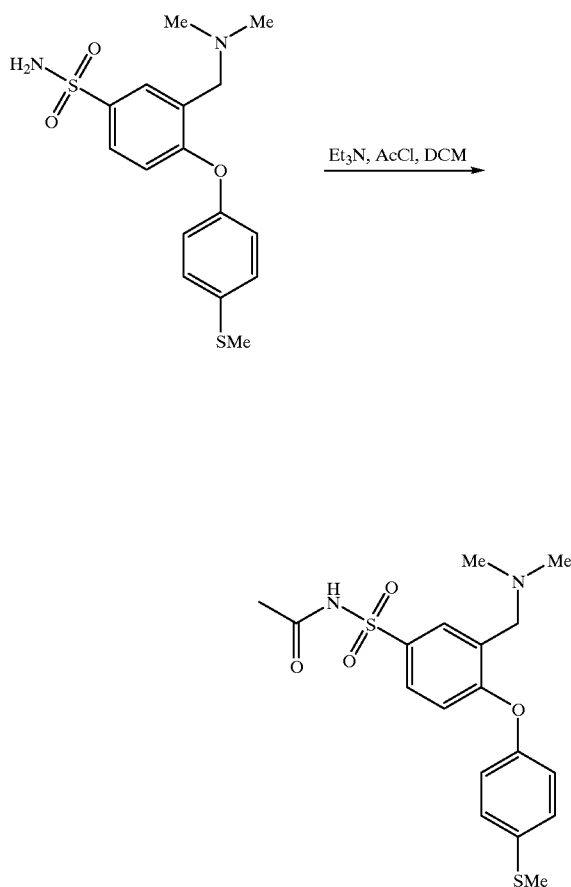

Triethylamine (399 μL, 2.86 mmol) was added to a solution of the sulfonamide from example 28 (500 mg, 1.3 mmol) in DCM (5 mL) followed by acetyl chloride (102 μL, 1.43 mmol). The mixture was stirred at room temperature for 16 h and then the solvent was removed in vacuo. The residue was purified by column chromatography [SiO$_2$, DCM 100% increasing polarity to 15% (1:7 NH$_4$OH:MeOH) in DCM] to give a crystalline solid (438 mg, 86%); δ$_H$ (DMSO-D$_6$, 400 MHz) 1.83 (3 H, s), 2.31 (6 H, s), 2.46 (3 H, s), 3.68 (2 H, s), 6.83 (1 H, d), 7.03 (2 H, d), 7.32 (2 H, d), 7.71 (1 H, d), 7.99 (1 H, s); MS m/z (ES$^+$) 395 (MH$^+$).

EXAMPLE 67

(E)-2-{3-[(Dimethylamino)methyl]-4-[4-(methylsulfanyl)phenoxy]phenyl}-ethenesulfonamide

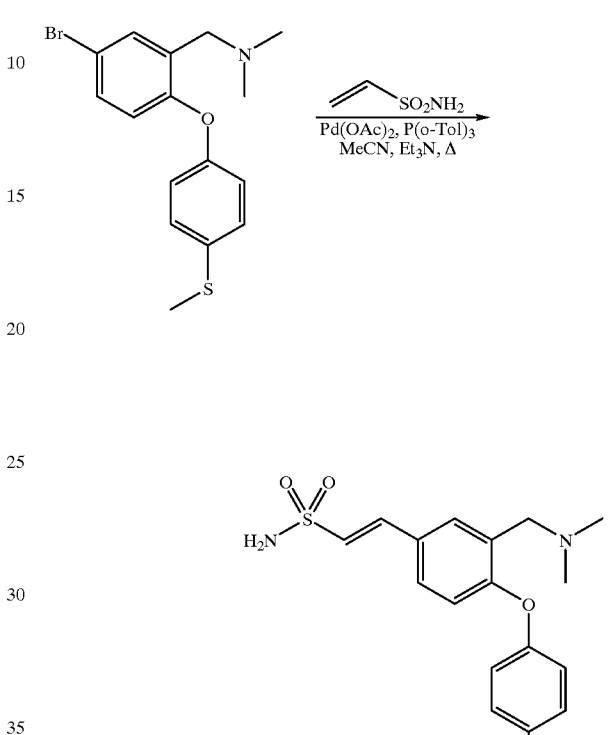

The bromide from Example 9 (2.0 g, 5.68 mmol), vinyl-sulfonamide (1.22 g, 11.35 mmol), palladium acetate (64 mg, 0.28 mmol, 5 mol%), tri(o-tolyl)phosphine (173 mg, 0.57 mmol, 10 mol%), and triethylamine (1.98 mL, 14.19 mmol) were combined in acetonitrile (50 mL) and heated at reflux under nitrogen for 20 h. After cooling to room temperature the reaction mixture was evaporated onto silica gel and then chromatographed [SiO$_2$; (EtOAc/ MeOH/ 880 NH$_3$; 100:5:0.5)/ pentane; 3:1→1:0] to afford the desired title compound as a yellow powder (1.26 g, 59%) Free base: δ$_H$(CDCl$_3$, 300 MHz) 2.28 (6 H, s), 2.49 (3 H, s), 3.52 (2 H, s), 6.80–6.95 (4 H, m), 7.25–7.31 (3 H, m), 7.48 (1 H, d), 7.68 (1 H, s); MS m/z (TS$^+$) 379 (MH$^+$).

EXAMPLES 68–70

The reaction described in Example 67 was repeated using the appropriate alkene and aryl bromide components to provide the following alkenes.

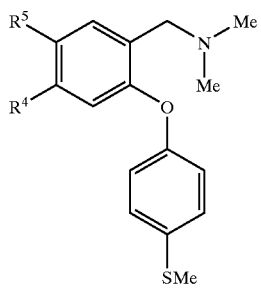

| Example | Starting material | R⁵ | R⁴ | Data |
|---------|-------------------|----|----|------|
| 68[a] | Example 9 | ![acrylamide] H₂N-C(O)-CH=CH- | H | Free base: $\delta_H$(CDCl$_3$, 400MHz)2.30 (6H, s), 2.48(3H, s), 3.50(2H, s), 5.43 (2H, bs), 6.40(1H, d), 6.82(1H, d), 6.90 (2H, d), 7.27(2H, d), 7.34(1H, dd), 7.61 (1H, d), 7.69(1H, d); MSm/z(TS⁺)343 (MH⁺). |
| 69[a] | Example 13 | H | H₂N-C(O)-CH=CH- | Free base: $\delta_H$(CDCl$_3$, 300MHz)2.26 (6H, s), 2.48(3H, s), 3.49(2H, s), 5.49 (2H, bs), 6.32(1H, d), 6.88(2H, d), 7.00 (1H, s), 7.27(3H, m), 7.50(1H, d), 7.53 (1H, d); MSm/z(TS⁺)343(MH⁺). |
| 70 | Example 13 | H | H₂N-SO₂-CH=CH- | Free base: $\delta_H$(CDCl$_3$, 300MHz)2.26 (6H, s), 2.46(3H, s), 3.50(2H, s), 6.79 (1H, d), 6.88(2H, d), 6.94(1H, d), 7.25 (3H, m), 7.41(1H, d), 7.52(H, d); MS m/z(TS⁺)379(MH⁺). |

[a]Acrylamide was used as the alkene coupling partner in these examples.

EXAMPLE 71

2-{3-[(Dimethylamino)methyl]-4-[4-(methylsulfanyl)phenoxy]-phenyl}ethanesulfonamide

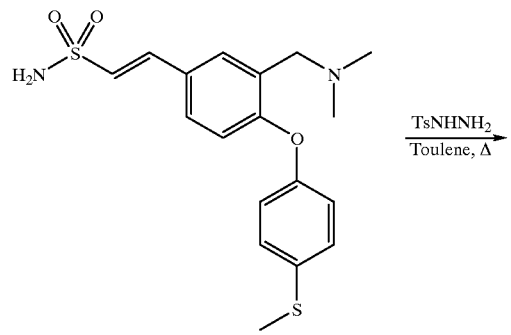

-continued

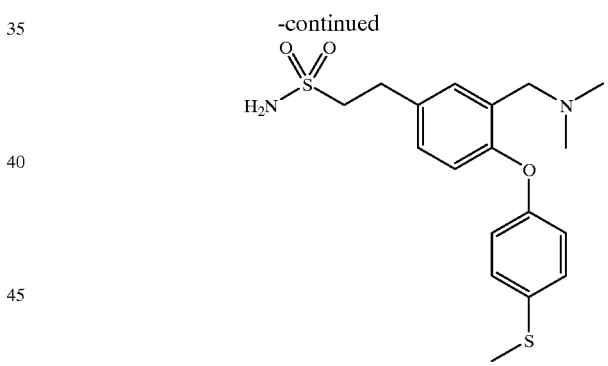

The vinylsulfonamide from example 67 (1.26 g, 3.33 mmol) was heated together with tosyl hydrazine (6.20 g, 33.3 mmol) in toluene at reflux for 5 h. After cooling to rt the solvent was evaporated and the residue partitioned between EtOAc (50 mL) and sat. NaHCO$_3$ (50 mL). The organic layer was separated, washed with water (20 mL), brine (20 mL) and then dried (MgSO$_4$) and evaporated. The residue was purified by flash chromatography [SiO$_2$; (EtOAc/ MeOH/ 880 NH$_3$; 100:5:0.5)/ pentane; 3:1→1:0] to afford the desired product as a cream powder (1.055 g, 83%); Free base: $\delta_H$(CD$_3$OD, 400 MHz) 2.27 (6 H, s), 2.47 (3 H, s), 3.09–3.13 (2 H, m), 3.30–3.36 (2 H, m), 3.50 (2 H, m), 6.83 (1 H, d), 6.87 (2 H, d), 7.19 (1 H, d), 7.27 (2 H, d), 7.35 (1 H, s); MS m/z (TS⁺) 381 (MH⁺).

EXAMPLE 72

2-{4-[(Dimethylamino)methyl]-3-[4-(methylsulfanyl)phenoxy]phenyl}-ethanesulfonamide

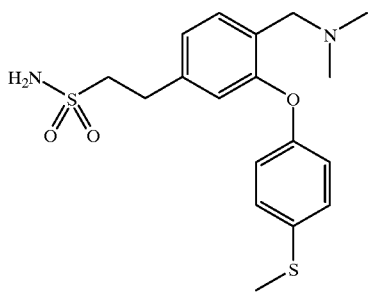

The title sulfonamide was prepared in an analogous fashion to that in Example 71 from the vinylsulfonamide of Example 70. Free base: $\delta_H$(CDCl$_3$, 300 MHz) 2.25 (6 H, s), 2.48 (3 H, s), 3.08 (2 H, m), 3.33 (2 H, m), 3.44 (2 H, m), 4.57 (2 H, brs), 6.73 (1 H, s), 6.86 (2 H, d), 6.98 (1 H, dd), 7.25 (2 H, d), 7.41 (1 H, d); MS m/z (TS$^+$) 381 (MH$^+$).

EXAMPLE 73

3-[(Dimethylamino)methyl]-4-[4-(methylsulfanyl)phenoxy]phenol

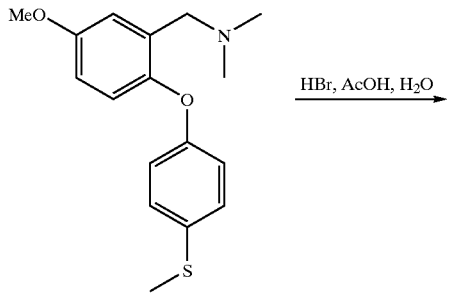

The methylether from example 14 (500 mg, 1.65 mmol) was mixed with hydrogen bromide in acetic acid (30%, 3 mL) and aqueous hydrogen bromide (48%, 200 microlitres), and the mixture heated at reflux overnight under a nitrogen atmosphere. After cooling to room temperature the mixture was evaporated under reduced pressure and the residue partitioned between saturated aqueous sodium bicarbonate (20 mL) and DCM (30 mL). The organic layer was separated and the aqueous layer re-extracted with DCM (4×30 mL). The combined organic fractions were washed with brine, dried (MgSO$_4$) and evaporated to a dark oil. Purification by repeated flash chromatography, first with [silica; DCM/methanol 880 ammonia (95:5:0.5)] and then [SiO$_2$; DCM/methanol/ 880 ammonia (97:3:0.3)] gave partially purified material. This material was dissolved in hydrochloric acid (2 M) and washed with diethyl ether (3×5 mL). The aqueous layer was basified with sat. NaHCO$_{3(aq)}$ (10 mL) and re-extracted with DCM (4×10 mL). The organic fractions were combined and evaporated to a residue which was further purified by flash chromatography [SiO$_2$; DCM/methanol/ 880 ammonia (95:5:0.5)]. This furnished the desired phenol as a white solid (141 mg, 30%); $\delta_H$ (CDCl$_3$, 400 MHz) 2.25 (6 H, s), 2.42 (3 H, s), 3.40 (2 H, s), 6.71 (1 H, m), 6.79 (3 H, d), 6.89 (1 H, s), 7.25 (2 H, d); MS m/z (TS$^+$) 290 (MH$^+$)

EXAMPLE 74

3-[(Methylamino)methyl]-4-[4-(methylsulfanyl)phenoxy]phenol

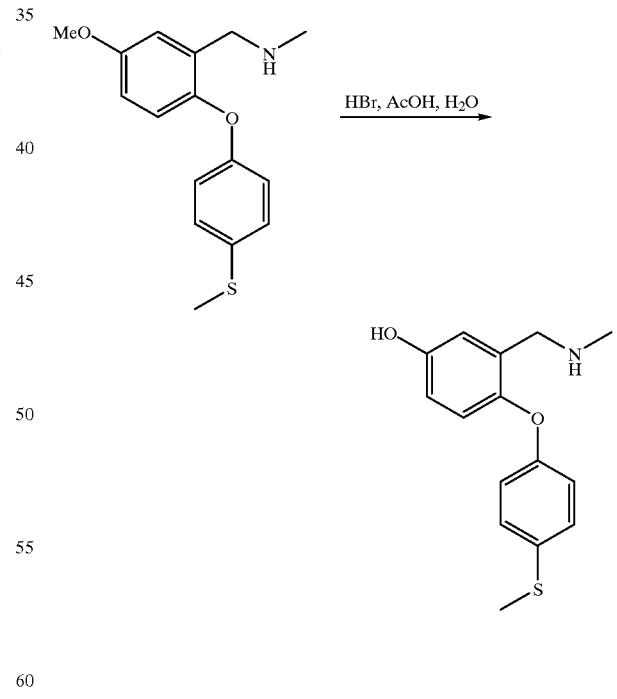

The title compound was prepared from the methyl ether of Example 25 by the method described for Example 73. $\delta_H$ (CDCl$_3$, 400 MHz) 2.35 (3 H, s), 2.43 (3 H, s), 3.59 (2 H, s), 6.70 (1 H, s), 6.80 (2 H, m), 6.83 (2 H, d), 7.25 (2 H, d); MS m/z (TS$^+$) 276 (MH$^+$)

EXAMPLE 75

3-{3-[(Dimethylamino)methyl]-4-[4-(methylsulfanyl)phenoxy]phenyl}propanamide

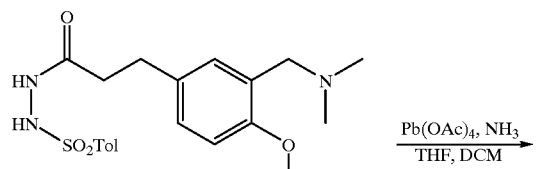

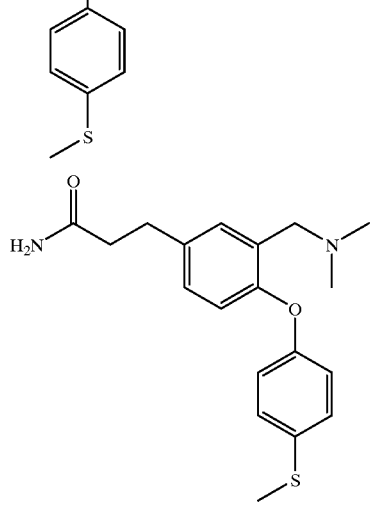

THF (20 mL) was saturated with NH$_3$ and cooled to −60° C. The hydrazide from preparation 68 (756 mg, 1.47 mmol) was added followed by lead tetraacetate (1.30 g, 2.94 mmol) in DCM (15 mL) dropwise. The reaction was stirred at −60° C under a nitrogen atmosphere for 3 hours, then allowed to warm to room temperature overnight. The solvent was removed by evaporation giving an orange residue which was diluted with aqueous sodium hydroxide (2 M) (50 mL) and extracted with ethyl acetate (2×50 mL). The combined organic layers were washed with water (20 mL), brine (30 mL), dried (MgSO$_4$) and evaporated to an orange oil. Purifcation by HPLC [phenomonex Luna C$_8$ 150×21.2 mm, 5 μM; 0.1% aqueous diethylamine/ methanol (gradient)] led to an oil which was partitioned between sodium hydroxide (1 M) and diethyl ether (10 mL). The organic layer was separated, washed with water (10 mL), dried (MgSO$_4$) and evaporated to a clear oil of the title compound which solidified after drying under vacuum (264 mg, 52%); Free base: $\delta_H$(CDCl$_3$, 400 MHz) 2.25 (6 H, s), 2.48 (3 H, s), 2.54 (2 H, t), 2.95 (2 H, t), 3.42 (2 H, s), 5.39 (2 H, brs), 6.81 (1 H, d), 6.85 (2 H, d), 7.07 (1 H, d), 7.25 (2 H, d), 7.33 (1 H, s); MS m/z (TS$^+$) 345 (MH$^+$)

EXAMPLE 76

3-{4-[(Dimethylamino)methyl]-3-[4-(methylsulfanyl)phenoxy]phenyl}propanamide

The title amide was prepared from the hydrazide of Preparation 69 using the method described in Example 75.

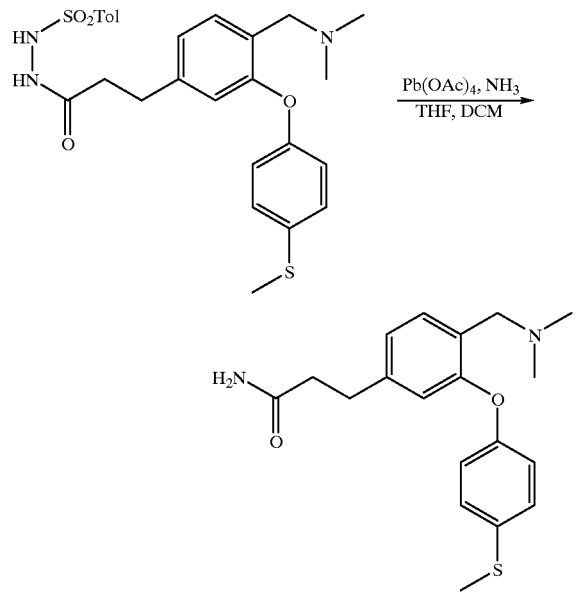

Free base: $\delta_H$(CDCl$_3$, 400 MHz) 2.23 (6 H, s), 2.48 (5 H, m), 2.90 (2 H, t), 3.40 (2 H, s), 5.35 (2 H, brs), 6.75 (1 H, s), 6.85 (2 H, d), 6.98 (1 H, d), 7.25 (2 H, d), 7.38 (1 H, d); MS m/z (TS$^+$) 345 (MH$^+$)

EXAMPLE 77

2-Bromo-5-[(methylamino)methyl]-4-[4-(trifluoromethoxy)phenoxy]-benzenesulfonamide

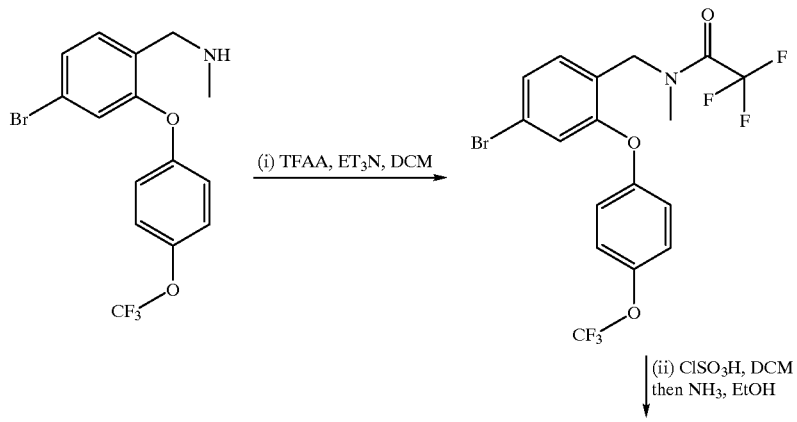

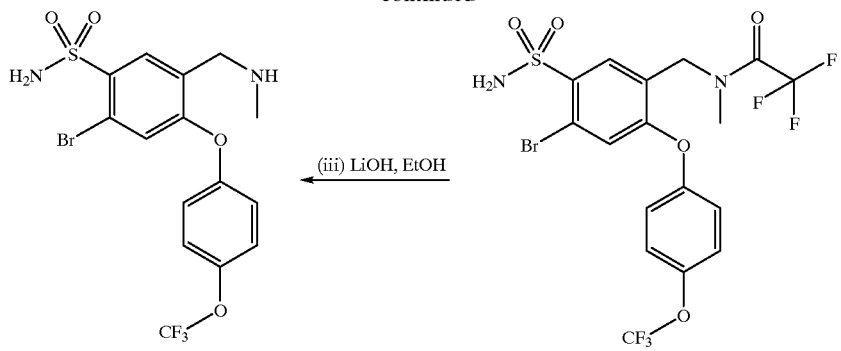

(i) Formation of the trifluoroacetamide: N-{4-bromo-2-[4-(trifluoromethoxy)phenoxy]benzyl}-2,2,2-trifluoro-N-methylacetamide The bromide derivative from example 24 (1.31 g, 3.2 mmol) was dissolved in DCM (12 mL), treated with triethylamine (1.77 mL, 13.9 mol) and the solution cooled to 0° C. Trifluoroacetic anhydride (897 μL, 6.3 mmol) was added dropwise over 5 minutes and stirring was continued for a further 30 minutes. The reaction was quenched by the addition of water (20 mL) and the organic layer was separated. The aqueous layer was re-extracted with DCM (20 mL) and the combined organic fractions dried (MgSO$_4$) and evaporated to a clear oil: δ$_H$(CDCl$_3$, 400 MHz, 2 rotomers visible) 3.00 [3 H, s (minor rotomer)], 3.17 (3 H, s), 4.66 (2 H, s), 4.69 [2 H, s(minor rotomer)]. 6.97–7.02 (3 H, m), 7.22–7.27 (4 H, m); MS m/z (TS$^+$) 489, 491 (MNH$_4^+$).

(ii) Synthesis of sulfonamide: N-{5-(aminosulfonyl)-4-bromo-2-[4-(trifluoromethoxy)phenoxy]benzyl}-2,2,2-trifluoro-N-methylacetamide The trifluoroacetamide from stage (i) (used without further purification) was dissolved in TFA (6 mL) and chlorosulfonic acid was added (2.1 mL, 31.7 mmol). The mixture was stirred overnight at room temperature and then quenched by pouring cautiously onto ice-water. A white solid precipitated and was collected by filtration and then dissolved in DCM, dried (MgSO$_4$), filtered and evaporated to a yellow oil. The oil was treated with saturated NH$_3$ in ethanol (30 mL) and after 30 minutes, the solvents were evaporated. Purification of the residue by flash chromatography [SiO$_2$; DCM, MeOH, 880 NH$_3$ (93:7:1)] afforded the desired sulfonamide as a white solid (825 mg, 47%); δ$_H$(CDCl$_3$, 400 MHz, 2 rotomers visible) 3.04 (3 H, s, minor rotomer), 3.10 (3 H, s), 4.72 (2 H, s), 4.75 (2 H, s, minor rotomer), 5.15 (2 H, brs), 7.04–7.09 (3 H, m), 7.24–7.35 (2 H, m), 8.00 (1 H, s, minor rotomer), 8.09 (1 H, s); MS m/z (TS$^+$) 568, 570 (MNH$_4^+$).

(iii) Hydrolysis of trifluoroacetamide group: 2-bromo-5-[(methylamino)methyl]-4-[4-(trifluoromethoxy)phenoxy]benzenesulfonamide The sulfonamide from stage (ii) was dissolved in ethanol (10 mL) and treated with 1 M LiOH$_{(aq)}$ (20 mL). The mixture was stirred for 10 minutes before being evaporated to remove most of the ethanol. The aqueous mixture resulting was extracted with diethyl ether (2×50 mL) and the combined extracts washed with brine (100 mL), dried (MgSO$_4$) and evaporated to a white solid (550 mg, 81%); δ$_H$(CDCl$_3$, 400 MHz) 2.46 (3 H, s), 3.84 (3 H, s), 7.05 (2 H, d), 7.06 (1 H, s), 7.27 (2 H, d), 8.20 (1 H, s); MS mz (TS$^+$) 455,457 (MH$^+$).

EXAMPLE 78

5-[(Methylamino)methyl]-2-(methylsulfanyl)-4-[4-(trifluoromethoxy)phenoxy]-benzenesulfonamide

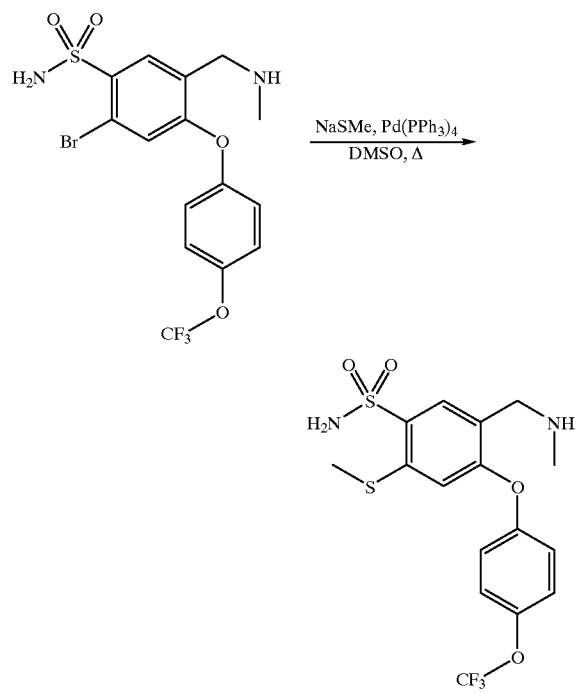

The sulfonamide from example 77 (510 mg, 1.1 mmol) was dissolved in DMSO (3 mL) and treated with palladium tetrakis(triphenylphosphine) (129 mg, 0.11 mmol) and sodium methanethiolate (157 mg, 2.2 mmol). The mixture then was heated at 100° C. under a nitrogen atmosphere for 18 h. After cooling to room temperature the mixture was partitioned between water and diethyl ether (50 mL each). The ether layer was separated and the organic layer re-extracted with diethyl ether (2×25 mL). The combined organic fractions were dried (MgSO$_4$) and evaporated to an orange oil. Purification by flash chromatography [SiO$_2$; DCM/ MeOH/ 880 NH$_3$ (93:7:1)] gave a white solid (286 mg, ca 60%) which was shown by $^1$H-NMR to be a 60:40 mixture of desired product: starting bromide. A portion of this sample was further purified by HPLC [Magellen C18 15*21.12 cm column, 0.2% diethylamine$_{(aq)}$/ acetonitrile (50:50), flow rate 20 mL/ min] to afford the desired title compound (retention time 8.2 min) as a white solid (22.1 mg); $\delta_H$(CDCl$_3$, 400 MHz) 2.32 (3 H, s), 2.37 (3 H, s), 3.75 (2 H, s), 6.83 (1 H, s), 7.12 (2 H, d), 7.32 (2 H, d), 8.00 (1 H, s); MS m/z (TS$^+$) 423 (MH$^+$).

EXAMPLES 79–80

2-bromo-5-[(dimethylamino)methyl]-4-[4-(trifluoromethoxy)phenoxy]-benzenesulfonamide (Example 79) and 5-[(dimethylamino)methyl]-2-(methylsulfanyl)-4-[4-(trifluoromethoxy)phenoxy]-benzenesulfonamide (Example 80)

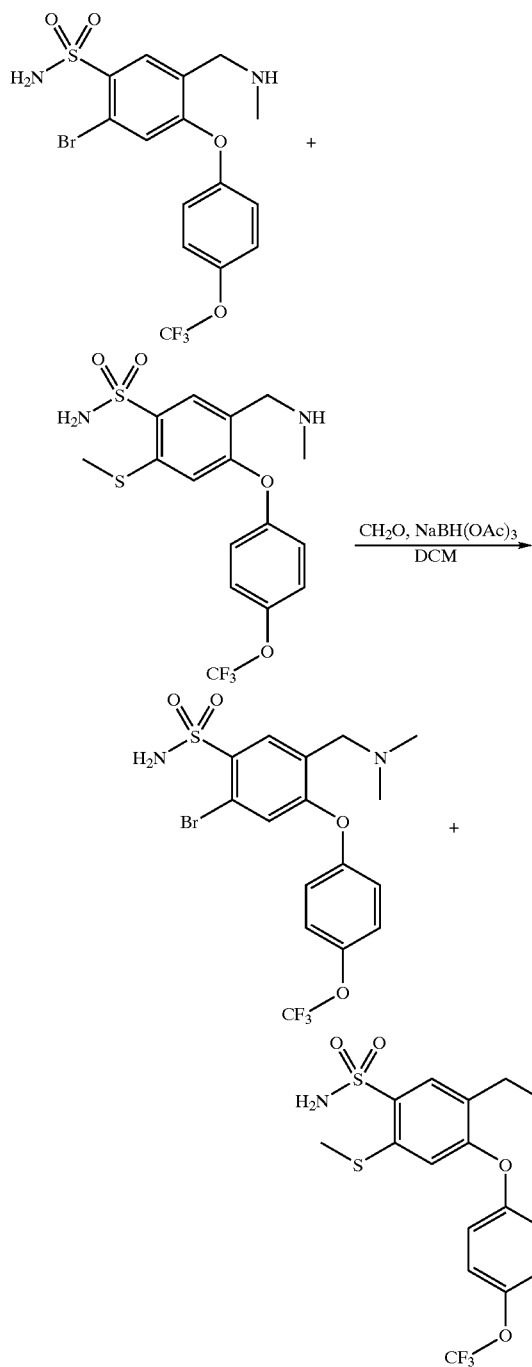

The mixture of bromo- and methylsulfanyl- sulfonamides obtained from the reaction of Example 78 prior to the HPLC purification (136 mg, ca. 0.3 mmol) was dissolved in DCM (2 mL) and treated with formaldehyde (37% aqueous) (80 µL, 3 equivs). The reaction mixture was stirred for 30 minutes before the addition of sodium tri(acteoxy) borohydride (273 mg, 1.3 mmol). After stirring for a further 1 hour, the mixture was evaporated, quenched by the addition of hydrochloric acid (2 M) and the pH made slightly basic by the addition of aqueous sodium hydroxide (2 M). The mixture was extracted with ether (2×30 mL), the combined organic fractions were dried (MgSO$_4$) and evaporated to a colourless oil. Purification by flash chromatography [silica; 97:3:0.3 (DCM/ methanol/ 880 ammonia)] afforded a white foam, which upon dissolution in diethyl ether and dilution with pentane formed a white powder. This material was shown by $^1$H NMR to be a 50:50 mixture of Example 79 and 80. This sample was further purified by HPLC [Magellen C18 15*21.12 cm column, 0.2% diethylamine$_{(aq)}$/ acetonitrile (50:50), flow rate 20 mL/min] to afford Example 79 (retention time: 12.02 min, 15 mg], and Example 80 (retention time: 12.56 min, 25.6 mg):

Example 79: 15 mg, free base: $\delta_H$(CDCl$_3$, 400 MHz) 2.26 (6 H, s), 3.56 (2 H, s), 7.08 (1 H, s), 7.13 (1 H, d), 7.33 (1 H, d), 8.16 (1 H, s); MS m/z (TS$^+$) 469, 471 (MH$^+$).

Example 80: 25.6 mg, hydrochloride salt: $\delta_H$(CD$_3$OD, 400 MHz) 2.30 (3 H, s), 2.88 (6 H, s), 4.40 (2 H, brs), 6.80 (1 H, s), 7.28 (2 H, d), 7.40 (2 H, d), 8.14 (1 H, d); MS m/z (TS$^+$) 437 (MH$^+$).

EXAMPLE 81

3-[(Methylamino)methyl]-4-[4-(trifluoromethoxy) phenoxy]benzonitrile

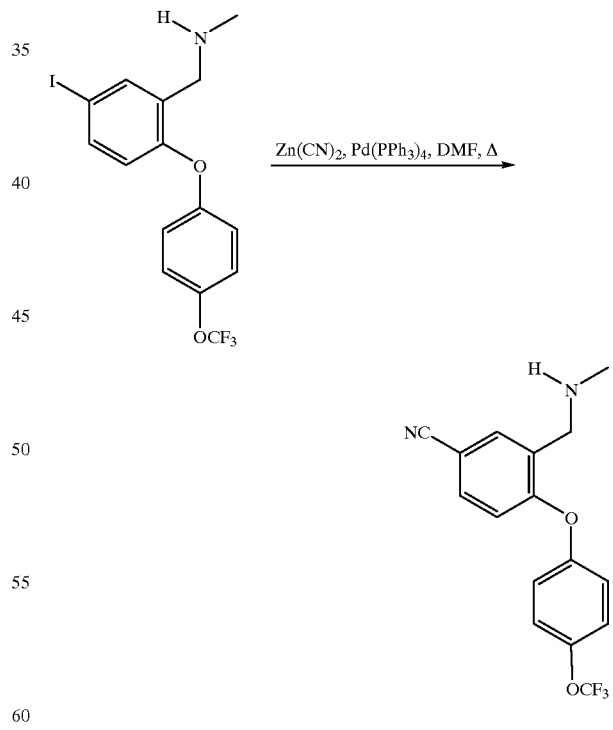

The product of Example 17 (2.46 g, 5.8 mmol) was dissolved in DMF (30 mL) together with palladium tetrakis (triphenylphosphine) (0.538 g, 0.47 mmol) and zinc(II) cyanide (478 mg, 4.1 mmol). The reaction mixture was stirred and heated at 100° C. for 12 h. After cooling to room temperature the reaction mixture was poured into water and extracted three times with ethyl acetate. The combined organic extracts were dried (MgSO$_4$) and evaporated to a brown oil. The residue was purified by flash chromatography [SiO$_2$; DCM/ methanol/880 ammonia (95:5:0.5→90:10:1)]. The resulting material was recolumned [SiO$_2$; ethyl acetate/ methanol/ 880 ammonia (95:5:0.5)] to leave an off white solid. The material was further purified by trituration with ethyl acetate/diethyl ether followed by drying under vacuum to give the desired nitrile compound as an off white solid (1.2 g, 64%); $\delta_H$(CDCl$_3$, 400 MHz) 2.67 (3 H, s), 4.24 (2 H, s), 6.77 (1 H, d), 7.32 (4 H, m), 7.58 (1 H, d), 8.02 (1 H, s); MS m/z (TS$^+$) 323 (MH$^+$).

EXAMPLES 82–86

A series of nitriles was prepared from the requisite aryl halides (iodides or bromides) by the procedure described for the preparation of Example 81.

| Example | Starting Material | R$^5$ | R$^4$ | R$^3$ | Data |
|---|---|---|---|---|---|
| 82 | Example 12 | H | NC— | —CF$_3$ | $\delta_H$(CDCl$_3$, 400MHz) 2.25(6H, s), 3.48(2H, s), 6.99(2H, d), 7.17 (1H, s), 7.48(1H, d), 7.61(2H, d), 7.68(1H, d); MSm/z(TS$^+$) 321(MH$^+$). |
| 83 | Example 18 | NC— | H | —CF$_3$ | $\delta_H$(CDCl$_3$, 300MHz) 2.28(6H, s), 3.50(2H s), 6.91(1H, d), 7.05(2H, d), 7.51(1H, d), 7.62 (2H, d), 7.87(1H, d); MSm/z(TS$^+$)321 (MH$^+$). |
| 84 | Example 16 | NC— | H | —OCF$_3$ | $\delta_H$(CDCl$_3$, 400MHz) 2.30(6H, s), 3.53(2H, s), 6.83(1H, d), 7.00 (2H, m); 7.23(2H, m), 7.47(1H, m), 7.83(1H, s); MSm/z(TS$^+$)337 (MH$^+$) |
| 85 | Example 9 | NC— | H | —SMe | $\delta_H$(CDCl$_3$, 400MHz) 2.30(6H, s), 2.50(3H, s), 3.57(2H, s), 6.80 (1H, d), 6.95(2H, d), 7.30(2H, d), 7.45(1H, dd), 7.82(1H, d); MS m/z(TS$^+$)299(MH$^+$) |
| 86 | Example 8 | H | NC— | —OCF$_3$ | $\delta_H$(CDCl$_3$, 300MHz) 2.24(6H, s), 3.50(2H, s), 6.93(2H, d), 7.20 (2H, d), 7.37–7.48(2H, m), 7.63(1H, d); MS m/z(TS$^+$) 337 (MH$^+$) |

EXAMPLE 87

3-[(Methylamino)methyl]-4-[4-(methylsulfanyl) phenoxy]benzonitrile

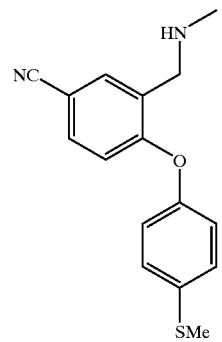

The title nitrile was prepared from the bromide of example 23 according to the preocedure described for example 81; $\delta_H$(DMSO-D$_6$, 300 MHz) 2.47 (3 H, s), 2.62 (3 H, s), 4.25 (2 H, s), 6.81 (1 H, d), 7.18 (2 H, d), 7.40 (2 H, d), 7.81 (1 H, dd), 8.06 (1 H, d), 9.03 (2 H, br); MS m/z (TS$^+$) 285 (MH$^+$).

EXAMPLE 88

{3-[(Dimethylamino)methyl]-4-[4-(methylsulfanyl) phenoxy]phenyl}acetonitrile

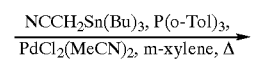

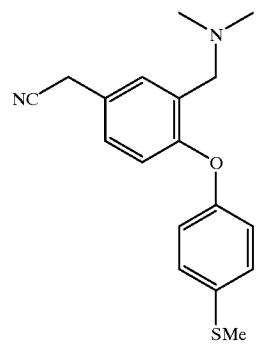

A mixture of the bromide of Example 9 (1.5 g, 4.26 mmol), tributyl(cyanomethyl)stannane [prepared according to M. Kosugi, M. Ishiguro, Y. Negishi, H. Sano, T. Migita, Chem. Lett., 1984, 1511–1512] (2.1 g, 6.36 mmol), tri-o-tolylphosphine (78 mg, 0.26 mmol), bis(acetonitrile) dichloropalladium(II) (33 mg, 0.13 mmol) and m-xylene (20 mL) was stirred at 120° C. under nitrogen for 16 h. After cooling to room temperature the solvent was removed in vacuo and the residue was purified by flash chromatography [SiO$_2$; DCM/ MeOH/ 880 NH$_3$ (97:3:0.5)] to give the desired compound (895 mg, 67%) as a yellow oil; δ$_H$(CDCI$_3$, 400 MHz) 2.27 (6 H, s), 2.47 (3 H, s), 3.46 (2 H, s), 3.74 (2 H, s), 6.87 (3 H, m), 7.18 (1 H, d), 7.25 (2 H, d), 7.45 (1 H, s); MS m/z (TS$^+$) 313.

EXAMPLE 89

{3-[(Dimethylamino)methyl]-4-[4-(trifluoromethoxy)phenoxy]phenyl}aceto nitrile

Step 1. Preparation of intermediate cyanoester

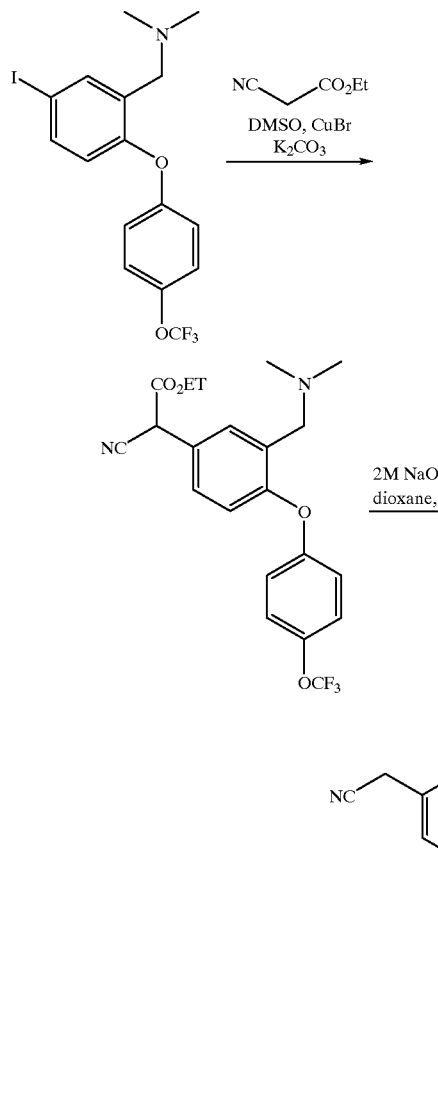

A mixture of the iodide compound of example 16 (1.03 g, 2.37 mmol), CuBr (1.70 g, 11.8 mmol), α-cyanoethyl acetate (1.337 g, 11.83 mmol) and potassium carbonate (3.29 g, 23.7 mmol) in DMSO (30 mL) was heated at 120° C. under nitrogen for 2 h. After cooling to room temperature the mixture was partitioned between ether and saturated aqueous ammonium chloride. The organic layer was washed with brine, dried (MgSO$_4$) and concentrated in vacuo. The residue was purified by flash chromatography [SiO$_2$; DCM/ MeOH (98:2)] to give the desired intermediate cyanoester (410 mg, 41%); δ$_H$(CDCI$_3$, 400 MHz) 1.27 (3 H, t), 2.22 (6 H, s), 3.46 (2 H, s), 4.23 (2 H, q), 4.64 (1 H, br), 6.89 (1 H, d), 6.92 (2 H, d), 7.18 (2 H, d), 7.33 (1 H, d), 7.60 (1 H, s); MS m/z (TS$^+$) 423 (MH$^+$).

Step 2. Ester hydrolysis/ decarboxylation to provide the desired nitrile compound {3-[(dimethylamino)methyl]-4-[4-(trifluoromethoxy)phenoxy]pheny{lacetonitrile Sodium hydroxide (39 mg, 0.97 mmol) was added to a solution of the intermediate cyanoester (410 mg, 0.97 mmol) in dioxane (40 mL) and the mixture was heated at reflux for 2 h. After cooling to room temperature the reaction mixture was partitioned between ether and water. The organic layer was washed with brine, dried (MgSO$_4$) and concentrated in vacuo. The residue was purified by flash chromatography [SiO$_2$; DCM/ MeOH (97:3)] to give the desired nitrile compound (141 mg, 41%); δ$_H$(CDCI$_3$, 400 MHz) 2.25 (6 H, s), 3.43 (2 H, s), 3.75 (2 H, s), 6.85–6.97 (3 H, m), 7.13–7.24 (3 H, m), 7.46 (1 H, s); MS m/z (TS$^+$) 351 (MH$^+$).

EXAMPLE 90

4-[(Dimethylamino)methyl]-3-[4-(trifluoromethyl)phenoxy]benzamide

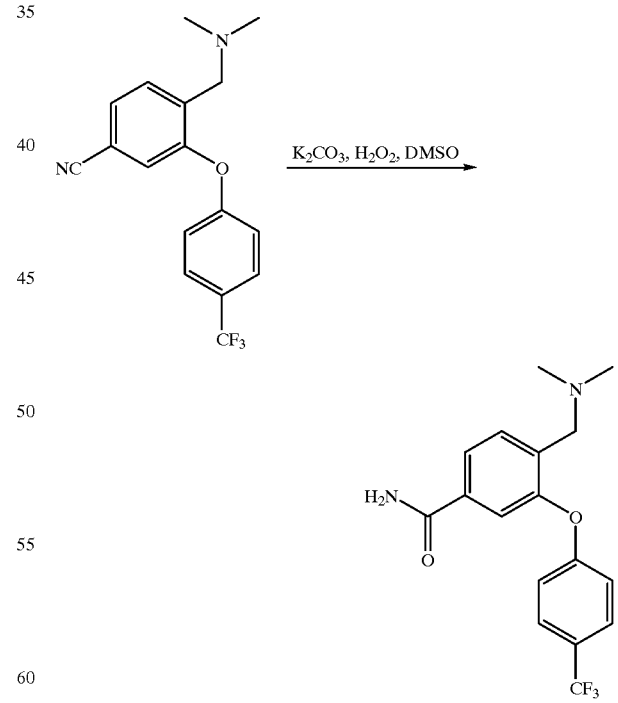

The nitrile compound of Example 82 (300 mg, 0.94 mmol) was dissolved in DMSO (2 mL) and potassium carbonate (43 mg, 0.3 mmol) was added followed by H$_2$O$_2$ (30%, 0.2 mL). The reaction was stirred at room temperature for 30 min before being diluted with water (5 mL) and being extracted with diethyl ether (2×10 mL). The combined ether layers were dried with MgSO$_4$ and evaporated to an oil. This residue was purified by flash chromatography [SiO$_2$; DCM/ MeOH/ 880 NH$_3$ (93:7:1)] to afford the desired amide compound as a colourless solid (258 mg, 78%); $\delta_H$(CDCl$_3$, 300 MHz) 2.24 (6 H, s), 3.45 (2 H, s), 5.60–6.00 (2 H, 2×brs), 6.98 (2 H, d), 7.44 (1 H, s), 7.54–7.64 (4 H, m); MS m/z (TS$^+$) 339 (MH$^+$).

EXAMPLE 91

3-[(Dimethylamino)methyl]-4-[4-(methylsulfanyl)phenoxy]benzamide

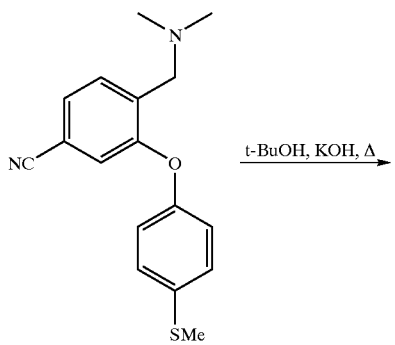

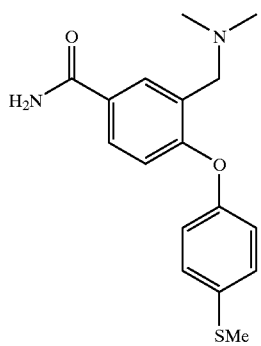

The nitrile compound of Example 85 (60 mg, 0.2 mmol) was dissolved in tert-butanol, potassium hydroxide (45 mg, 0.8 mmol) was added and the mixture refluxed under nitrogen for 1 h. The mixture was cooled and diluted with water and EtOAc. The organic layer was separated, washed with brine, dried (MgSO$_4$) and evaporated to a pale yellow gum. Purification by flash chromatography [SiO$_2$; DCM/ MeOH/ 880 NH$_3$ (95:5:1)] afforded the desired amide as a white powder (39 mg, 61%); $\delta_H$ (CDCl$_3$, 400 MHz) 2.30 (6 H, s), 2.50 (3 H, s), 3.57 (2 H, s), 5.60 (1 H, br), 6.00 (1 H, br), 6.86 (1 H, d), 6.92 (2 H, d), 7.27 (2 H, d), 7.73 (1 H, dd), 7.93 (1 H, s); MS m/z (TS$^+$) 317 (MH$^+$).

EXAMPLE 92

2-{3-[(Dimethylamino)methyl]-4-[4-(methylsulfanyl)phenoxy]phenyl}acetamide

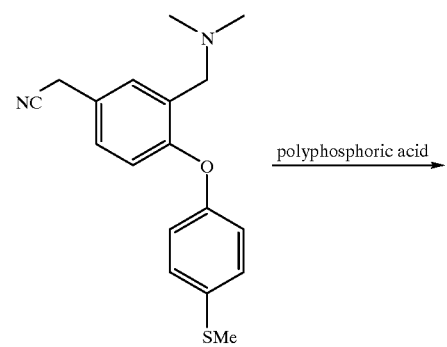

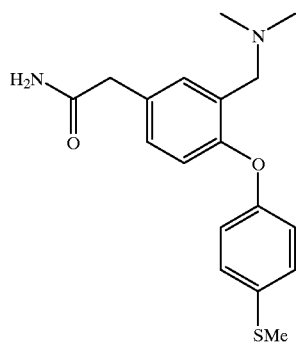

A mixture of the nitrile compound of Example 88 (100 mg, 0.32 mmol) and polyphosphoric acid (750 mg) was heated at 110° C. under nitrogen for 75 min. After cooling to room temperature sodium hydroxide (2 M) was added and the resulting mixture was extracted with ethyl acetate (3 times). The combined organic extracts were dried (MgSO$_4$) and concentrated in vacuo. The residue was purified by flash chromatography [DCM/ MeOH/880 NH$_3$ (93:7:1→90:10:1)] to give the desired primary amide compound (58 mg, 55%); $\delta_H$ (CDCl$_3$, 400 MHz) 2.25 (6 H, s), 2.45 (3 H, s), 3.45 (2 H, s), 3.55 (2 H, s), 5.63 (1 H, br), 5.76 (1 H, br), 6.87 (3 H, m), 7.15 (1 H, d), 7.25 (2 H, d), 7.40 (1 H, s); MS m/z (TS$^+$) 331 (MH$^+$).

EXAMPLES 93–97

A series of primary amides was prepared by application of the appropriate hydrolysis conditions on the requisite nitriles according to the reactions described in Examples 90, 91 or 92.

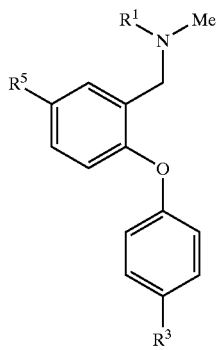

| Example | Hydrolysis procedure | Starting Material | R⁵ | R³ | R¹ | Data |
|---|---|---|---|---|---|---|
| 93 | (Ex. 90) | Example 81 | H₂N-C(=O)-CH₂- | OCF₃ | H | $\delta_H$(CDCl₃, 400MHz) 2.45(3H, s), 3.82(2H, s), 6.18(1H, br), 6.46 (1H, br), 6.83(1H, d), 6.99(2H, m), 7.20(2H, m), 7.72(1H, dd), 7.93 (1H, d); MSm/z(TS⁺)341 (MH⁺). |
| 94 | (Ex. 90) | Example 84 | H₂N-C(=O)-CH₂- | OCF₃ | Me | $\delta_H$(CDCl₃, 300MHz) 2.28(6H, s) 3.53(2H, S), 5.70(1H, br), 6.09 (1H, br) 6.91(1H, d), 6.98(2H, m), 7.20(2H, m), 7.78(1H, dd), 7.96 (1H, d); MSm/z(TS⁺) 355(MH⁺). |
| 95 | (Ex. 90) | Example 83 | H₂N-C(=O)-CH₂- | CF₃ | Me | $\delta_H$(CDCl₃, 400MHz) 2.27(6H, s), 3.50(2H, s), 6.96(1H, d), 7.00 (2H, d), 7.58(2H, d), 7.78(1H, dd), 8.00(1H, s); MSm/z(TS⁺)339 (MH⁺). |
| 96 | (Ex. 90) | Example 89 | H₂N-C(=O)-CH₂-CH₂- | OCF₃ | Me | $\delta_H$(CDCl₃, 400MHz) 2.28(6H, s), 3.46(2H, s), 3.58(2H, s), 5.51 (2H, brs), 6.88(1H, d), 6.92(2H, d), 7.12–7.20 (3H, m), 7.42(1H, s); MSm/z(TS⁺)369 (MH⁺). |
| 97 | (Ex. 91) | Example 87 | H₂N-C(=O)-CH₂- | SMe | H | $\delta_H$(DMSO-D6, 300MHz) 2.30(3H, s), 2.47(3H, s), 3.72(2H, s), 6.79 (1H, d), 6.96(2H, d), 7.28(3H, m), 7.74(1H, d), 7.86(1H, br), 8.00 (1H, s); MSm/z(TS⁺) 303(MH⁺) |

EXAMPLE 98

4-[(Dimethylamino)methyl]-3-[4-(trifluoromethoxy)phenoxy]benzamide

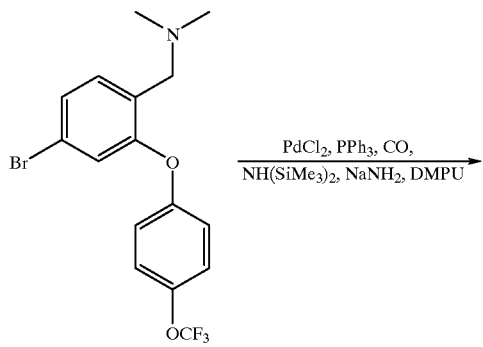

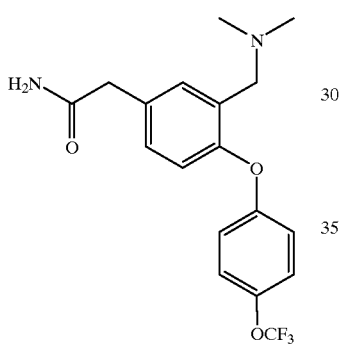

EXAMPLES 99–100

4-[(dimethylamino)methyl]-N-methyl-3-[4-(trifluoromethoxy)phenoxy]benzamide (Example 99) and
4-[(dimethylamino)methyl]-N,N-dimethyl-3-[4-(trifluoromethoxy)phenoxy]-benzamide (Example 100)

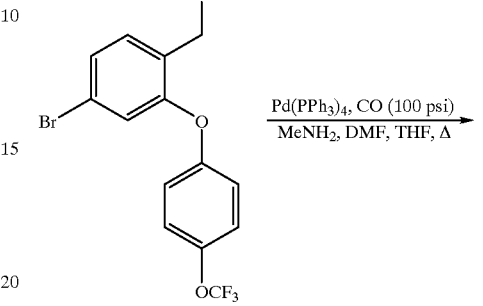

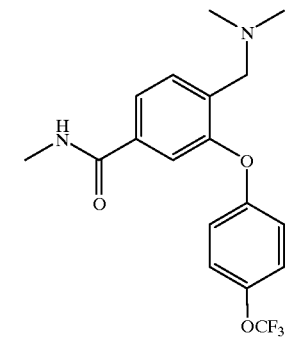

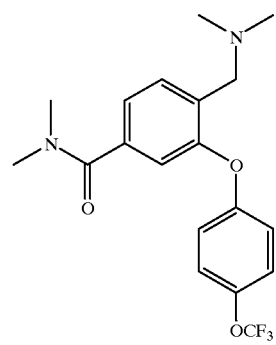

A mixture of the bromide compound of Example 8 (500 mg, 1.28 mmol), paladium (II) chloride (7 mg, 0.04 mmol), triphenylphosphine (20 mg, 0.08 mmol), hexamethyidisilazane (1.08 mL, 5.12 mmol) and DMPU (5 mL) was heated at 120° C. under carbon monoxide (100 psi pressure) for 16 h. At this point TLC analysis indicated no change, so palladium tetrakis(triphenylphosphine) (200 mg, 0.17 mmol) and sodamide (500 mg, 12.8 mmol) were added and the reaction was heated at 120° C. under carbon monoxide (100 psi pressure) for a further 16 h. Methanol was added and the mixture was concentrated in vacuo to give a black oil. This was partitioned between ethyl acetate and sodium hydroxide solution (1 M), the organic layer was washed with water (3 times) and brine, dried (MgSO$_4$) and concentrated in vacuo. The residue was purified by repeated flash chromatography on silica to give the desired primary amide compound (33 mg, 7%) as a pale yellow powder; $\delta_H$(CDCl$_3$, 400 MHz) 2.25 (6 H, s), 3.50 (2 H, s), 5.50 (1 H, br), 5.90 (1 H, br), 6.95 (2 H, d), 7.17 (2 H, d), 7.39 (1 H, s), 7.55 (1 H, d), 7.58 (1 H, d); MS m/z (TS$^+$) 355 (MH$^+$).

The bromide compound of Example 8 (500 mg, 1.28 mmol) was dissolved in DMF (10 mL) together with monomethylamine (2 M in THF, 6.4 mL, 12.8 mmol), triethylamine (446 µL, 3.2 mmol), and palladium tetrakis (triphenylphosphine) (75 mg, 0.06 mmol). The reaction mixture was placed in a bomb, carbon monoxide was introduced to a pressure of 50 psi, and the mixture heated at 100° C. overnight. The pressure was released and further palladium catalyst added (100 mg, 0.09 mmol) together with extra monomethylamine in THF (3 mL, 6 mmol). Carbon monoxide was then introduced to a pressure of 100 psi and the mixture heated again overnight at 120° C. After releasing the pressure a further load of palladium catalyst was added (130 mg, 0.1 mmol) and the mixture heated at 120° C. under 100 psi of carbon monoxide for a further 4 h. After this time, in order to drive the reaction to completion (as judged by TLC analysis) further batches of palladium catalyst (200 mg, 0.17 mmol) and methylamine in THF (6.4 mL, 12.8 mmol) were added. The reaction mixture was then heated at 120° C. under 100 psi of carbon monoxide for a further 60 h. After releasing the pressure for the final time the solvents were evaporated under reduced pressure to leave an orange oil. The oil was basified with sodium hydroxide (1 M) and extracted with ethyl acetate. The organic extract was washed with water (x3), brine, dried over $MgSO_4$ and then evaporated to an orange oil. Purification by repeated flash chromatography [$SiO_2$; MeOH (2.5%–5%) in DCM containing 0.5% 880 $NH_3$] to afford the methylamide compound as a colourless oil which slowly crystallised upon standing (105 mg, 23%) and the corresponding dimethylamide material as a colourless oil (130 mg, 27%).

EXAMPLE 99

$\delta_H$(CDCl$_3$, 400 MHz) 2.26 (6 H, s), 2.98 (3 H, d), 3.50 (2 H, s), 6.00 (1 H, br), 6.95 (2 H, d), 7.17 (2 H, d), 7.33 (1 H, s), 7.50 (1 H, d), 7.58 (1 H, d); MS m/z (TS$^+$) 369 (MH$^+$).

EXAMPLE 100

$\delta_H$(CDCl$_3$, 400 MHz) 2.27 (6 H, s), 2.95 (3 H, br), 3.05 (3 H, br), 3.47 (2 H, s), 6.95 (2 H, d), 6.96 (1 H, s), 7.15 (2 H, d), 7.20 (1 H, d), 7.50 (1 H, d); MS m/z (TS$^+$) 383 (MH$^+$).

EXAMPLES 101–106

A series of mono- and di-methyl amines were prepared in an analogous fashion to the reactions described for the preparation of Examples 99 and 100, starting from the requisite bromides or iodides. In each case the reaction was performed at such a temperature and pressure, and with sufficient catalyst to ensure complete consumption of starting materials.

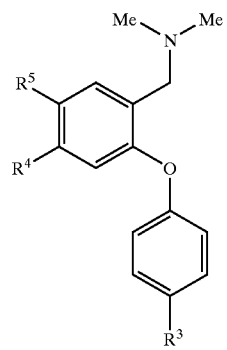

| Example | Starting Material | R$^5$ | R$^4$ | R$^3$ | Data |
|---|---|---|---|---|---|
| 101 | Example 7 | —NHC(O)CH$_3$ (methylamide) | H | —OCF$_3$ | $\delta_H$ (CDCl$_3$, 400MHz) 2.27(6H, s), 3.01 (3H, d), 3.51(2H, s), 6.19(1H, br), 6.89(1H, d), 6.97(2H, m), 7.18(2H, m), 7.70(1H, dd), 7.86(1H, d); MSm/z (TS$^+$)369(MH$^+$) |
| 102 | Example 7 | —N(CH$_3$)C(O)CH$_3$ (dimethylamide) | H | —OCF$_3$ | $\delta_H$ (CDCl$_3$, 400MHz) 2.24(6H, s), 3.00 (3H, br), 3.07(3H, br), 3.48(2H, s), 6.89(1H, d), 6.95(2H, m) 7.17(2H, m), 7.34(1H, dd), 7.58(1H, d); MSm/z (TS$^+$)383(MH$^+$) |
| 103 (HCl salt) | Example 3 | —N(CH$_3$)C(O)CH$_3$ | H | —CF$_3$ | $\delta_H$ (CDCl$_3$, 400MHz) 2.82(6H, s), 3.14 (6H, s), 4.30(2H, s), 6.94(1H, d), 7.16 (2H, d), 7.57(1H, d), 7.65(2H, d), 8.00 (1H, s), 13.00(1H, s); MSm/z(TS$^+$) 367(MH$^+$). |
| 104 | Example 3 | —NHC(O)CH$_3$ | H | —CF$_3$ | $\delta_H$ (CDCl$_3$, 300MHz) 2.11(6H, s), 2.99 (3H, d), 3.43(2H, s), 6.26(1H, brs), 6.92–7.00(3H, m), 7.57(2H, d), 7.74 (1H, dd), 7.86(1H, d); MSm/z(TS$^+$) 353(MH$^+$). |
| 105 | Example 12 | H | —NHC(O)CH$_3$ | —CF$_3$ | $\delta_H$ (CDCl$_3$, 300MHz) 2.14(6H, s), 2.84 (2H, d), 3.37(2H, s), 6.65(1H, brs), 6.89(2H, d), 7.37(1H, s), 7.50–7.44 (3H, m), 7.59(1H, d); MSm/z(TS$^+$) 353(MH$^+$). |

| Example | Starting Material | R⁵ | R⁴ | R³ | Data |
|---|---|---|---|---|---|
| 106 | Example 12 | H | 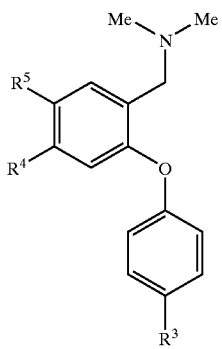 | —CF₃ | δ_H (CDCl₃, 400MHz) 2.14(6H, s), 2.96 (3H, brs), 3.06(3H, brs), 3.43(2H, s), 6.97–7.00(3H, m), 7.26(1H, m), 7.56 (3H, d); MSm/z(TS⁺)367(MH⁺). |

EXAMPLE 107

N-{5-Amino-2-[4-(trifluoromethyl)phenoxy]benzyl}-N,N-dimethylamine

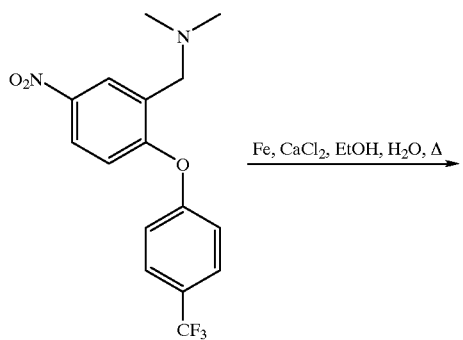

A mixture of the nitro compound of Example 21 (400 mg, 1.18 mmol), iron powder (591 mg, 10.6 mmol) and calcium chloride (65 mg, 0.59 mmol) in 85% aqueous ethanol (15 mL) was heated at reflux for 18 h. The reaction mixture was cooled to room temperature and filtered through Celite®, washing thoroughly with ethanol and then ethyl acetate. The solvent was removed in vacuo and the residue was purified by flash chromatography [SiO₂; DCM/ MeOH/ 880 NH₃ (95:5:0.5)] to give the desired aniline compound (299 mg, 82%) as a beige solid; δ_H(CDCl₃, 300 MHz) 2.20 (6 H, s), 3.27 (2 H, s), 3.63 (2 H, brs), 6.60 (1 H, dd), 6.80 (1 H, d), 6.87 (1 H, d), 6.90 (2 H, d), 7.50 (2 H, d); MS m/z (TS⁺) 310 (MH⁺).

EXAMPLES 108–109

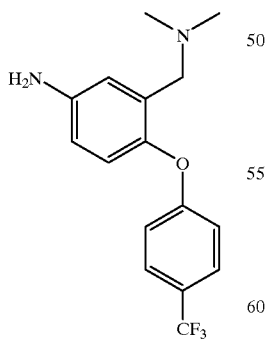

A range of anilines was prepared from the requisite nitro compounds using the conditions described in Example 107. Data for these compounds are presented below.

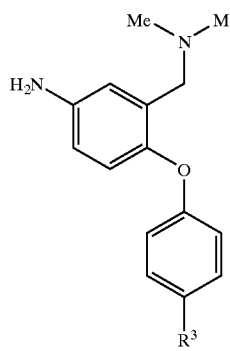

| Example | Starting Material | R³ | Data |
|---|---|---|---|
| 108 | Example 22 | —OCF₃ | δ_H (CDCl₃, 400MHz) 2.22(6H, s), 3.30(2H, s), 3.62 (2H, br), 6.59(1H, dd), 6.78(1H, d), 6.83(3H, m), 7.10(2H, d); MSm/z(TS⁺)327(MH⁺) |
| 109 | Example 19 | —SMe | δ_H (CDCl₃, 400MHz) 2.26(6H, s), 2.44(3H, s), 3.36 (2H, s), 3.61(2H, br), 6.58(1H, dd), 6.79(3H, m), 6.87 (1H, d), 7.22(2H, m); MSm/z(TS⁺)289(MH⁺) |

EXAMPLE 110

N-{5-(Aminomethyl)-2-[4-(trifluoromethoxy)phenoxy]benzyl}-N,N-dimethylamine

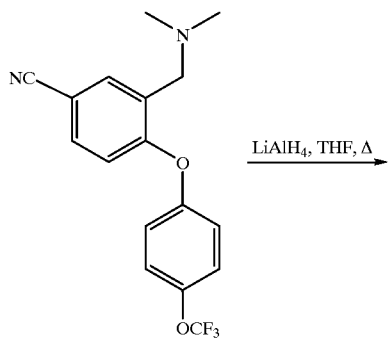

A solution of lithium aluminium hydride in THF (1 M, 7.1 mL, 7.1 mmol) was added dropwise to a solution of the nitrile compound of Example 84 (2.40 g, 7.14 mmol) in THF (50 mL) at room temperature under nitrogen and stirred overnight. A further addition of lithium aluminium hydride in THF was made (1 M, 7.1 mL, 7.1 mmol) and the mixture was heated at reflux for 1 h, before being cooled to room temperature and quenched cautiously with water. The mixture was dried (MgSO₄), filtered (washing thoroughly with THF) and the filtrate and washings concentrated in vacuo. Purification of the residue by flash chromatography [SiO₂; DCM/ MeOH/ 880 NH₃ (90:10:1→84:14:2)] gave the desired amine compound (1.95 g, 80%) as a reddish oil; δ_H(CDCl₃, 400 MHz) 1.73, (2 H, br), 2.26 (6 H, s), 3.43 (2 H, s), 3.87 (2 H, s), 6.90 (3 H, m), 7.13 (2 H, d), 7.20 (1 H, dd), 7.43 (1 H, d); MS m/z (TS⁺) 341 (MH⁺).

EXAMPLES 111–113

The general reaction of example 110 was repeated to produce a series of amines from the requisite nitrile precursors.

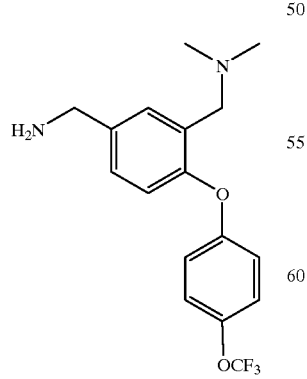

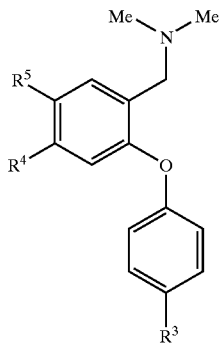

| Example | Starting Material | R⁵ | R⁴ | R³ | Data |
|---|---|---|---|---|---|
| 111 | Example 85 | H₂N⤳ | H | —SMe | δ_H (CDCl₃, 400MHz) 2.24(6H, s), 2.45(3H, s), 3.43(2H, s), 3.85(2H, s), 6.86(3H, m), 7.17(1H, dd), 7.23(2H, m), 7.41(1H, d); MS m/z(TS⁺)303(MH⁺) |
| 112 (2xHCl salt) | Example 83 | H₂N⤳ | H | —CF₃ | δ_H (d₆-DMSO, 400MHz) 2.74(6H, s), 4.00(2H, brs), 4.29(2H, s), 7.07 (1H, d), 7.16(2H, d), 7.60(1H, d), 7.80(2H, d), 7.85(1H, s), 8.47(3H, brs), 10.68(1H, brs); MSm/z (TS⁺)325(MH⁺). |
| 113 | Example 86 | H | H₂N⤳ | —OCF₃ | δ_H (CDCl₃, 300MHz) 1.53(2H, brs), 2.23(6H, s), 3.41(2H, s), 3.82(2H, s), 6.85–6.94(3H, m), 7.07–7.19 (3H, m), 7.43(1H, d); MSm/z (TS⁺)341(MH⁺) |

EXAMPLE 114

N-(3-[(Dimethylamino)methyl]-4-[4-(trifluoromethyl)phenoxy]phenyl} methanesulfonamide

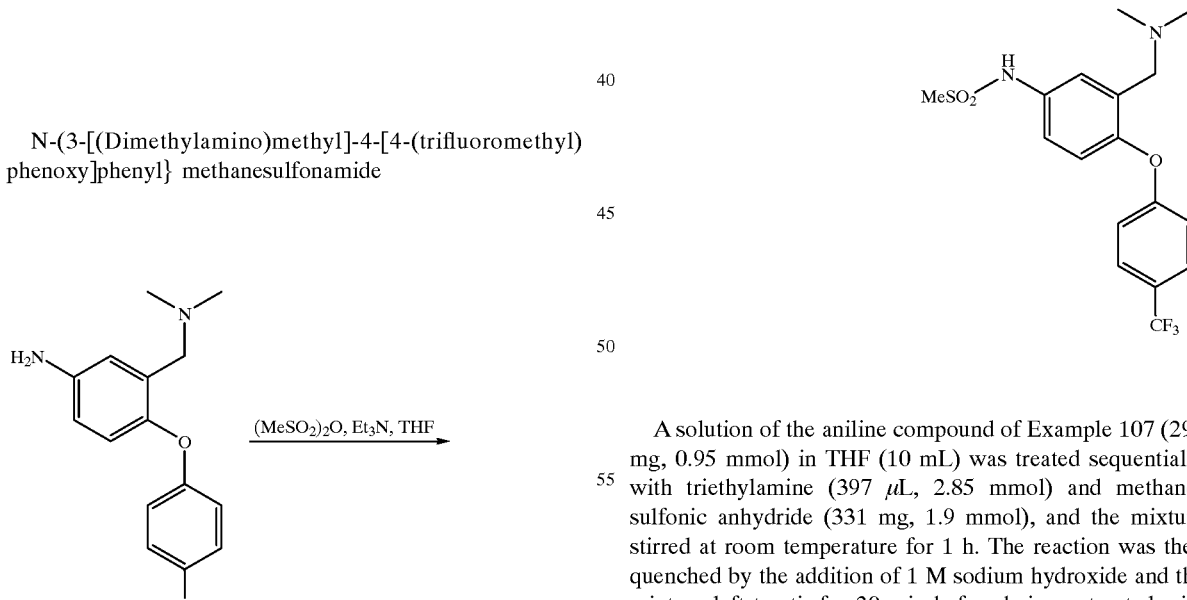

A solution of the aniline compound of Example 107 (295 mg, 0.95 mmol) in THF (10 mL) was treated sequentially with triethylamine (397 μL, 2.85 mmol) and methanesulfonic anhydride (331 mg, 1.9 mmol), and the mixture stirred at room temperature for 1 h. The reaction was then quenched by the addition of 1 M sodium hydroxide and the mixture left to stir for 30 min before being extracted with ethyl acetate. The organic layer was washed with brine, dried (MgSO₄) and evaporated to a brown oil. Purification by flash chromatography [SiO$_2$; DCM/ MeOH/ 880 NH$_3$ (95:5:1)] afforded the desired methanesulfonamide compound as a colourless oil which crystallised on standing to give a white solid (291 mg, 79%); δ$_H$(CDCl$_3$, 400 MHz) 2.22 (6 H, s), 3.05 (3 H, s), 3.39 (2 H, s), 6.95 (2 H, d), 6.95 (1 H, d), 7.21 (1 H, dd), 7.37 (1 H, d), 7.58 (2 H, d); MS m/z (TS$^+$) 389 (MH$^+$).

EXAMPLES 115–120

A series of methanesulfonamides was prepared from the requisite aniline or amine by similar procedures to that described in Example 114. In some cases methanesulfonyl chloride was used in place of the anhydride and/ or DCM was used as solvent.

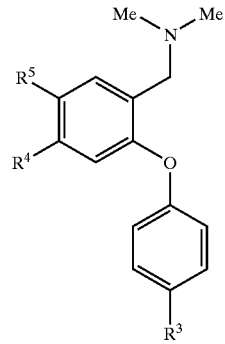

| Example | Starting Material | R$^4$ | R$^5$ | R$^3$ | Data |
|---|---|---|---|---|---|
| 115 | Example 112 | H | —CH$_2$NHSO$_2$CH$_3$ | —CF$_3$ | δ$_H$ (CDCl$_3$, 400MHz) 2.14(6H, s), 2.93(3H, s), 3.40(2H, s), 4.34 (2H, d), 4.66(1H, brs), 6.95(3H, d), 7.27(1H, d), 7.51(1H, s), 7.56 (2H, d); MSm/z (TS$^+$) 403 (MH$^+$). |
| 116 | Example 108 | H | —NHSO$_2$CH$_3$ | —OCF$_3$ | δ$_H$ (CDCl$_3$, 400MHz) 2.26(6H, s), 3.02(3H, s), 3.43(2H, s), 6.91 (3H, m), 7.18(3H, m), 7.34(1H, d); MSm/z (TS$^+$) 405(MH$^+$) |
| 117 | Example 110 | H | —CH$_2$NHSO$_2$CH$_3$ | —OCF$_3$ | δ$_H$ (CDCl$_3$, 400MHz) 2.24(6H, s), 2.92(3H, s), 3.43(2H, s), 4.32 (2H, d), 4.65(1H, br), 6.90(3H, m), 7.17(2H, m), 7.25(1H, m), 7.48 (1H, s); MSm/z(TS$^+$) 419(MH$^+$) |
| 118[b] | Example 109 | H | —NHSO$_2$CH$_3$ | —SMe | δ$_H$ (CD$_3$OD, 300MHz) 2.48(3H, s), 2.93(6H, s), 3.00(3H, s), 4.83 (2H, s), 6.90(1H, d), 7.06(2H, m), 7.31,(1H, dd), 7.37(2H, m), 7.52 (1H, d); MSm/z(TS$^+$) 367(MH$^+$) |
| 119[a] (HCl salt) | Example 111 | H | —CH$_2$NHSO$_2$CH$_3$ | —SMe | δ$_H$ (d$_6$-DMSO, 400MHz) 2.46(3H, s), 2.76(6H, d), 2.88(3H, s), 4.13 (2H, d), 4.33(2H, d), 6.80(1H, d), 7.06(2H, d), 7.33(2H, d), 7.38 (1H, d), 7.57(1H, t), 7.61(1H, s), 10.28(1H, br); MSm/z(TS$^+$) 381 (MH$^+$) |
| 120 | 113 | —CH$_2$NHSO$_2$CH$_3$ | H | —OCF$_3$ | HCL salt:(d$_6$-DMSO, 400MHz) 2.73(6H, s), 2.81(3H, s), 4.11(2H, d), 4.29(2H, s), 6.91 (1H, s), 7.20(3H, m), 7.43(2H, d), 7.60(1H, t), 7.65(1H, d), 10.18 (1H, brs); MSm/z |

-continued

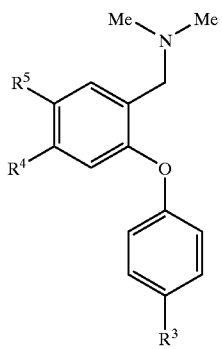

| Example | Starting Material | R[4] | R[5] | R[3] | Data |
|---------|------------------|------|------|------|------|
|         |                  |      |      |      | (TS[+]) 419 (MH[+]) |

[a]MeSO$_2$Cl (1 equivalent) was used in place of (MeSO$_2$)$_2$O and DCM was used as solvent.
[b]Excess MeSO$_2$Cl was used in place of (MeSO$_2$)$_2$O and DCM was the solvent. After work up in the usual fashion the crude product (largely bis-mesylate) was redissolved in 1,4-dioxan and treated with excess 2M NaOH$_{(aq)}$. After stirring overnight the solvent was removed in vacuo and the residue partitioned between saturated NH$_4$Cl$_{(aq)}$ and DCM. Extraction and purification was effected in the usual way.

EXAMPLE 121

N-{3-[(Methylamino)methyl]-4-[4-(trifluoromethyl)phenoxy]phenyl}-methanesulfonamide

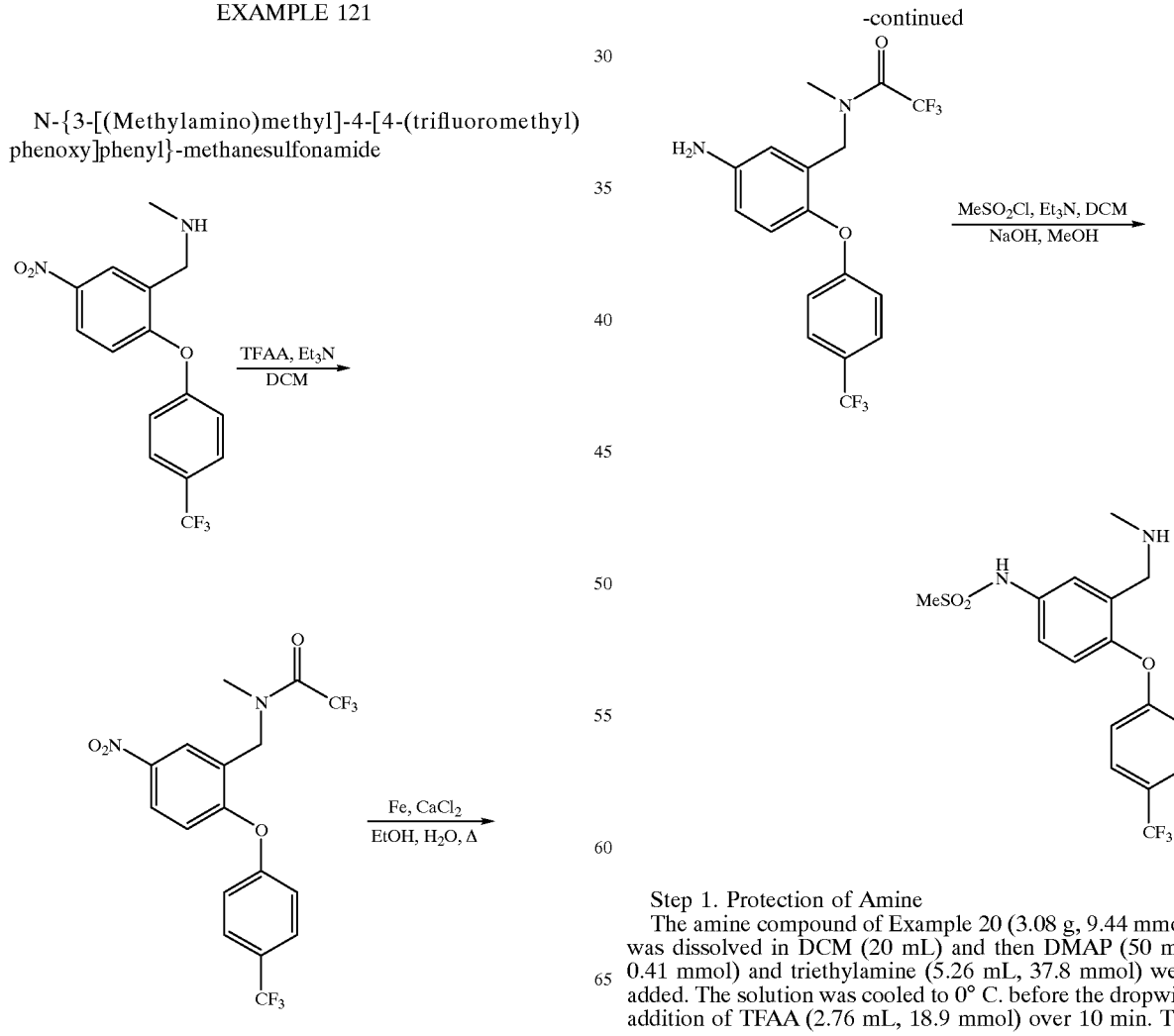

Step 1. Protection of Amine

The amine compound of Example 20 (3.08 g, 9.44 mmol) was dissolved in DCM (20 mL) and then DMAP (50 mg, 0.41 mmol) and triethylamine (5.26 mL, 37.8 mmol) were added. The solution was cooled to 0° C. before the dropwise addition of TFAA (2.76 mL, 18.9 mmol) over 10 min. The reaction was allowed to reach room temperature and stirred for a further 20 min, then quenched by the addition of methanol (3 mL). The quenched mixture was poured into 1 M hydrochloric acid (50 mL), the organic layer separated and then the aqueous layer further extracted with DCM (2×30 mL). The combined organic fractions were dried (MgSO$_4$) and evaporated to a slightly impure yellow oil (4.60 g) of the desired trifluoroacetamide, which was not purified any further. Two amide rotomers were visible in the $^1$H NMR spectrum. Data is given for the major rotomer only; $\delta_H$(CDCl$_3$, 400 MHz) 3.23 (3 H, s), 4.79 (2 H, s), 6.92 (1 H, d), 7.16 (2 H, d), 7.70 (2 H, d), 8.16 (1 H, dd), 8.23 (1 H, d); MS m/z (TS$^+$) 440 (M+NH$_4^+$).

Step 2. Iron Reduction to Aniline

The crude oil of Step 1 was dissolved in 85% aqueous ethanol (38 mL) together with calcium chloride (471 mg, 4.24 mmol) and iron powder (4.75 g, 85 mmol) was added. The mixture was heated at reflux for 18 h and then allowed to cool to room temperature. The mixture was filtered through a plug of arbocel® (washing through with DCM) and then evaporated to an oil. The oil was purified by passing through a plug of silica gel, eluting with DCM/ methanol/ 880 NH$_3$ (93:7:1), followed by evaporation to a yellow oil (3.35 g) of the desired aniline. Two amide rotomers were visible in the $^1$H NMR spectrum, which showed the material to be ca. 90% pure. Data is given for the major rotomer only; $\delta_H$(CDCl$_3$, 400 MHz) 3.04 (3 H, s), 4.51 (2 H, s), 6.66 (2 H, m), 6.84 (1 H, dd), 6.92 (2 H, d), 7.53 (2 H, d).

Step 3. Sulfonamide formation-hydrolysis

The crude oil from Step 2 was dissolved in DCM (34 mL) and triethylamine (9.48 mL, 68 mmol) was added followed by methanesulfonyl chloride (2.64 mL, 34 mmol) dropwise. The mixture was stirred for a further 30 min before being quenched by the addition of sodium hydroxide (2 M; 20 mL). The organic phase was separated and the aqueous layer was extracted further with DCM (2×30 mL). The combined organic fractions were dried (MgSO$_4$) and evaporated to an oil which was purified by flash chromatography [SiO$_2$; MeOH (0→10%) in DCM] and the resulting oil dissolved in methanol (50 mL) and treated with sodium hydroxide (2.5 g). The mixture was stirred at room temperature overnight and then at reflux for 1 h. After cooling to room temperature the mixture was acidified by the addition of acetic acide (4 mL) and then 880 ammonia was added (100 mL). The organic layer was separated and the aqueous layer extracted with DCM (2×50 mL). The combined organic fractions were dried (MgSO$_4$) and evaporated to an orange oil. The oil was extracted into hydrochloric acid (2 M) (100 mL) and the aqueous layer washed with diethyl ether (2×50 mL). The acid was neutralised by pouring cautiously into 880 ammonia (200 mL) and the mixture extracted with DCM (3×100 mL). After drying (MgSO$_4$) and evaporation the residue was purified by flash chromatography [SiO$_2$; DCM/ MeOH/ 880 NH$_3$ (93:7:1)] to afford the desired sulfonamide compound as a solid (330 mg, 10%) which was further purified by trituration with diethyl ether/ pentane to afford the desired sulfonamide compound as a cream powder (250 mg); $\delta$ (CDCl$_3$, 400 MHz) 2.43 (3 H, s), 3.02 (3 H, s), 3.71 (2 H, s), 6.93 (1 H, d), 6.94 (2 H, d), 7.18 (1 H, dd), 7.31 (1 H, d), 7.57 (2 H, d); MS m/z (TS$^+$) 375 (MH$^+$).

EXAMPLE 122

N-{3-[{Dimethylamino)methyl]-4-[4-(trifluoromethyl) phenoxy]phenyl}-N-(2-hydroxyethyl)methanesulfonamide

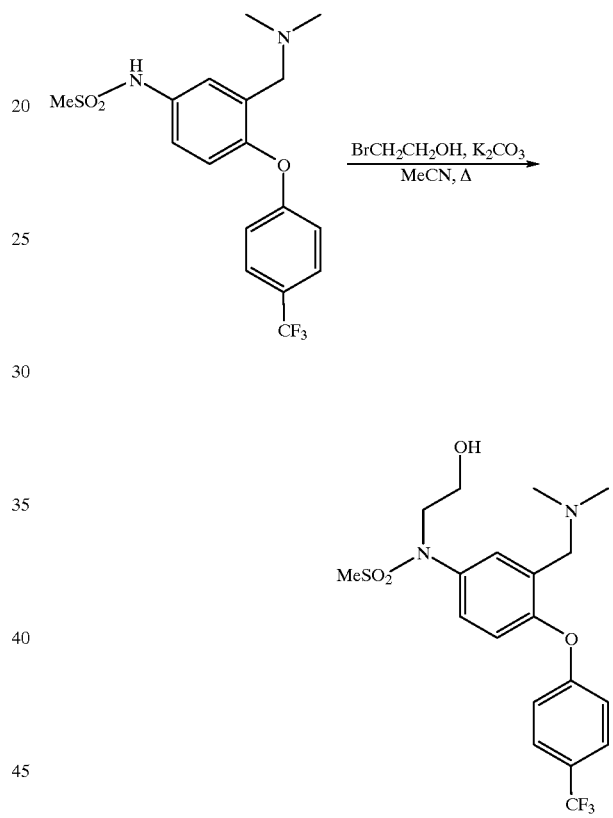

The methanesulfonamide compound of Example 114 (131 mg, 0.34 mmol), 2-bromoethanol (36 μL, 0.51 mmol), and potassium carbonate (70 mg, 0.51 mmol) were heated at reflux in acetonitile (2 mL). After 1.5 h a further portion of 2-bromoethanol (20 μL, 0.28 mmol) was added and refluxing continued for a further 2.5 h. After cooling to room temperature the mixture was evaporated to a yellow oil. Purification of the mixture by flash chromatography afforded the desired hydroxyethyl sulfonamide compound as a colourless oil (28 mg, 19%) in addition to returned starting material (methanesulfonamide of Example 67) (19.4 mg, 15%) and mixed fractions (58 mg). Desired compound: $\delta_H$(CDCl$_3$, 300 MHz) 2.23 (6 H, s), 3.00 (3 H, s), 3.43 (2 H, s), 3.70 (2 H, t), 3.85 (2 H, t), 6.95 (1 H, d), 7.00 (2 H, dd), 7.28 (1 H, dd), 7.58 (1 H, d), 7.59 (2 H, d); MS m/z (TS$^+$) 433 (MH$^+$).

EXAMPLE 123

N-{3-(Aminomethyl)-4-[4-(methylsulfanyl)phenoxy]phenyl}-N-(2-hydroxyethyl)-methanesulfonamide

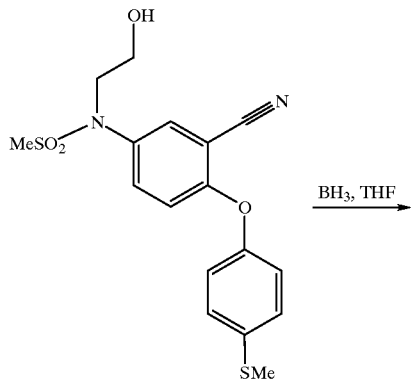

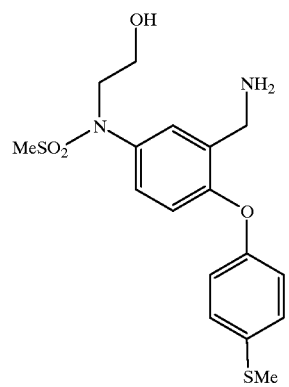

Borane-tetrahydrofuran complex (1 M soln in THF, 7.5 mL, 7.5 mmol) was added to a solution of the nitrile from preparation 66 (1.9 g, 5.02 mmol) in THF (40 μL) under $N_2$ and the mixture was heated at reflux for 20 h. TLC analysis indicated starting material remaining so a further portion of borane-tetrahydrofuran complex (1 M soln in THF, 7.5 mL, 7.5 mmol) was added and reflux was continued for 2 h. After cooling to room temperature hydrochloric acid (6 M; 10 mL) was added and the mixture was heated at reflux for 1 h. The mixture was re-cooled, basified with sodium hydroxide (2 M) and extracted with ethyl acetate (100 mL), the organic extract being washed with brine, dried ($MgSO_4$) and evaporated. The residue was taken up in ethyl acetate (50 mL) and extracted with hydrochloric acid (2 M) (50 mL+2×25 mL). The combined aqueous extracts were basified with sodium hydroxide (5 M) (50 mL) and extracted with DCM (3×40 mL), the organic extracts being dried ($MgSO_4$) and evaporated. The residue was purified by column chromatography [$SiO_2$; DCM/methanol/880 $NH_3$ (95:5:0.5))] to give the title compound; $\delta_H$(CDCl$_3$, 400 MHz) 2.44 (3 H, s), 2.97 (3 H, s), 3.67 (2 H, t), 3.79 (2 H, m), 3.88 (2 H, s), 6.78 (1 H, d), 6.91 (2 H, d), 7.15 (1 H, dd), 7.23 (2 H, d), 7.39 (1 H, d); MS m/z (ES$^+$) 383 (MH$^+$).

EXAMPLE 124

N-{3-(Aminomethyl)-4-[4-(methylsulfanyl)-3-(trifluoromethyl)phenoxy]phenyl}-methanesulfonamide

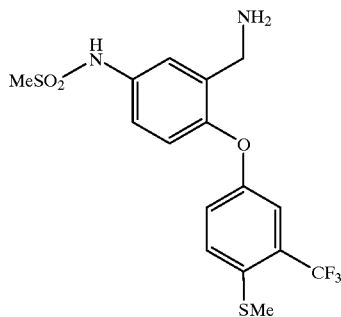

The title compound was prepared from the nitrile of preparation 64 using the method described for Example 123 $\delta_H$(CDCl$_3$, 400 MHz) 2.48 (3 H, s), 3.01 (3 H, s), 3.87 (2 H, s), 6.93 (1 H, d), 7.05 (1 H, d), 7.17 (1 H, d), 7.27 (1 H, obs), 7.30 (1 H, s), 7.39 (1 H, d); MS m/z (TS$^+$) 407 (MH$^+$).

EXAMPLE 125

N-{3-(Aminomethyl)-4-[4-(methylsulfanyl)phenoxy]phenyl}methanesulfonamide

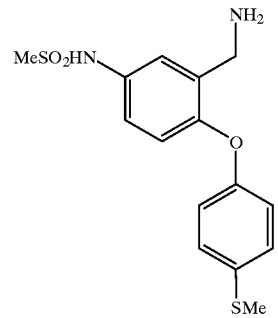

Lithium aluminium hydride (1 M soln in THF, 6 mL, 6 mmol) was added to a solution of the nitrile of preparation 62 (1.01 g, 3.02 mmol) in THF (30 mL) under nitrogen and the mixture was heated at reflux for 3 h. After cooling to room temperature the reaction was quenched by the cautious addition of sodium hydroxide (2 M; 2 mL). The reaction mixture was dried ($MgSO_4$), filtered and concentrated in vacuo. The residue was purified by column chromatography [$SiO_2$; DCM/MeOH/880 $NH_3$ (93:7:1)] to give an off-white powder (805 mg, 79%); $\delta_H$(DMSO-D$_6$, 400 MHz) 2.39 (3 H, s), 2.47 (3 H, s), 2.93 (3 H, s), 3.58 (2 H, s), 6.82 (3 H, m), 7.02 (1 H, dd), 7.21 (2 H, d), 7.35 (1 H, d); MS m/z (TS$^+$) 339 (MH$^+$).

EXAMPLE 126

N-{3-(Aminomethyl)-4-[4-(methylsulfanyl)phenoxy]phenyl}-N-methylmethanesulfonamide

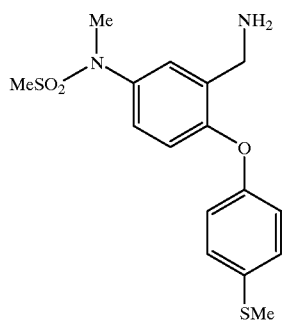

Lithium aluminium hydride (1 M soln in THF, 15 mL, 15 mmol) was added to a solution of the nitrile of preparation 65 (2.75 g, 7.89 mmol) in THF (50 mL) under $N_2$ and the mixture was heated at reflux for 2 h. After cooling to room temperature the reaction was quenched by the cautious addition of sodium hydroxide (2 M; 3 mL). After stirring for 10 min the reaction mixture was dried (MgSO$_4$), filtered and concentrated in vacuo. The residue was purified by multiple column chromatography [SiO$_2$; DCM/(10% 880 ammonia in methanol) 94:6] to give the product as an oil (783 mg, 28%). A sample was taken up in DCM and converted to the HCl salt by the addition of 1 M ethereal HCl. Removal of the solvent and drying in vacuo gave an off-white foam; $\delta_H$(DMSO-D$_6$, 400 MHz) 2.44 (3 H, s), 2.95 (3 H, s), 3.16 (3 H, s), 4.04 (2 H, q), 6.74 (1 H, d), 7.04 (2 H, d), 7.31 (3 H, m), 7.60 (1 H, s), 8.30 (3 H, br); MS mz (ES$^+$) 353 (MH$^+$).

EXAMPLE 127

N-{3-(Aminomethyl)-4-[3-methoxy-4-(methylsulfanyl)phenoxy]phenyl}-methanesulfonamide

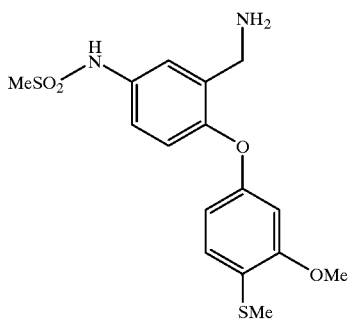

The procedure for example 126 was repeated using the product of preparation 63 to provide the title amine; $\delta_H$(CDCl$_3$, 400 MHz) 2.33 (3 H, s), 2.94 (3 H, s), 3.78 (3 H, s), 3.93 (2 H, s), 6.50 (1 H, dd), 6.67 (1 H, s), 7.12–7.18 (2 H, m), 7.33 (1 H, d).

EXAMPLE 128

N-{3-[(Methylamino)methyl]-4-[4-(methylsulfanyl)phenoxy]phenyl}methanesulfonamide

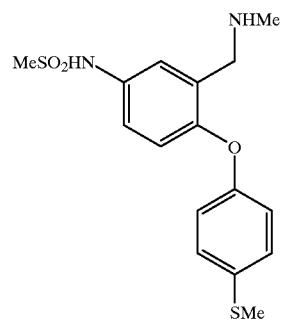

Formic acid (55 μL, 1.46 mmol) was added to a solution of pentafluorophenol (240 mg, 1.30 mmol) in ether (5 mL) at 0° C. followed by dicyclohexylcarbodiimide (270 mg, 1.31 mmol). The mixture was stirred at 0° C. for 15 min and at room temperature for 2 h before being filtered, the residue being washed with ether. The ethereal solution of pentafluorophenyl formate was added to a suspension of the amine from Example 125 (221 mg, 0.65 mmol) in DCM (7 mL) and the mixture was stirred at room temperature for 18 h before being diluted with DCM (40 mL) and washed with sat. aq NaHCO$_3$ (50 mL). The organic layer was dried and evaporated to give a crude formamide which was used without further purification. The crude formamide (0.65 mmol) was taken up in dry THF (10 mL), borane-tetrahydrofuran complex (1 M soln in THF, 2 mL, 2 mmol) was added and the mixture was heated at reflux for 1.5 h. After cooling to room temperature hydrochloric acid (6 M; 5 mL) was added and the mixture was stirred for 15 min before being neutralised with satuarated aqueous sodium bicarbonate solution (50 mL). The aqueous mixture was extracted with DCM (2×30 mL) and the organic extracts were dried (MgSO$_4$) and evaporated. Purification of the residue by column chromatography [SiO$_2$; EtOAc/MeOH/880 NH$_3$ (95:5:0.5 increasing polarity to 90:9:1)] gave the product as a colourless oil. This was taken up in DCM (5 mL) and converted to the hydrochloride salt by the addition of 1 M ethereal hydrochloric acid. Removal of the solvent and drying in vacuo gave an off-white foam (218 mg, 86%); $\delta_H$(CD$_3$OD, 300 MHz) 2.48 (3 H, s), 2.77 (3 H, s), 2.99 (3 H, s), 4.28 (2 H, s), 6.87 (1 H, d), 7.06 (2 H, d), 7.25 (1 H, dd), 7.35 (2 H, d), 7.49 (1 H, d); MS m/z (ES$^+$) 353 (MH$^+$).

EXAMPLES 129–131

Examples 129–131 were prepared from the requisite primary amines according to the method described for Example 128.

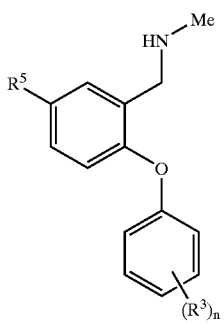

| Example | Starting Material | R⁵ | (R³)ₙ | Data |
|---|---|---|---|---|
| 129(HCl salt) | Example 126 | MeSO₂-N(Me)-CH₂- | 4-SMe | $\delta_H$(CD₃OD, 300MHz) 2.48(3H, s), 2.78 (3H, s), 2.93(3H, s), 3.29(3H, s), 4.32 (2H, s), 6.88(1H, d), 7.09(2H, d), 7.38 (2H, d), 7.47(1H, dd), 7.59(1H, d); MS m/z(ES⁺) 367(MH⁺). |
| 130 | Example 123 | MeSO₂-N(CH₂CH₂OH)- | 4-SMe | $\delta_H$(CDCl₃, 300MHz) 2.45(3H, s), 2.48 (3H, s), 2.99(3H, s), 3.69(2H, m), 3.82 (4H, m), 6.81(1H, d), 6.94(2H, d), 7.20 (1H, dd), 7.28(2H, d), 7.44(1H, d); MS m/z(TS⁺) 397(NH⁺). |
| 131 | Example 127 | MeSO₂-N(H)-CH₂- | 3-OMe, 4-SMe | $\delta_H$(CD₃OD, 400MHz) 2.39(3H, s), 2.79 (3H, s), 3.99(3H, s), 3.83(3H, s), 4.29 (2H, s), 6.65(1H, dd), 6.77(1H, d), 6.91 (1H, d), 7.19(1H, d), 7.25(1H, dd), 7.47 (1H, d); MSm/z(TS⁺) 400(MNH₄⁺) |

EXAMPLE 132

N-{3-[(Dimethylamino)methyl]-4-[4-(methylsulfanyl)phenoxy]phenyl}-N-(2-hydroxyethyl)methanesulfonamide

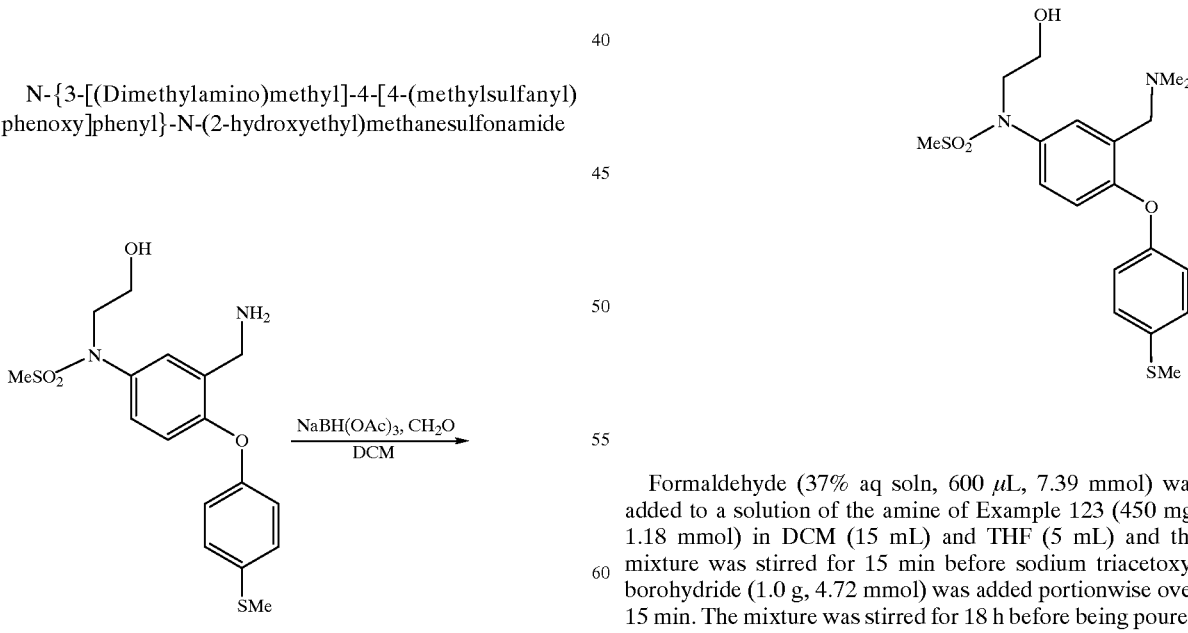

Formaldehyde (37% aq soln, 600 μL, 7.39 mmol) was added to a solution of the amine of Example 123 (450 mg, 1.18 mmol) in DCM (15 mL) and THF (5 mL) and the mixture was stirred for 15 min before sodium triacetoxyborohydride (1.0 g, 4.72 mmol) was added portionwise over 15 min. The mixture was stirred for 18 h before being poured into aqueous potassium carbonate (10%; 50 mL) and extracted with DCM (2×30 mL). The organic layer was dried (MgSO$_4$) and evaporated, and the residue was purified by column chromatography [SiO$_2$; DCM/MeOH/880 NH$_3$ (90:9:1)] to give the product as an oil. This was taken up in DCM and converted to the hydrochloride salt by the addition of 1 M ethereal hydrochloric acid Removal of the solvent and drying in vacuo gave an off-white foam (362 mg, 69%); $\delta_H$ (CDCl$_3$, 400 MHz) 2.50 (3 H, s), 2.86 (6 H, d), 3.12 (3 H, s), 3.70 (2 H, m), 3.84 (2 H, m), 4.31 (2 H, d), 6.82 (1 H, d), 6.96 (2 H, d), 7.30 (2 H, d), 7.41 (1 H, dd), 8.18 (1 H, d), 12.5 (1 H, br); MS m/z (ES$^+$) 411 (MH$^+$).

EXAMPLE 133–136

The examples below were prepared from the requisite primary amine by the method described in Example 132.

| Example | Starting Material | R$^5$$_n$ | (R$^3$) | data |
|---|---|---|---|---|
| 133 | Example 127 | MeSO$_2$HN— | 3-OMe, 4-SMe | $\delta_H$(CD$_3$OD, 400MHz)2.39(3H, s), 2.92 (6H, s), 2.98(3H, s), 3.84(3H, s), 4.41 (2H, s), 6.65(1H, dd), 6.77(1H, d), 6.93 (1H, d), 7.22(1H, d), 7.29(1H, dd), 7.51 (1H, d); MSm/z(TS$^+$)397(MH$^+$) |
| 134 | Example 124 | MeSO$_2$HN— | 3-CF$_3$, 4-SMe | HCl salt: $\delta_H$(d$_6$-DMSO, 400MHz)2.55 (3H, s), 2.76(6H, d), 3.05(3H, s), 4.28 (2H, d), 6.97(1H, d), 7.22(1H, d), 7.31 (1H, d), 7.45(1H, s), 7.59(1H, d), 9.88 (1H, s), 10.25(1H, brs) |
| 135 | Example 192 | —Cl | 4-SMe | $\delta_H$(CDCl$_3$, 400MHz)2.49(3H, s), 2.81 (6H, s), 4.27(2H, s), 6.79(1H, d), 6.94 (2H, d), 7.27(2H, d), 7.31(1H, dd), 7.80 (1H, d); MSm/z(TS$^+$)308.310(MH$^+$). |
| 136 (HCl salt) | Example 126 | MeSO$_2$-N(Me)— | 4-SMe | $\delta_H$(CDCl$_3$, 400MHz)2.50(3H, s), 2.82 (6H, d), 3.01(3H, s), 3.38(3H, s), 4.30 (2H, d), 6.81(1H, d), 6.95(2H, d), 7.30 (2H, d), 7.44(1H, d), 8.21(1H, s), 12.92 (1H, br); MSm/z(TS$^+$)381(MH$^+$). |

EXAMPLE 137

N-{3-[(Dimethylamino)methyl]-4-[4-(methylsulfanyl)phenoxy]phenyl}-2-methoxyethanesulfonamide

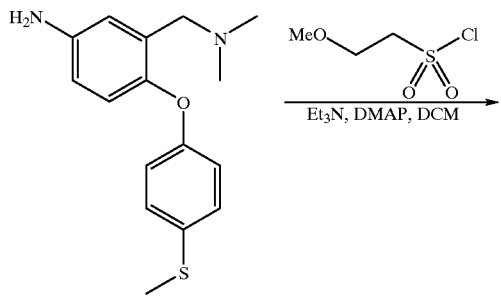

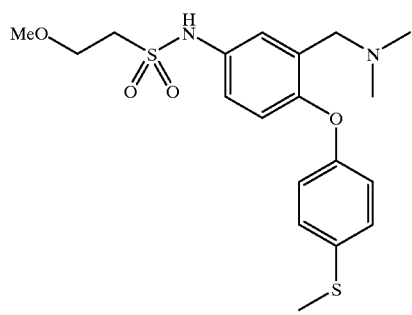

The aniline of Example 109 (350 mg, 1.08 mmol) was dissolved in DCM (10 mL) and treated with 4,4-dimethylaminopyridine (132 mg, 1.08 mmol), triethylamine (0.68 mL, 4.86 mmol) and 2-(methoxy)ethylsulfonyl chloride [prepared according to EP 0446845]. The reaction mixture was stirred at room temperature overnight The mixture was evaporated to remove volatiles and the residue treated with sodium hydroxide (2 M; 5 mL) and dioxan (5 mL). The mixture was stirred for 3 hours and then evaporated once more to remove most of the dioxan. The aqueous residue was extracted with dichloromethane (2×30 mL) and the combined extracts dried (MgSO$_4$) and evaporated. The residue was purified by flash chromatography [SiO$_2$; DCM/MeOH (95:5→90:10)] to afford the title compound, which was isolated as the HCl salt (20 mg, 4%); HCl salt: $\Delta_H$ (CD$_3$OD, 400 MHz) 2.44 (3 H, s), 2.88 (6 H, s), 3.28 (3 H, s), 3.30 (2 H, t), 3.74 (2 H, t), 4.38 (2 H, s), 6.85 (1 H, d), 7.02 (2 H, d), 7.25 (1 H, dd), 7.31 (2 H, d), 7.48 (1 H, d); MS m/z (ES$^+$) 411 (MH$^+$).

EXAMPLE 138

N-{3-[(Dimethylamino)methyl]-4-[4-(methylsulfanyl)phenoxy]phenyl}-ethanesulfonamide

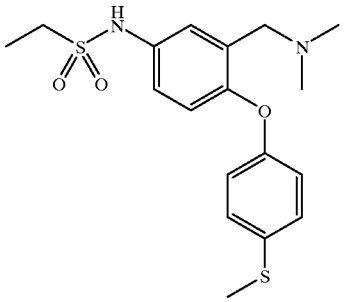

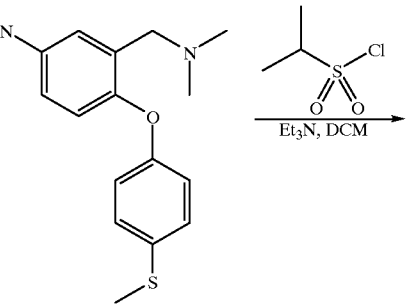

The title compound was prepared from the aniline of Example 109 according to the general procedure described in example 114, using ethanesulfonyl chloride in place of methanesulfonyl chloride. HCl salt:□$\delta_H$ (d$_6$-DMSO, 300 MHz) 1.20 (3 H, t), 2.47 (3 H, s), 2.75 (6 H, s), 4.30 (1 H, brs), 6.85 (1 H, d), 7.06 (2 H, d), 7.22 (1 H, dt), 7.37 (2 H, d), 7.53 (1 H, m), 9.84 (1 H, s), 10.50 (1 H, brs); MS m/z (ES$^+$) 381 (MH$^+$)

EXAMPLE 139

N-{3-[(Dimethylamino)methyl]-4-[4-(methylsulfanyl)phenoxy]phenyl}-2-propanesulfonamide

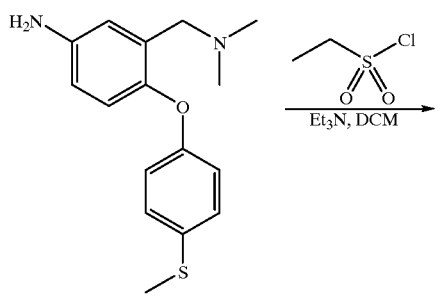

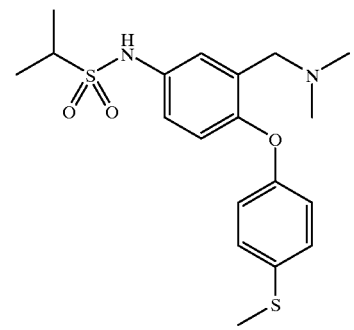

The compound was prepared from the aniline of Example 109 according to the general procedure described in example 114, using 2-propylsulfonyl chloride in place of methanesulfonyl chloride. HCl salt: $\delta_H$ (d$_6$-DMSO, 400 MHz) 1.23 (6 H, d), 2.45 (3 H, s), 2.73 (6 H, d), 3.33 (1 H, m), 4.28 (2 H, d), 6.87 (1 H, d), 7.04 (1 H, d), 7.22 (1 H, dd), 7.54 (1 H, d), 9.83 (1 H, s), 10.30 (1 H, brs); MS m/z (ES$^+$) 395 (MH$^+$)

EXAMPLE 140

N-{3-[(Dimethylamino)methyl]-4-[4-(methylsulfanyl)phenoxy]phenyl}-(trifluoro)methanesulfonamide

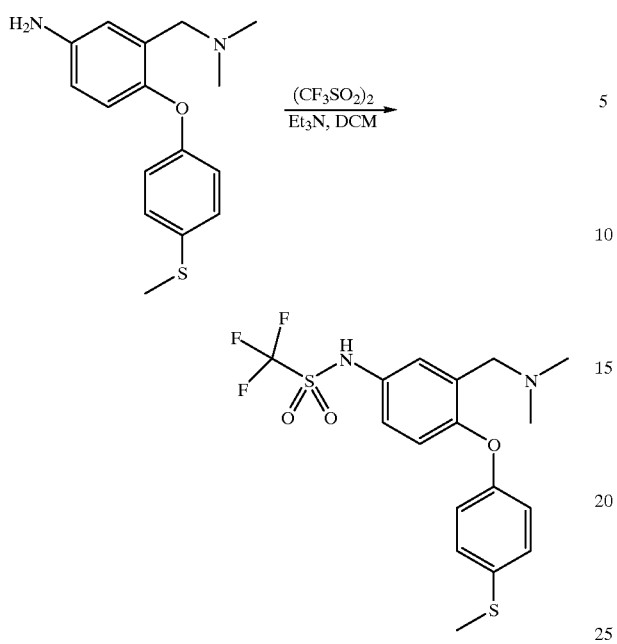

The aniline from example 109 (300 mg, 0.9 mmol) was dissolved in DCM (10 mL) and treated with trifluoromethanesulfonic anhydride (169 µL, 1.02 mmol) at 0° C. The mixture was stirred at this temperature for 3 hours and then the solvents removed by evaporation. The residue was purified by flash chromatography [SiO$_2$; DCM/ MeOH (100:0→90:10)] to afford a yellow solid. Trituration with DCM afforded the title compound as a white solid (80 mg, 21%); Free base: $\delta_H$ (d$_6$-DMSO, 400 MHz) 2.40 (3 H, s), 2.70 (6 H, s), 4 10 (2 H, s), 6.67 (1 H, d), 6 89 (2 H, d), 7.00 (1 H, dd), 7.09 (1 H, s), 7.24 (2 H, d), 9.33 (1 H, brs); MS m/z (TS$^+$) 421 (MH$^+$).

EXAMPLE 141

N,N-Dimethyl-N-{5-(methylsulfanyl)-2-[4-(trifluoromethoxy)phenoxy]benzyl}amine

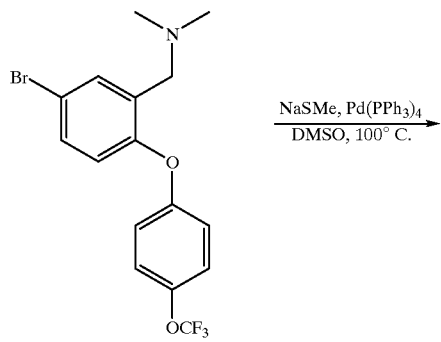

A solution of the bromide compound of Example 7 (1.6 g, 4.1 mmol) and palladium tetrakis(triphenylphosphine) (237 mg, 0.21 mmol) in DMSO (40 mL) was stirred at 100° C. under nitrogen for 90 min. Sodium thiomethoxide (575 mg, 8.2 mmol) was added in one portion and the reaction was stirred at 100° C. for 64 h. After cooling to room temperature the reaction mixture was poured into water and extracted with ethyl acetate (4 times). The combined organic extracts were dried (MgSO$_4$) and concentrated in vacuo. The residue was purified by flash chromatography [SiO$_2$; DCM/ MeOH/ 880 NH$_3$ (97:3:0.5→93:7:1)]. The relevant fractions were combined and repurified by flash chromatography [SiO$_2$; ethyl acetate/methanol/ 880 ammonia (96:4:0.4)] to give the desired sulfide compound (930 mg, 63%); $\delta_H$ (CDCl$_3$, 400 MHz) 2.24 (6 H, s), 2.49 (3 H, s), 3.39 (2 H, s), 6.87 (3 H, m), 7.14 (3 H, m), 7.42 (1 H, s); MS m/z (TS$^+$) 358 (MH$^+$).

EXAMPLES 142–144

The reaction described in Example 141 was repeated under similar conditions to provide a series of sulfides from the requisite bromide or iodide. Data for these compounds are compiled below.

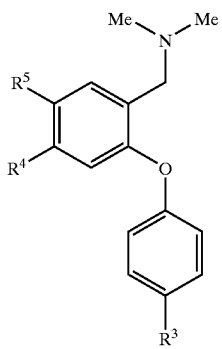

| Example | Starting Material | R⁵ | R⁴ | R³ | ¹H NMR Data |
|---|---|---|---|---|---|
| 142 | Example 8 | H | —SMe | —OCF₃ | $\delta_H$(CDCl₃, 400MHz)2.23(6H, s), 2.42 (3H, s), 3.39(2H, s), 6.79(1H, s), 6.90 (2H, d), 7.05(2H, d), 7.15(2H, d), 7.39 (1H, d); 358(MH⁺) |
| 143 | Example 18 | MeS— | H | —CF₃ | $\delta_H$(CDCl₃, 400MHz)2.06(6H, s), 2.50 (3H, s), 3.36(2H, s), 6.90(1H, d), 6.93 (2H, d), 7.17(1H, d), 7.44(1H, s), 7.53 (2H, d); MSm/z(ES⁺)342(MH⁺). |
| 144 | Example 12 | H | EtS— | —CF₃ | $\delta_H$(CDCl₃, 400MHz)1.29(3H, t), 2.22 (6H, s), 2.89(2H, q), 3.33(2H, s), 6.90 (1H, s), 6.95(2H, d), 7.14(1H, d), 7.41 (1H, d), 7.56(2H, d); MSm/z(TS⁺)356 (MH⁺). |

EXAMPLES 145–146

N,N-Dimethyl-N-{5-(methylsulfonyl)-2-[4-(trifluoromethoxy)phenoxy]benzyl}amine (Example 145) and N,N-dimethyl-N-{5-(methylsulfinyl)-2-(4-(trifluoromethoxy)phenoxy]benzyl}amine (Example 146)

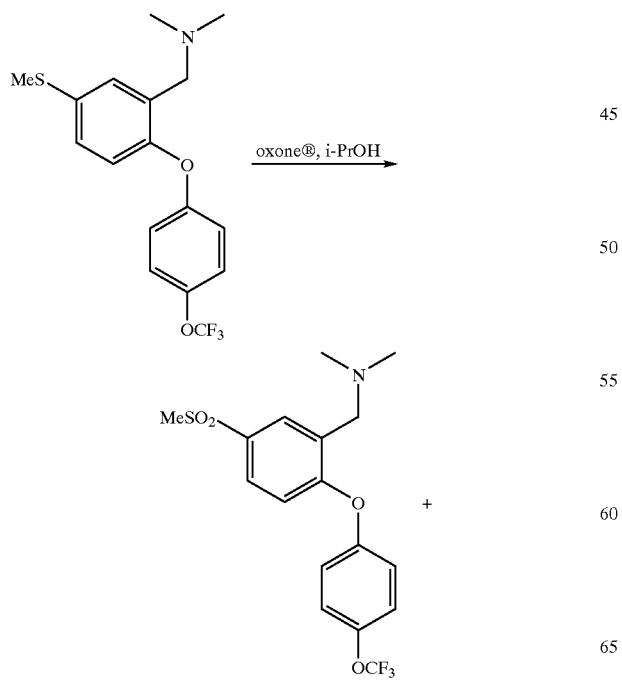

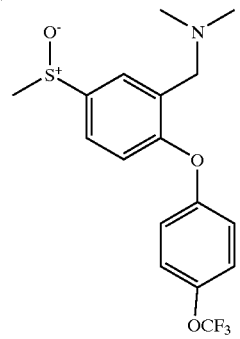

Oxone® (1.54 g, 2.50 mmol) was added to a solution of the compound of Example 141 (900 mg, 2.52 mmol) in THF (4 mL), isopropyl alcohol (20 mL) and water (2 mL) at 0° C. The mixture was stirred at 0–5° C. for 15 min then allowed to warm to room temperature over 25 min before being quenched with sodium hydroxide (2 M). The aqueous mixture was extracted with ethyl acetate (3 times) and the combined organic extracts were dried (MgSO₄) and concentrated in vacuo. The residue was purified by flash chromatography [SiO₂; DCM/methanol/ 880 ammonia (97:3:0.5→93:7:1)] to give two major products. Fractions containing the higher running product were combined and repurified by flash chromatography [SiO₂; ethyl acetate/ methanol/ 880 ammonia (96:4:0.4)] to give the sulfone of Example 145 (473 mg, 48%) as a colourless solid; $\delta_H$ (CDCl₃, 400 MHz) 2.30 (6 H, s), 3.07 (3 H, s), 3.58 (2 H, s), 6.92 (1 H, d), 7.02 (2 H, m), 7.25 (2 H, m), 7.78 (1 H, dd), 8.12 (1 H, d); MS m/z (TS⁺) 390 (MH⁺).

Fractions containing the lower running product were combined and repurified by flash chromatography [SiO₂;

EtOAc/ MeOH/ 880 NH₃ (95:5:0.5)] to give the sulfoxide of Example 146 (64 mg, 7%) as a colourless oil; $\delta_H$ (CDCl₃, 400 MHz) 2.29 (6 H, s), 2.76 (3 H, s), 3.56 (2 H, s), 6.99 (3 H, m), 7.20 (2 H, m), 7.57 (1 H, dd), 7.78 (1 H, d); MS m/z (TS⁺) 374 (MH⁺).

EXAMPLES 147–148

The reaction of Examples 145 and 146 was repeated to provide the sulfoxides of Examples 147 and 148 from the corresponding sulfides.

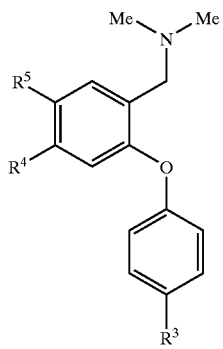

| Example | Starting Material | R⁵ | R⁴ | R³ | Data |
|---|---|---|---|---|---|
| 147 | Example 143 | —SOMe | H | CF₃ | $\delta_H$(CDCl₃, 400MHz) 2.25(6H, s), 2.75 (3H, s), 3.49(2H, s), 7.01(2H, d), 7.06 (1H, d), 7.57–7.60(3H, m), 7.80(1H, s); MSm/z(TS⁺)358(MH⁺). |
| 148 | Example 144 | H | —SOEt | CF₃ | $\delta_H$(CDCl₃, 400MHz) 1.16–1.20(3H, m), 2.25(6H, s), 2.63(1H, dq), 2.87(1H, dq), 3.43–3.49(2H, m), 6.98(2H, d), 7.23 (1H, s), 7.38(1H, d), 7.57(2H, d), 7.68 (1H, d); MSm/z(TS⁺)372 (MH⁺). |

EXAMPLE 149

N,N-Dimethyl-N-{4-(methylsulfinyl)-2-[4-(trifluoromethoxy)phenoxy]benzyl}amine

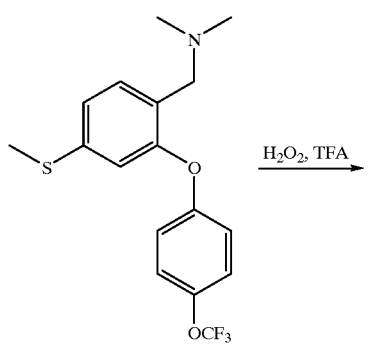

-continued

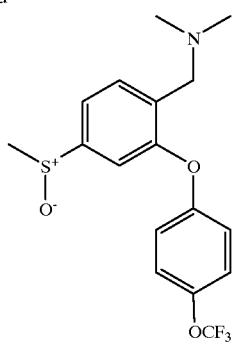

Hydrogen peroxide (30%, 76 μL, 0.67 mmol) was added dropwise to a solution of the sulfide compound of Example 142 (240 mg, 0.67 mmol) in TFA (2 mL) at 0° C. under nitrogen. After stirring at 0° C. for 30 min the reaction mixture was diluted with water and carefully basified with sodium hydroxide pellets. The mixture was extracted with ethyl acetate and the organic extract was washed with brine, dried (MgSO₄) and concentrated in vacuo. The residue was purified by flash chromatography [SiO₂; DCM/ MeOH/ 880 NH₃ (97:2.5:0.5→95:5:0.5)] to give the desired sulfoxide compound (142 mg, 57%) as a colourless oil; $\delta_H$ (CDCl₃, 400 MHz) 2.27 (6 H, s), 2.70 (3 H, s), 3.50 (2 H, s), 6.95 (2

H, d), 7.19 (2H ,d), 7.21 (1 H, s), 7.37 (1 H, d), 7.67 (1 H, d); MS m/z (TS⁺) 374 (MH⁺).

EXAMPLE 150

N,N-Dimethyl-N-{4-(methylsulfonyl)-2-[4-(trifluoromethoxy)phenoxy]benzyl}amine

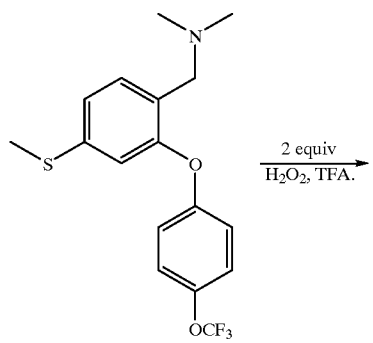

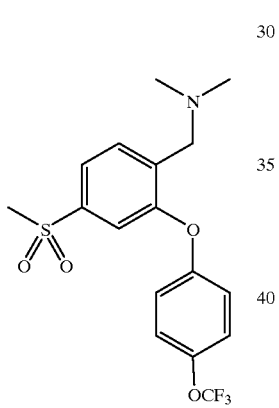

Hydrogen peroxide (30%, 160 μL, 1.41 mmol) was added dropwise to a solution of the sulfide compound of Example 142 (252 mg, 0.71 mmol) in TFA (2 mL) at 0° C. under nitrogen. After stirring at 0° C. for 60 min and room temperature for 30 min a further portion of hydrogen peroxide (80 mL, 0.71 mmol) was added and the mixture was stirred at room temperature for another 6 hrs. The reaction mixture was diluted with aqueous sodium hydroxide (1 M) and carefully basified further with sodium hydroxide pellets. The mixture was extracted with ethyl acetate and the organic extract was washed with brine, dried (MgSO₄) and concentrated in vacuo. The residue was purified by flash chromatography [SiO₂; DCM/ MeOH/ 880 NH₃ (99:1:0.5→98:2:0.5) to give the desired sulfone compound (183 mg, 67%) as a colourless oil; $\delta_H$(CDCl₃, 400 MHz) 2.30 (6 H, s), 3.00 (3 H, s), 3.55 (2 H, s), 6.97 (2 H, d), 7.20 (2 H, d), 7.42 (1 H, s), 7.70 (1 H, s), 7.78 (1 H, d) 390 (MH⁺).

EXAMPLE 151

Methyl 3-[(dimethylamino)methyl]-4-[4-(trifluoromethyl)phenoxy]benzoate

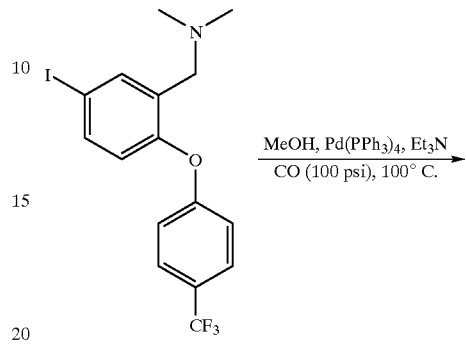

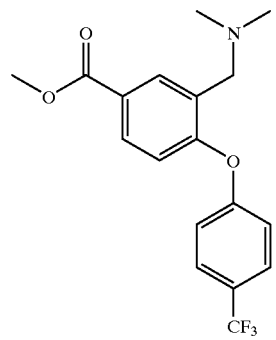

The iodide compound of Example 18 (2.0 g, 4.75 mmol) was dissolved in methanol (30 mL) and treated with triethylamine (0.98 mL, 7.04 mmol) and palladium tetrakis (triphenylphosphine) (0.28 g, 0.25 mmol). The reaction mixture was placed under an atmosphere of carbon monoxide (100 psi) and heated to 80° C. with stirring. After 6 h the pressure was released and the reaction mixture allowed to cool to room temperature. The mixture was diluted with brine and extracted with ethyl acetate to provide, after drying with MgSO₄ and evaporation, an orange solid. Purification by flash chromatography [SiO₂; MeOH/880 NH₃; (10:1) (1→3%) in DCM] gave the desired ester compound as an orange oil (1.66 g, 99%); $\delta_H$(CDCl₃, 400 MHz) 2.27 (6 H, s), 3.49 (2 H, s), 3.91 (3 H, s), 6.83 (1 H, d), 7.03 (2 H, d), 7.60 (2 H, d), 7.93 (1 H, dd), 8.19 (1 H, d); MS m/z (TS⁺) 354 (MH⁺).

EXAMPLE 152

Methyl 3-[(dimethylamino)methyl]-4-[4-(methylsulfanyl)phenoxy]benzoate

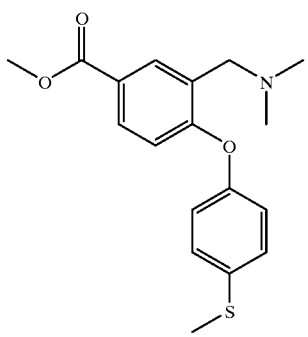

The reaction of example 151 was repeated in a similar fashion with the bromide of Example 9 to provide the title ester. Free base: $\delta_H$(CDCl$_3$, 400 MHz) 2.47 (9 H, s), 3.78 (2 H, s), 3.87 (3 H, s), 6.80 (1 H, d), 6.95 (2 H, d), 7.26 (2 H, d), 7.88 (1 H, d), 8.17 (1 H, d); MS m/z (TS$^+$) 354 (MH$^+$).

EXAMPLE 153

Methyl 3-[(methylamino)methyl]-4-[4-(methylsulfanyl) phenoxy]benzoate

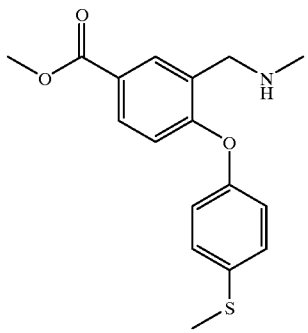

The title ester was prepared from the bromide of example 23 using the procedure described for example 151; $\delta_H$(CDCl$_3$, 400 MHz) 2.46 (3 H, s), 2.49 (3 H, s), 3.86 (2 H, s), 3.89 (3 H, s), 6.79 (1 H, d), 6.95 (2 H, d), 7.29 (2 H, d), 7.86 (1 H, dd), 8.07 (1 H, d); MS m/z (TS$^+$) 318 (MH$^+$).

EXAMPLE 154

{3-[(Dimethylamino)methyl]-4-[4-(trifluoromethyl) phenoxy]phenyl}methanol

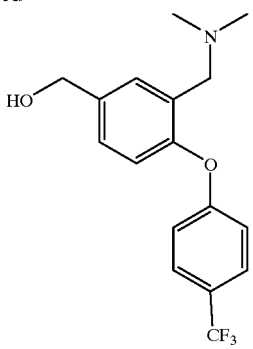

A solution of lithium aluminium hydride in THF (1 M, 7 mL, 7 mmol) was added dropwise to a stirring solution of the ester compound of Example 151 (1.66 g, 4.7 mmol) in THF (25 mL) at room temperature under nitrogen. The mixture was stirred for 3 h before being diluted with ether (100 mL) and quenched by the cautious addition of sodium hydroxide (2 M) (approximately 1 mL). The mixture was stirred for 10 min before being dried (MgSO$_4$), filtered and concentrated in vacuo. Purification of the residue by flash chromatography {SiO$_2$; [(MeOH/ 880 NH$_3$) 9:1] in DCM (2% →4%)] gave the desired alcohol compound (0.7 g, 48%); Example 90: $\delta_H$(CDCl$_3$, 400 MHz) 2.13 (6 H, s), 3.39 (2 H, s), 4.70 (2 H, s), 6.93–6.98 (3 H, m), 7.30 (1 H, d), 7.52–7.56 (3 H, m); MS m/z (TS$^+$) 326 (MH$^+$).

EXAMPLE 155

{3-[([Dimethylamino)methyl]-4-[4-(methylsulfanyl) phenoxy]phenyl}methanol

The reaction of example 154 was repeated using the ester compound of Example 152 to produce the title alcohol.

Free base: $\delta_H$(CDCl$_3$, 400 MHz) 2.06 (6 H, s), 2.43 (3 H, s), 4.30 (2 H, d), 4.47 (2 H, s), 6.80 (1 H, d), 7.03 (2 H, d), 7.31 (2 H, d), 7.34 (1 H, m), 7.60 (1 H, d); MS m/z (ES+) 304 (MH$^+$)

EXAMPLE 156

{3-[(Methylamino)methyl]-4-[4-(methylsulfanyl)phenoxy]phenyl}methanol

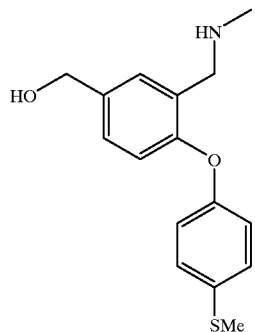

The title alcohol was prepared from the ester of example 153 using the procedure described for example 154; δ$_H$(DMSO-D$_6$, 400 MHz) 2.45 (3 H, s), 2.57 (3 H, s), 4.15 (2 H, s), 4.47 (2 H, s), 5.26 (1 H, br), 6.78 (1 H, d), 7.01 (2 H, d), 7.33 (3 H, m), 7 54 (1 H, s), 8.86 (2 H, br), MS m/z (ES$^+$) 290 (MH$^+$).

EXAMPLE 157

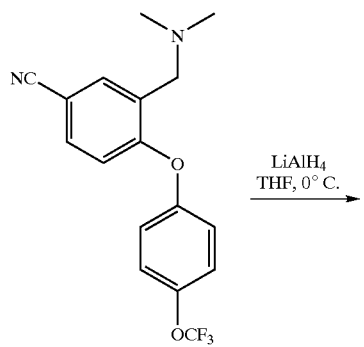

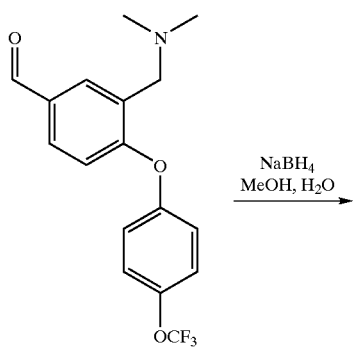

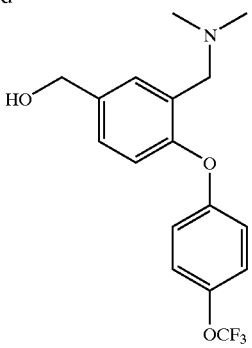

Step 1. Preparation of aldehyde

To a stirred slurry of lithium aluminum hydride (745 mg, 19.6 mmol) in THF (100 mL), at 0° C. under nitrogen, was added dropwise a solution of the compound of Example 84 (2.2 g, 6.54 mmol) in THF (50 mL). The mixture was then stirred at 0° C. for 2 h before warming to room temperature and quenching by the addition of aqueous sodium hydroxide (2M). The resulting mixture was dried (MgSO$_4$), filtered and concentrated in vacuo. The residue was purified by flash chromatography [SiO$_2$; DCM/ MeOH/ 880 NH$_3$ (95:5:1 →93:7:1)] to give the desired aldehyde (730 mg, 33%) as a yellow oil δ$_H$ (CDCl$_3$, 400 MHz) 2.30 (6 H, s), 3.57 (2 H, s), 6.88 (1 H, d), 7.02 (2 H, m), 7.21 (2 H, m), 7.73 (1 H, dd), 8.01 (1 H, d); 9.95 1H, s); MS m/z (TS$^+$) 340 (MH$^+$).

Step 2. Reduction of intermediate aldehyde to the desired alcohol

Sodium borohydride (80 mg, 2.11 mmol) was added to a solution of intermediate aldehyde (720 mg, 2.12 mmol) in MeOH (20 mL) and water (1 mL) and the mixture was stirred at room temperature for 4 h. The reaction was quenched by the addition of hydrochloric acid (2M) and extracted with ethyl acetate. The organic extract was dried (MgSO$_4$) and concentrated in vacuo. The residue was purified by flash chromatography [SiO$_2$; DCM/ MeOH/ 880 NH$_3$ (95:5:1 →93:7:1)] to give the desired alcohol compound as an oil (140 mg, 19%); δ$_H$ (CDCl$_3$, 400 MHz) 2.08 (1 H, br), 2.29 (6 H, s), 3.49 (2 H, s), 4.70 (2 H, s), 6.91 (3 H, m), 7.16 (2 H, m), 7.27 (1 H, m), 7.52 (1H, s); m/z 342 (MH$^+$).

EXAMPLE 158

3-[(Dimethylamino)methyl]-4-[4-(methylsulfanyl)phenoxy]benzoic acid

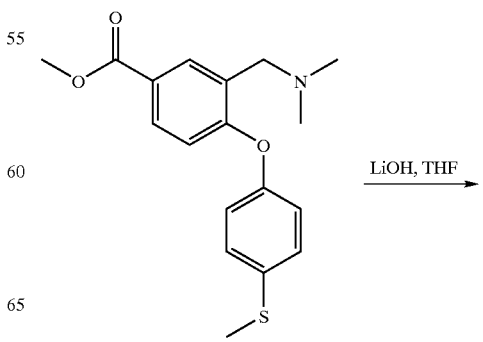

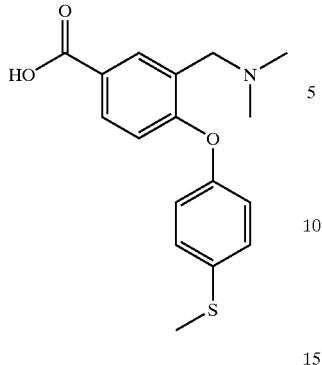

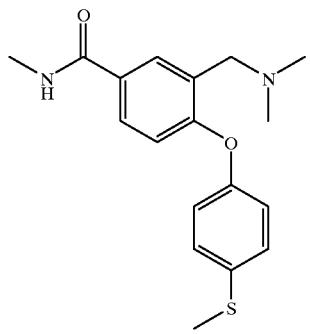

The ester from example 152 (5.22 g, 15.8 mmol) was dissolved in THF (60 mL), treated with aqueous lithium hydroxide (1 M, 63.1 mmol) and heated at reflux overnight. The reaction was neutralised with hydrochloric acid (2 M) and extracted with DCM. The organic extracts were dried (MgSO$_4$) and evaporated to a white foam of the title carboxylic acid (4.80 g, 95%); $\delta_H$ (CD$_3$OD, 400 MHz) 2.48 (3 H, s), 2.56 (6 H, s), 3.94 (2 H, s), 6.80 (1 H, d), 7.00 (2 H, d), 7.33 (2 H, d), 7.94 (1 H, d), 8.09 (1 H, s); MS m/z (ES$^+$) 318 (MH$^+$).

EXAMPLE 159

3-[(Dimethylamino)methyl]-N-methyl-4-[4-(methylsulfanyl)phenoxy]benzamide

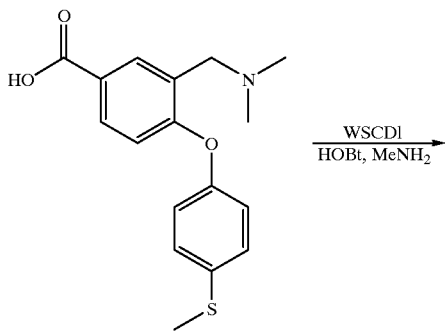

The product from example 158 (480 mg, 1.51 mmol) WSCDI (377 mg, 2 mmol), HOBt.H$_2$) (255 mg, 1.66 mmol) and triethylamine (0.53 mL, 3.78 mmol) were dissolved in DCM (0.03 M). After stirring for 30 min, MeNH$_2$ (condensed, 2 mL) was added and the mixture stirred for a further 12 h. The mixture was then evaporated and the residue partitioned between ethyl acetate and water. The organic layer was separated and the aqueous layer re-extracted with ethyl acetate (3 times). The combined organic layers were dried (MgSO$_4$) and evaporated to a yellow oil, which was purified by flash chromatography [SiO$_2$; DCM/ MeOH/ 880 NH$_3$ (93:7:1)]. The desired title amide was isolated as its hydrochloride salt (285 mg, 63%); Free base: $\delta_H$(CDCl$_3$, 400 MHz) 2.12 (6 H, s), 2.41 (3 H, s), 2.92 (3 H, d), 3.46 (3 H, s), 6.78 (1 H, brd), 6.84 (2 H, d), 7.20 (2 H, d), 7.63 (1 H, dd), 7.82 (1 H, d); MS m/z (ES+) 331 (MH$^+$)

EXAMPLES 160–168

The following amides were prepared in an analogous fashion to that in Example 159 from the the carboxylic acid of Example 158 and the appropriate amine.

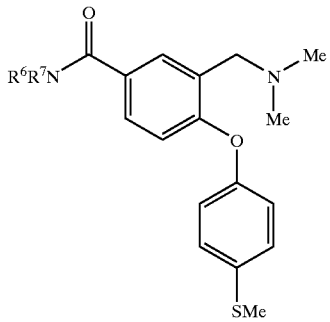

| Example | —NR$^6$R$^7$ | Data |
|---|---|---|
| 160 | 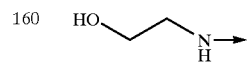 | Free base: $\delta_H$(CDCl$_3$, 400MHz)2.27(6H, s), 2.49(3H, s), 3.50(2H, s), 3.59(2H, m), 3.81(2H, t), 6.82(1H, d), 6.90(2H, d), 7.08(1H, t), 7.25(2H, d), 7.67(1H, d), 7.90(1H, s); MSm/z(ES$^+$)361(MH$^+$) |

-continued

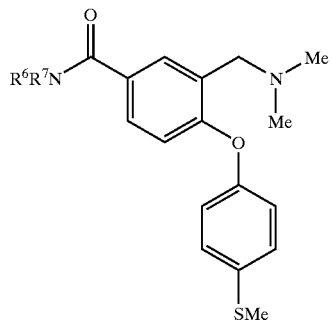

| Example | —NR⁶R⁷ | Data |
|---|---|---|
| 161 | 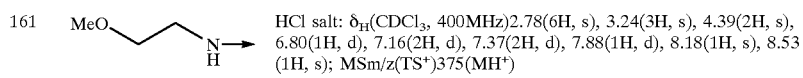 | HCl salt: δ_H(CDCl₃, 400MHz)2.78(6H, s), 3.24(3H, s), 4.39(2H, s), 6.80(1H, d), 7.16(2H, d), 7.37(2H, d), 7.88(1H, d), 8.18(1H, s), 8.53 (1H, s); MSm/z(TS⁺)375(MH⁺) |
| 162 | 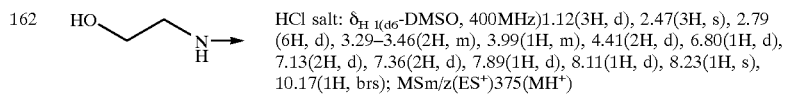 | HCl salt: δ_H(d₆-DMSO, 400MHz)1.12(3H, d), 2.47(3H, s), 2.79 (6H, d), 3.29–3.46(2H, m), 3.99(1H, m), 4.41(2H, d), 6.80(1H, d), 7.13(2H, d), 7.36(2H, d), 7.89(1H, d), 8.11(1H, d), 8.23(1H, s), 10.17(1H, brs); MSm/z(ES⁺)375(MH⁺) |
| 163 | 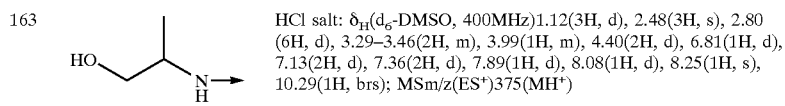 | HCl salt: δ_H(d₆-DMSO, 400MHz)1.12(3H, d), 2.48(3H, s), 2.80 (6H, d), 3.29–3.46(2H, m), 3.99(1H, m), 4.40(2H, d), 6.81(1H, d), 7.13(2H, d), 7.36(2H, d), 7.89(1H, d), 8.08(1H, d), 8.25(1H, s), 10.29(1H, brs); MSm/z(ES⁺)375(MH⁺) |
| 164 | 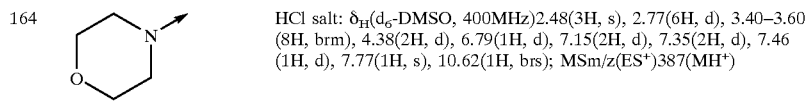 | HCl salt: δ_H(d₆-DMSO, 400MHz)2.48(3H, s), 2.77(6H, d), 3.40–3.60 (8H, brm), 4.38(2H, d), 6.79(1H, d), 7.15(2H, d), 7.35(2H, d), 7.46 (1H, d), 7.77(1H, s), 10.62(1H, brs); MSm/z(ES⁺)387(MH⁺) |
| 165 | 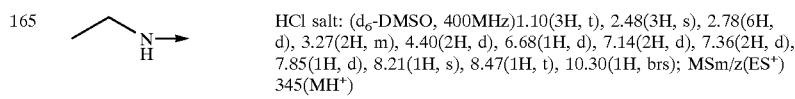 | HCl salt: (d₆-DMSO, 400MHz)1.10(3H, t), 2.48(3H, s), 2.78(6H, d), 3.27(2H, m), 4.40(2H, d), 6.68(1H, d), 7.14(2H, d), 7.36(2H, d), 7.85(1H, d), 8.21(1H, s), 8.47(1H, t), 10.30(1H, brs); MSm/z(ES⁺) 345(MH⁺) |
| 166 | 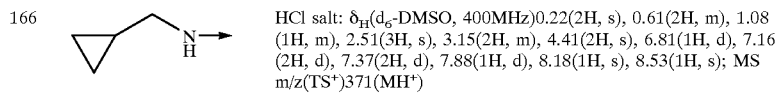 | HCl salt: δ_H(d₆-DMSO, 400MHz)0.22(2H, s), 0.61(2H, m), 1.08 (1H, m), 2.51(3H, s), 3.15(2H, m), 4.41(2H, s), 6.81(1H, d), 7.16 (2H, d), 7.37(2H, d), 7.88(1H, d), 8.18(1H, s), 8.53(1H, s); MS m/z(TS⁺)371(MH⁺) |
| 167 | 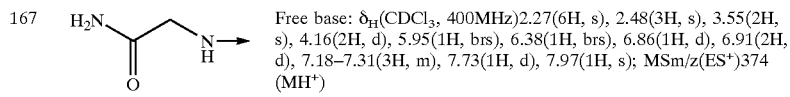 | Free base: δ_H(CDCl₃, 400MHz)2.27(6H, s), 2.48(3H, s), 3.55(2H, s), 4.16(2H, d), 5.95(1H, brs), 6.38(1H, brs), 6.86(1H, d), 6.91(2H, d), 7.18–7.31(3H, m), 7.73(1H, d), 7.97(1H, s); MSm/z(ES⁺)374 (MH⁺) |
| 168 | 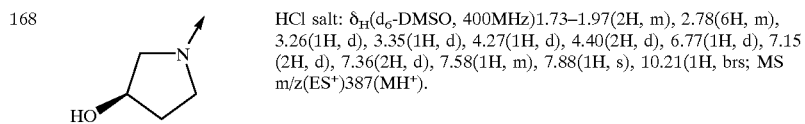 | HCl salt: δ_H(d₆-DMSO, 400MHz)1.73–1.97(2H, m), 2.78(6H, m), 3.26(1H, d), 3.35(1H, d), 4.27(1H, d), 4.40(2H, d), 6.77(1H, d), 7.15 (2H, d), 7.36(2H, d), 7.58(1H, m), 7.88(1H, s), 10.21(1H, brs; MS m/z(ES⁺)387(MH⁺). |

EXAMPLE 169
4-[3-Methoxy-4-(methylsulfanyl)phenoxy]-3-[(methylamino)methyl]benzamide

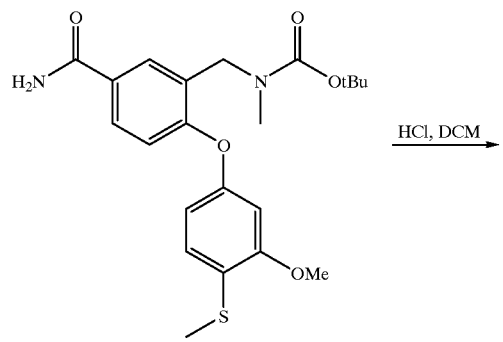

The Boc-protected amine of preparation 53 (280 mg, 0.65 mmol) was dissolved in DCM (10 mL) and the solution cooled to 0° C. Hydrogen chloride gas was bubbled through the solution for 15 minutes and then the solution was evaporated to dryness. The residue was co-evaporated several times using DCM/ethyl acetate (1:1) and then diethyl ether. The product was obtained as a white solid which was dried under vacuum (240 mg, ca.100%); HCI salt: $\delta_H$(CD$_3$OD, 400 MHz) 2.37 (3 H, s), 2.77 (3 H, s), 3.82 (3 H, s), 4.35 (2 H, s), 6 73 (1 H, dd), 6.80 (1 H, d), 6.84 (1 H, d), 7.36 (1 H, d), 7.86 (1 H, dd), 8.03 (1 H, d); MS m/z (TS$^+$) 333 (MH$^+$).

EXAMPLES 170–176

A series of amides was prepared in an analogous fashion to that in example 169 from the requisite Boc-protected amines.

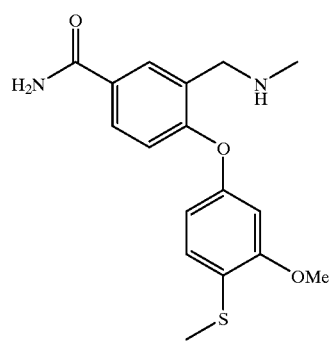

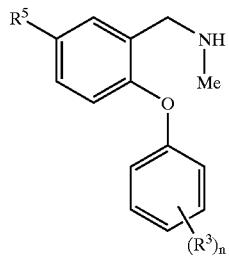

| Example | Starting material | R$^5$ | (R$^3$)$_n$ | data |
|---|---|---|---|---|
| 170 | Prep 47 | MeO\~\~NH-C(O)- | 4-SMe | HCl salt: $\delta_H$(CDCl$_3$, 300 MHz)2.47(3H, s), 2.49(3H, s), 3.39(3H, s), 3.58(2H, t), 3.66(3H, t), 3.84(2H, s), 6.48(1H, brs), 6.83(1H, d), 6.93(2H, d), 7.29(2H, d), 7.64(1H, d), 7.81(1H, s); MSm/z(TS$^+$) 361(MH$^+$) |
| 171 | Prep 48 | HO\~\~NH-C(O)- | 4-SMe | HCl salt: $\delta_H$(CDCl$_3$, 300 MHz)2.46(3H, s), 2.47(3H, s), 3.60(2H, in), 3.80(2H, m), 3.85(2H, s), 6.80–6.87(2H, m), 6.94 (2H, d), 7.30(2H, s), 7.67(1H, d), 7.85 (1 H, s); MSm/z(TS$^+$)347(MH$^+$) |
| 172 | Prep 49 | H$_2$N-C(O)-CH$_2$-NH-C(O)- | 4-SMe | Free base: $\delta_H$(CDCl$_3$, 300 MHz)2.49 (3H, s), 2.50(3H, s), 3.88(2H, s), 4.17 (2H, d), 6.82(1H, d), 6.93–7.00(3H, m), 7.29(2H, d), 7.70(1H, d), 7.91(1H, s); MSm/z(TS$^+$)360(MH$^+$) |

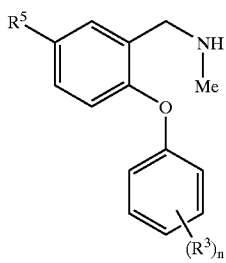

| Example | Starting material | R⁵ | (R³)ₙ | data |
|---|---|---|---|---|
| 173 | Prep 50 | HO−CH(CH₃)−NH−C(O)− | 4-SMe | Free base: δ_H(CDCl₃, 400 MHz)1.18 (3H, d), 2.45(3H, s), 2.46(3H, s), 3.62 (1H, dd), 3.75(1H, dd), 3.91(2H, s), 4.20– 4.28 (1H, m), 6.23(1H, brd), 6.79(1H, d), 6.89(2H, d), 7.23(2H, d), 7.61(1H, d), 7.79(1H, s); MSm/z(TS⁺)361(MH⁺) |
| 174 | Prep 51 | HO−CH(CH₃)−NH−C(O)− | 4-SMe | Free base: δ_H(CDCl₃, 400 MHz)1.23 (3H, d), 2.44(6H, s), 2.46(3H, s), 3.62 (1H, dd), 3.76(1H, dd), 3.91(2H, s), 4.20– 4.28 (1H, m), 6.34(1H, brd), 6.79(1H, d), 6.88(2H, d), 7.25(2H, d), 7.62(1H, d), 7.81(1H, s); MSm/z(TS⁺)361(MH⁺) |
| 175 | Prep 52 | MeNH−C(O)− | 4-SMe | HCl salt: δ_H(CD₃OD, 400 MHz)2.49(3H, s), 2.80(3H, s), 2.91(3H, s), 4.37(2H, s), 6.83(1H, d), 7.12(2H, d), 7.38(2H, d), 7.81(1H, d), 8.00(1H, s); MSm/z(TS⁺) 318(MH⁺) |
| 176 | Prep 54 | MeNH−C(O)− | 3-OMe, 4-SMe | HCl salt: δ_H(CD₃OD, 400 MHz)2.38(3H, s), 2.77(3H, s), 2.91(3H, s), 3.81(3H, s), 4.35(2H, s), 6.72(1H, dd), 6.79(1H, d), 6.85(1H, d), 7.23(1H, d), 7.78(1H, dd), 7.96(1H, d); MSm/z(TS⁺)347(MH⁺) |

EXAMPLE 177

3-[(Methylamino)methyl]-4-[4-(methylsulfanyl)-3-(trifluoromethyl)phenoxy]-benzamide

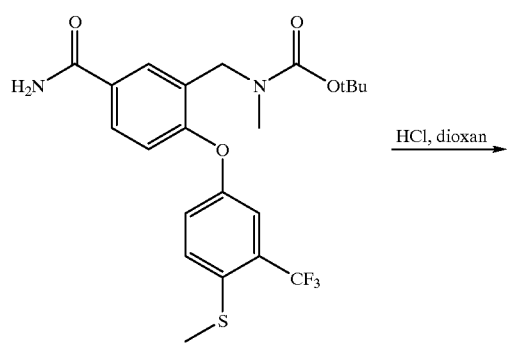

The Boc-protected amine of preparation 46 (396 mg, 0.842 mmol) was treated with hydrochloric acid (4 M) in dioxan (5 mL) and stirred for 1.5 hours. The solvent was removed by evaporation and the residue basified by the addition of saturated aqueous sodium bicarbonate solution and then extracted with DCM (4×10 mL). The combined organic extracts were washed with brine (10 mL) dried (MgSO$_4$) and evaporated to a yellow oil. This oil was purified by flash chromatography [SiO$_2$; DCM/ MeOH/ 880 NH$_3$(93:7:1)] to afford the title amide as a white foam (208 mg, 66%). Free base: δ$_H$(CDCl$_3$, 400 MHz) 2.45 (3 H, s), 2.51 (3 H, s), 3.82 (2 H, s), 6.84 (1 H, d), 7.10 (1 H, d), 7.31 (1 H, s), 7.40 (1 H, d), 7 72 (1 H, dd), 7.91 (1 H, s); MS m/z (TS$^+$) 371 (MH$^+$).

EXAMPLE 178

3-[(Dimethylamino)methyl]-4-[4-(methylsulfanyl)-3-(trifluoromethyl)-phenoxy]benzamide

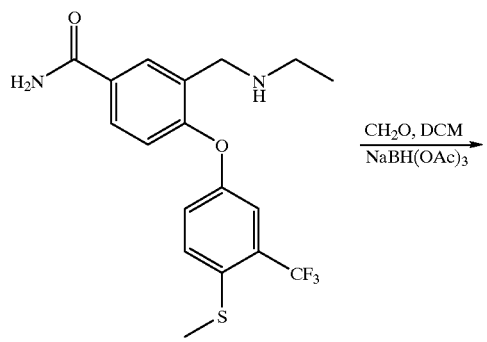

-continued

The amide from example 177 (105 mg, 0.28 mmol) was suspended in DCM (3 mL) and treated with formaldehyde (37% aqueous, 35 μL, 0.425 mmol). The mixture was stirred for 30 minutes (dissolution had occurred by this stage) and then treated with sodium tri(acetoxy)borohydride (120 mg, 0.567 mmol). The reaction was stirred overnight and then diluted with water (5 mL), basified with 880 ammonia (1 mL) and extracted with DCM (3×10 mL). The combined organic extracts were washed with brine (5 mL), dried (MgSO$_4$) and evaporated to a white solid. Purification by flash chromatography [SiO$_2$; DCM, MeOH, 880 NH$_3$ (95:5:0.5)] afforded the title amide as a white powder (85 mg, 78%); Free base: δ$_H$ (CDCl$_3$, 400 MHz) 2.24 (6 H, s), 2.46 (3 H, s), 3.50 (2 H, s), 5.47–6.15 (2 H, brm), 6.85 (1 H, d), 7.03 (1 H, d), 7.23 (1 H, s), 7.35 (1 H, d), 7.71 (1 H, d), 7.90 (1 H, s); MS m/z (TS$^+$) 385 (MH$^+$)

EXAMPLES 179–180

The following amides were prepared in an analogous fashion to that in example 178 from the requisite secondary amine.

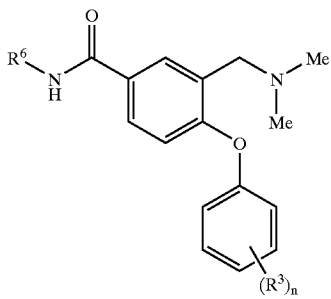

| Example | Starting Material | R$^6$ | (R$^3$)$_n$ | data |
|---|---|---|---|---|
| 179 | Example 169 | H | 3-OMe, 4-SMe | δ$_H$(CD$_3$OD, 400MHz)2.41(3H, s), 2.97(6H, s), 3.86(3H, s), 4.54(2H, s), 6.77(1H, dd), 6.85 (1H, d), 6.91(1H, d), 7.28(1H, d), 7.93(1H, dd), 8.10(1H, d); MSm/z(TS$^+$)347(MH$^+$) |
| 180 | Example 176 | Me | 3-OMe, 4-SMe | δ$_H$(CDCl$_3$, 400MHz)2.44(3H, s), 2.87(6H, s), 3.00(3H, d), 3.85(3H, s), 4.35(2H, s), 6.56(2H, m), 6.88(1H, d), 7.16(1H, d), 7.58(1H, brd), 7.94(1H, dd), 8.61(1H,d); MSm/z(TS$^+$)361 (MH$^+$) |

EXAMPLES 181 and 182

N-Methyl-N-[2-[4-(methylsulfanyl)phenoxy]-5-(1 H-1,2,3-triazol- 1-yl)benzyl]amine (Example 181) and N-methyl-N-[2-[4-(methylsulfanyl)phenoxy]-5-(2 H-1,2,3-triazol-2-yl)benzyl]amine (Example 182)

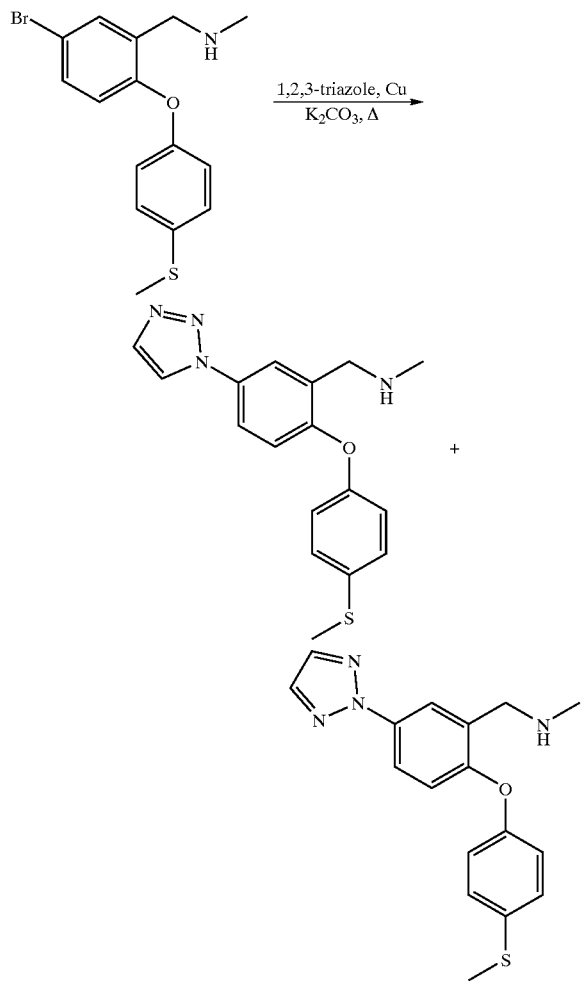

Example 181 (mono-hydrochloride salt) (270 mg, 13%); $\delta_H$(d$_6$-DMSO, 400 MHz) 2.50 [3 H, s(obsc.)], 2.64 (3 H, t), 4.27 (2 H, t), 6.97 (1 H, d), 7.14 (2 H, d), 7.36 (2 H, d), 7.87 (1 H, dd), 7.99 (1 H, s), 8.26 (1 H, d), 8.76 (1 H, s), 9.16 (2 H, brs); MS m/z (TS$^+$) 327 (MH$^+$).

Example 182 (bis-hydrochloride salt) (400 mg, 17%); $\delta_H$(CDCl$_3$, 400 MHz) 2.50 (3 H, s), 2.67 (3 H, brs), 4.18 (2 H, brs), 6.95 (1 H, d), 7.15 (2 H, d), 7.27 (2 H, d), 7.74 (2 H, s), 7.96 (1 H, dd), 8.35 (1 H, d), 9.92 (2 H, brs); MS m/z (TS$^+$) 327 (MH$^+$).

EXAMPLE 183

N,N-Dimethyl-N-[2-[4-(methylsulfanyl)phenoxy]-5-(2 H-1,2,3-triazol-2-yl)benzyl]amine

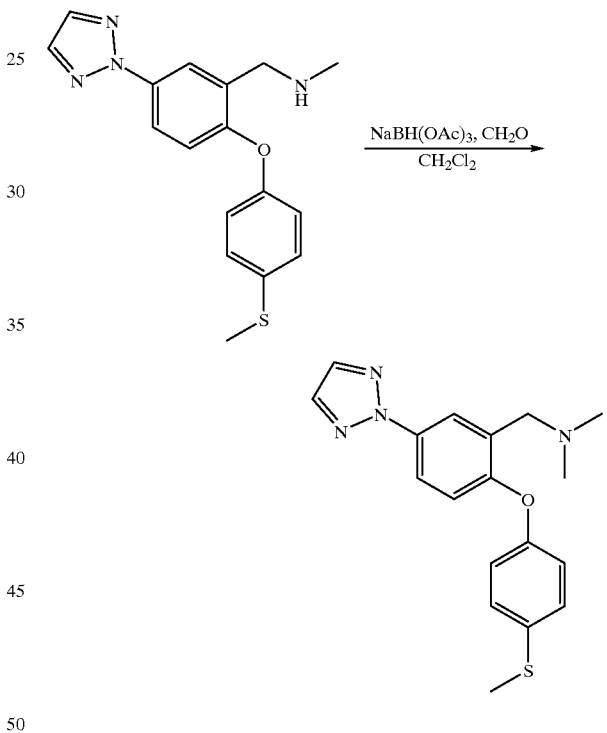

The bromide of Example 23 (2.0 g, 6 mmol) was mixed with copper powder (378 mg, 6 mmol) 1,2,3-triazole (ca. 5 g, excess), and potassium carbonate (828 mg, 6 mmol) were heated together at 160° C. for 48 h. After cooling to room temperature the reaction mixture was partitioned between sodium hydroxide (3 M) and ethyl acetate. The organic layer was separated and washed with sodium hydroxide (3 M) (3 x), water, and brine, before being dried (MgSO$_4$) and evaporated. The resulting residue was purified by flash chromatography [SiO$_2$; DCM/ MeOH/ 880 NH$_3$ (97.5:2.5:0.25)] to afford, separately, the 1-substitiuted triazole derivative compound of Example 181 and the 2-substituted isomer compound of Example 182. The hydrochloride salt of each was precipitated by treatment with ethereal hydrochloric acid (1 M solution, excess).

The triazole derivative hydrochloride salt of Example 182 (400 mg, 1.1 mmol) was suspended in DCM (30 mL) and formaldehyde (37% aqueous) (ca. 0.2 mL, ca. 5.5 mmol) was added followed by sodium tris(acetoxy)borohydride (1.16 g, 5.5 mmol). The reaction mixture was stirred at room temperature for 1 h and then partitioned between sodium hydroxide (3 M) and DCM. The organic layer was separated and the aqueous layer extracted further with DCM (4 x). The combined organic fractions were washed with brine, dried (MgSO$_4$), and evaporated to give the title compound as a colourless oil (290 mg, 70%); $\delta_H$(CDCl$_3$, 400 MHz), 2.44 (3 H,s), 2.49 (6 H, s), 3.75 (2 H, brs), 6.93 (2 H, d), 6.98 (1 H, d), 7.26 (2 H, d), 7.80 (2 H, s), 7.85 (1 H, dd), 8.26 (1 H, d); MS m/z (TS$^+$) 341 (MH$^+$).

EXAMPLE 184

N,N-Dimethyl-N-[2-[4-(methylsulfanyl)phenoxy]-5-(1 H-1,2,3-triazol-1-yl)benzyl]-amine

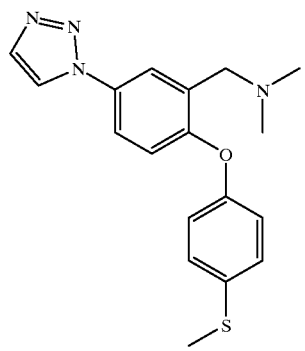

The title compound was prepared from the product of example 181 in an analogous fashion to that used for the preparation of the compound of Example 183 (108 mg, 52%); $\delta_H$ (CDCl$_3$, 400 MHz) 2.18 (6 H, s), 2.44 (3 H, s), 3.48 (2 H, brs), 6.97 (2 H, d), 7 06 (1 H, d), 7.29 (2 H, d), 7.76 (1 H, d), 7.97 (2 H, d), 8.80 (1 H, s), MS m/z (TS$^+$) 341 (MH$^+$).

EXAMPLE 185

N-[2-[4-(Methylsulfanyl)phenoxy]-5-(1 H-imidazol-1-yl)benzyl]-N-methylamine

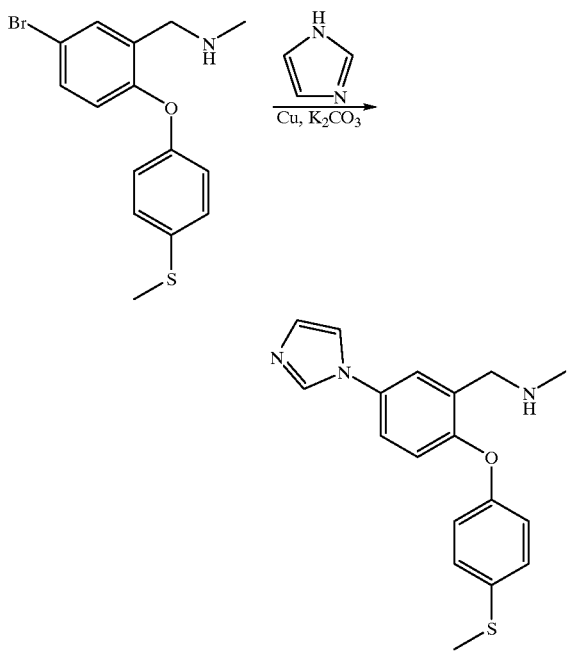

The aryl bromid e d erivative from Example 23 (2 g, 6 mmol) was combined with imidazole (5 g, 73.5 mmol), copper powder (381 mg, 6 mmol) and potassium carbonate (828 mg, 6 mmol) and the mixture heated at 160° C. for 3 hours. After cooling to room temperature the mixture was partitioned between aqueous sodium hydroxide (3 M) and ethyl acetate. The organic layer was separated, washed with aqueous sodium hydroxide (3 M) (3 times), water (3 times), brine and then dried (MgSO$_4$) and evaporated. The residue was purified by flash chromatography [SiO$_2$; DCM/ MeOH/ 880 NH$_3$ (95:5:0.5)] to provide the title compound which was isolated as its bis HCl salt by the standard method (57 mg, 2%); bis HCl salt: $\delta_H$(d$_6$-DMSO, 400 MHz) 2.49 (3 H, s), 2.61 (3 H, s), 4.26 (2 H, s), 6.96 (1 H, d), 7.14 (2 H, d), 7.36 (1 H, dd), 7.84 (1 H, s), 8.21 (1 H, s), 8.28 (1 H, s), 9.56 (3 H, brs); MS mz (TS$^+$) 326 (MH$^+$)

EXAMPLE 186

N-[2-[4-(Methylsulfanyl)phenoxy]-5-(1 H-imidazol-1-yl)benzyl]-N,N-dimethylamine

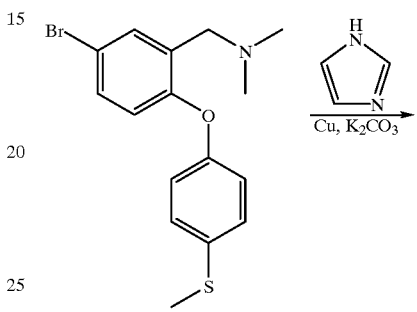

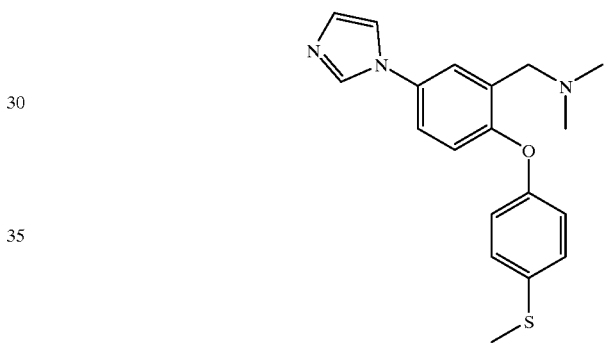

The title compound was prepared from the aryl bromide of example 9 using the procedure described for Example 185; bis HCl salt: $\delta_H$(CD$_3$OD, 400 MHz) 2.51 (3 H, s), 3.00 (6 H, s), 4.60 (2 H, s), 7.06 (1 H, d), 7.17 (2 H, d), 7.41 (2 H, d), 7.77 (3 H, m), 8.11 (2 H, d), 9.47 (1 H, s); MS m/z (TS$^+$) 340 (MH$^+$)

EXAMPLE 187

N-Methyl-N-[2-[4-(methylsulfanyl)phenoxy]-5-(1 H-1,2,4-triazol-1 -yl)benzyl]amine

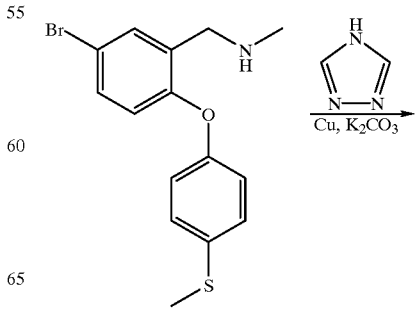

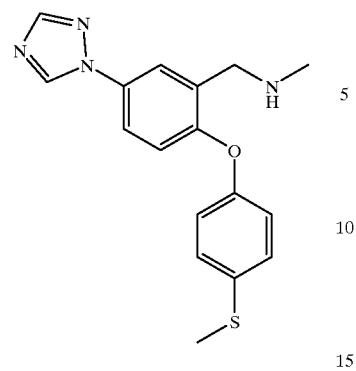

The title compound was prepared from the aryl bromide of example 23 using the procedure described for Examples 181/ 182, bis HCl salt: $\delta_H$(d$_6$-DMSO, 400 MHz) 2.50 (3 H, s), 2.62 (3 H, s), 4.27 (2 H, s), 6.95 (1 H, d), 7.14 (2 H, d), 7.36 (2 H, d), 7.85 (1 H, d), 8.21 (1 H, s), 8.27 (1 H, s), 9.26 (3 H, brs); MS m/z (TS$^+$) 327 (MH$^+$)

EXAMPLE 188

N,N-dimethyl-N-[2-[4-(methylsulfanyl)phenoxy]-5-(1 H-1,2,4-triazol-1 -yl)benzyl]-amine

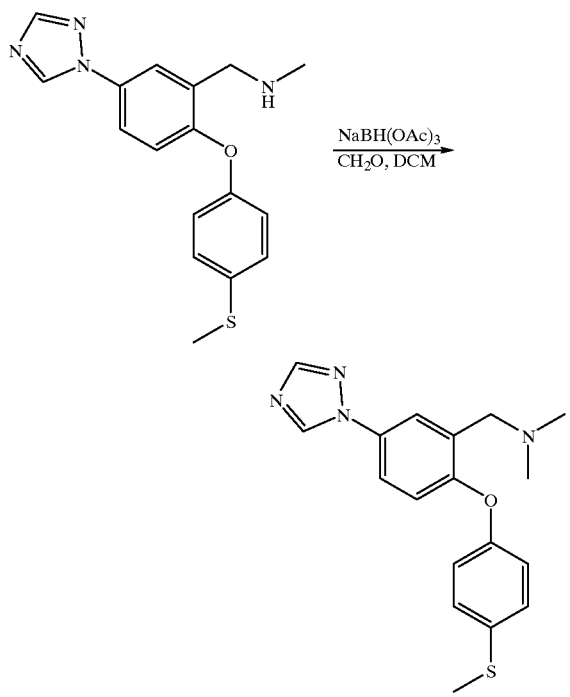

The title compound was prepared from the secondary amine of example 187 using the reductive methylation procedure described for Example 183; Free base: $\delta_H$(CDC$_3$, 400 MHz) 2.30 (6 H, s), 2.48 (3 H, s), 3.54 (2 H, s), 6.91 (2 H, d), 6.97 (1 H, d), 7.27 (2 H, d), 7.52 (1 H, dd), 7.82 (1H, d), 8.10 (1 H, s), 8.54 (1 H, s); MS m/z (TS$^+$) 341 (MH$^+$)

EXAMPLE 189

N-[2-[4-(Methylsulfanyl)phenoxy]-5-(4H- 1,2,4-triazol-4-yl)benzyl]-N,N-dimethylamine

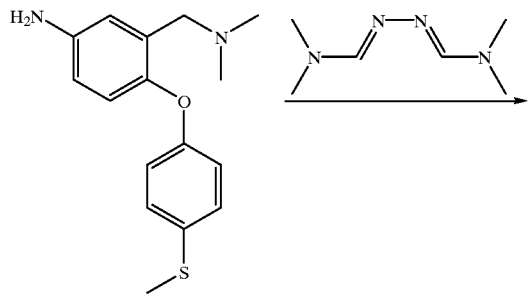

Th aniline of example 109 (500 mg, 1.7 mol), N'-[(dimethylamino)methylidene]-N,N-dimethylhydrazonoformamide (590 mg, 4.15 mmol) [prepared according to Bartlett et al. *J. Chem. Soc.* (C), 1967, 1664], and p-toluenesulfonic acid (394 mg, 2 mmol) were mixed in toluene (10 mL) and heated at reflux for 2 days. The mixture was cooled to room temperature and treated with saturated aqueous sodium bicarbonate solution and diluted with ethyl acetate. The organic layer was separated, washed with brine, dried (MgSO$_4$) and evaporated. The residue was purified by flash chromatography [SiO$_2$; DCM/ MeOH/ 880 NH$_3$ (90:10:1)] to afford the desired triazole derivative (100 mg, 17%); $\delta_H$(CDCl$_3$, 400 MHz) 2.29 (6 H, s), 2.48 (3 H, s), 3.54 (2 H, s), 6.92 (2 H, d), 6.95 (1 H, d), 7.19 (IH, dd), 7.29 (2 H, d), 7.46 (2 H, s); MS m/z (TS$^+$) 341 (MH$^+$)

EXAMPLE 190

N-{5-(3-Amino-1H-pyrazol-1-yl)-2-[4-(methylsulfanyl)phenoxy]benzyl}-N-methylamine

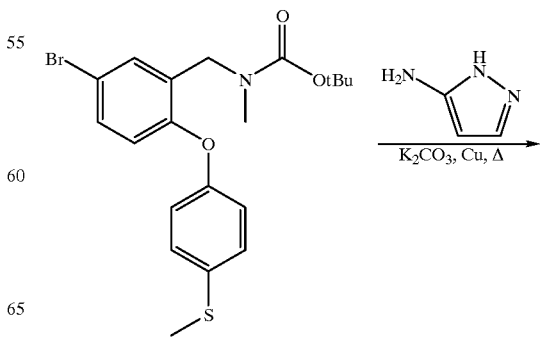

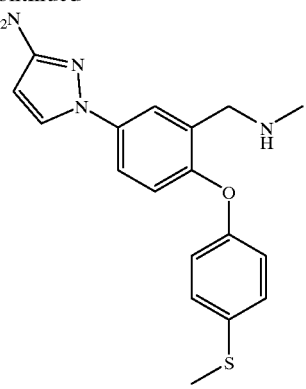

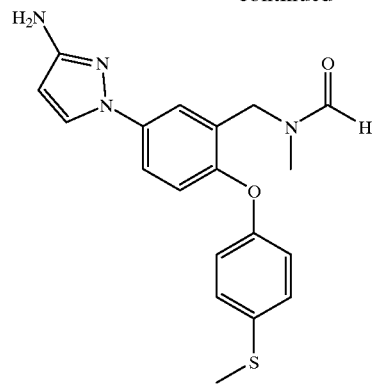

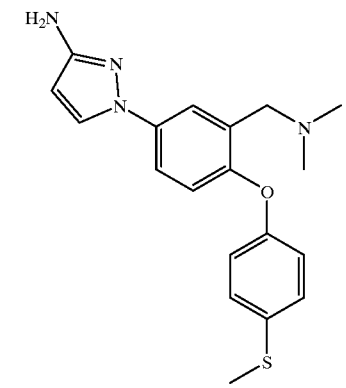

Copper powder (1.53 g, 24 mmol), potassium carbonate (6.08 g, mmol) and 3-aminopyrazole were mixed and heated to 50° C. to form a melt. Iodine (51 mg, 0.2 mmol) was added and the mixture stirred for 20 minutes before the addition of the aryl bromide from preparation 39 (8.77 g, 20 mmol). After a further 10 minutes the reaction mixture was heated to 140° C. for 9 hours, After cooling to room temperature the mixture was partitioned between saturated aqueous ethylenediaminetetraacetic acid (EDTA) and ethyl acetate (70 mL each) and the mixture stirred for 4 hours. The mixture was further diluted with satuated aqueous EDTA and ethyl acetate (1000 mL each). The ethyl acetate layer was separated, washed with brine, dried and evaporated. The residue was purified by flash chromatography {SiO$_2$; [MeOH 880 NH$_3$ (1:9)] in DCM (1→10%) to provide the title compound as a brown oil which solidified on standing under vacuum (1.52 g, 22 %); $\delta_H$(CDCI$_3$, 400 MHz) 2.44 (3 H, s), 2.52 (3 H, s), 3.77 (4 H, brs), 5.80 (1 H, s), 6.86 (3 H, m), 7.25 (2 H, d), 7.39 (1 H, dd), 7.58 (1 H, d), 7.63 (1 H, s).

EXAMPLE 191

N-{5-(3-Amino- 1 H-pyrazol- 1 -yl)-2-[4-(methylsulfanyl)phenoxy]benzyl}-N, N-dimethylamine

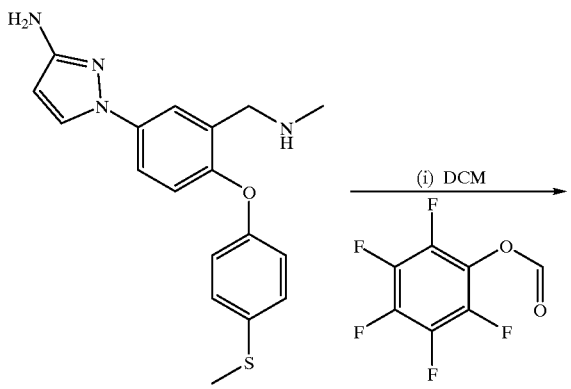

(i) Preparation of the Formamide

Formic acid (145 μL, 3.84 mmol) was added to a solution of pentafluorophenoi (642 mg, 3.49 mmol) in ether (5 mL) at 0° C. followed by dicyclohexylcarbodiimide (722 mg, 3.49 mmol). The mixture was stirred at 0° C. for 15 min and at room temperature for 1 h before being filtered, the residue being washed with ether. The ethereal solution of pentafluorophenyl formate was evaporated to dryness, redissolved in DCM (8 mL) added to a solution of the aminopyrazole from example 190 (1.08 g, 3.17 mmol) in DCM (8 mL) and the reaction mixture stirred at room temperature for 1.5 hours. The reaction mixture was then diluted with DCM and aqueous potassium carbonate (10%; 50 mL each). The organic layer was separated and dried (MgSO$_4$) before being evaporated to dryness. The residue was purified by flash chromatography {SiO$_2$; [MeOH/ 880 NH$_3$ (9:1)] in DCM (1→1.5 %)} to provide the intermediate formamide (770 mg, 66%); $\delta_H$(CDCI$_3$, 400 MHz, 2 rotomers visible) 2.47 (3 H, s), 2.80 (3 H, s), 2.88 [3 H, s (minor rotomer)], 4.41 (2 H, s), 4.56 [2 H, s (minor rotomer)], 5.79 [1 H, d (minor rotomer)], 5.81 (1 H, d), 6.83–6.92 (4 H, m), 7.36–7.46 (1 H, m), 7.46 (1 H, s), 7.59 (1 H, d), 8.11 [1 H, s (minor rotomer)], 8.22 (1 H, s); MS m/z (TS+) 369 (MH+).

(ii) Reduction to the Tertiary Amine

The formamide from stage (i) (770 mg, 2.09 mmol) was dissolved in THF (21 mL) and treated with borane-tetrahydrofuran complex (1 M in THF, 6.27 mL, 6.27 mmol) at room temperature. The reaction mixture was heated at reflux for 2 hours before being cooled to room temperature and quenched by the cautious addition of hydrochloric acid (6 M; 15 mL). The mixture was then reheated to 80° C. for 30 minutes before being recooled to room temperature. The mixture was made basic by the addition of sodiumhydroxide (2 M; 50 mL) and then extracted with DCM (70 mL). the organic layer was separated, dried (MgSO$_4$) and evaporated.

The residue was purified by flash chromatography {SiO$_2$; [MeOH/ 880 NH$_3$ (9:1)] in DCM (1→5 %)} to provide the title compound as a solid (100 mg, yield 13%); $\delta_H$(CDCl$_3$, 400 MHz) 2.22 (6 H, s), 2.42 (3 H, s), 2.42 (2 H, s), 3.76 (2 H, brs), 5.80 (1 H, d), 6.82 (2 H, d), 6.91 (1 H, d), 7.21 (2 H, d), 7.41 (1 H, dd), 7.63 (1 H, d); MS m/z (TS$^+$) 355 (MH$^+$).

EXAMPLE 192

5-Chloro-2-[4-(methylsulfanyl)phenoxy]benzylamine

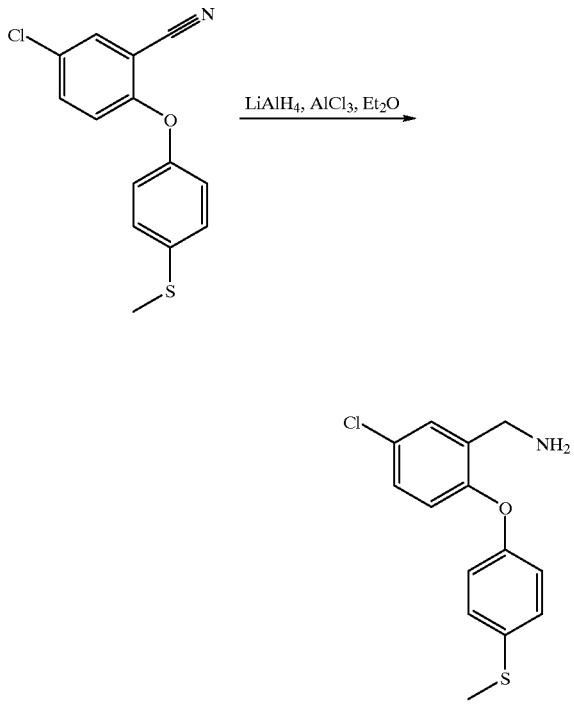

To a suspension of lithium aluminium hydride (745 mg, 19.6 mmol) in diethyl ether (30 mL) was added aluminium chloride (872 mg, 6.54 mmol) in diethyl ether (10 mL). Following complete addition the mixture was stirred for 15 minutes at room temperature, then the nitrile from preparation 58 (2.44 g, 8.7 mmol) in diethyl ether (10 mL) was added dropwise. The mixture was then stirred for 2 hours at room temperature, after which time it was quenched by the addition of sodium hydroxide (1 M; 5 mL) and then diluted with diethyl ether (20 mL). After stirring for 5 minutes the liquid phase was decanted off and the residue washed twice more with diethyl ether (2×20 mL). The combined organic layers were washed with saturated aqueous sodium bicarbonate (20 mL), brine (20 mL), dried (MgSO$_4$) and evaporated to a yellow oil (2.35 g, 96%); $\delta_H$(CDCl$_3$, 400 MHz) 2.47 (3 H, s), 3.84 (2 H, s), 6.75–6.79 (2 H, m), 6.87–6.90 (2 H, m), 7.15–7.29 (2 H, m), 7.38–7.41 (1 H, m); MS m/z (TS$^+$) 280, 282 (MH$^+$).

PREPARATIONS

PREPARATION 1

2-[4-(Methylsulfanyl)phenoxy]benzaldehyde

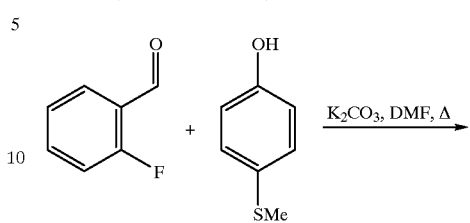

2-Fluorobenzaldehyde (31.6 mL, 300 mmol) and 4-(methylmercapto)phenol (46.27 g, 330 mmol) were dissolved in DMF (500 mL) and potassium carbonate (62.2 g, 450 mmol) was then added. The mixture was heated at 100° C. for 12 h under a nitrogen atmosphere. After cooling to room temperature the mixture was evaporated to dryness, co-evaporated with toluene and then partitioned between ethyl acetate and water. The organic layer was separated, washed with water, dried (MgSO$_4$) and evaporated to a brown oil of the desired aldehyde material (84.4 g) which was contaminated with ca 15% of starting phenol, but sufficiently pure to use directly in the next stage; $\delta_H$(CDCl$_3$, 400 MHz) 2.47 (3 H, s), 6.87 (1 H, d), 6.99 (2 H, m), 7.17 (1 H, m), 7.29 (2 H, m), 7.49 (1 H, m), 7.92 (1 H, d), 10.49 (1 H, s). If required the crude mixture can be purified by flash chromatography [SiO$_2$; ethyl acetate/ hexanes (2→10%)] to obtain a pure sample of the desired aldehyde compound.

Alternatively the title compound can be prepared as follows:

Potassium carbonate (538.7 g, 3.89 mol) and 4-(methylmercapto)phenol (400 g, 2.85 mol) were added successively to DMF (3 L). 2-Fluorobenzaldehyde (322 g, 2.59 mol) was then added to the slurry and the mixture heated in the range 92 to 100° C. After 19 h the reaction mixture was allowed to cool to room temperature and water (2 L) added. The solution was cooled to below 10° C. and the pH adjusted to 2 with 2.5 M HCl (1.5 L), keeping the temperature below 10° C. Water (2.6 L) was added and the slurry stirred at below 5° C. for 2 h. The slurry was filtered and the cake washed with water (4×1 L). The crude product was dissolved in dichloromethane and the solvent distilled to azeotropically remove the water. Fresh dichloromethane was added as required. The dry dichloromethane solution was then concentrated in vacuo to give the crude product as an oil (634 g, 100%).

PREPARATIONS 2–18

The reaction of preparation 1 was repeated under similar conditions using a range of commercially available phenols and 2-fluorobenzaldehydes to provide the compounds of preparations 2 to 18. Each reaction was monitored carefully by thin layer chromatography and was run until deemed complete. The data for these compounds are given in the table below.

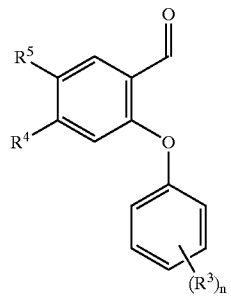

| Preparation | R⁴ | R⁵ | (R³)ₙ | Data |
|---|---|---|---|---|
| 2 | H | Br | 3-CF₃ | $\delta_H$(CDCl₃, 300MHz)6.82(1H, d), 7.23(1H, d), 7.34 (1H, s), 7.48(1H, d), 7.52(1H, dd), 7.65(1H, d), 8.09(1H, s), 10.40(1H, s) |
| 3 | H | Br | 4-CF₃ | $\delta_H$(CDCl₃, 300MHz)6.87(1H, d), 7.16(2H, d), 7.61–7.72(3H, m), 8.08(1H, s), 10.36(1H, s); MS m/z (TS⁺)344,346(MH⁺). |
| 4 | H | H | 4-CF₃ | $\delta_H$(CDCl₃, 300MHz)7.00(1H, d), 7.16(2H, d), 7.28 (3H, m), 7.62(3H, m), 7.98(1H, d), 10.49(1H, s) |
| 5 | Br | H | 4-CF₃ | $\delta_H$(CDCl₃, 300MHz)7.11(1H, s), 7.18(2H, d), 7.42 (1H, d), 7.69(2H, d), 7.84(1H, d), 10.40(1H, s) |
| 6 | H | H | 4-OCF₃ | $\delta_H$(CDCl₃, 300MHz)6.92(1H, d), 7.08(2H, m), 7.23(3H, m), 7.55(1H, m), 7.96(1H, dd), 10.50 (1H, s); MSm/z(TS⁺)300(MNH₄⁺). |
| 7 | H | Br | 4-OCF₃ | $\delta_H$(CDCl₃, 300MHz)6.81(1H, d), 7.08(2H, m), 7.26(2H, m), 7.62(1H, dd), 8.04(1H, d), 10.40(1H, s) |
| 8 | Br | H | 4-OCF₃ | $\delta_H$(CDCl₃, 300MHz)7.05(1H, d), 7.10(2H, d), 7.30(2H, d), 7.35(1H, dd), 7.80(1H, d), 10.45(1H, s) |
| 9 | H | Br | 4-SMe | $\delta_H$(CDCl₃, 300MHz)2.49(3H, s), 6.78(1H, d), 6.98(2H, m), 7.29(2H, m), 7.48(1H, dd), 8.02(1H, d), 10.44(1H, s); MSm/z(TS⁺)340(MNH₄⁺) |
| 10 | H | F | 4-SMe | $\delta_H$(CDCl₃, 300MHz)2.49(3H, s), 6.86–6.99(3H, m), 7.19–7.30(3H, m), 7.58(1H, m), 10.40(1H, d) |
| 11 | H | H | 4-SMe | $\delta_H$(CDCl₃, 400MHz)2.47(3H, s), 6.87(1H, d), 6.99(2H, m), 7.17(1H, m), 7.29(2H, m), 7.49(1H, m), 7.92(1H, d), 10.49(1H, s) |
| 12 | H | H | 3-OCF₃ | $\delta_H$(CDCl₃, 400MHz)6.97(3H, m), 7.03(1H, d), 7.26(1H, m), 7.40(1H, m), 7.57(1H, m), 7.98(1H, m), 10.45(1H, s); MSm/z(TS⁺)300(MNH₄⁺). |
| 13 | H | MeO | 4-SMe | $\delta_H$(CDCl₃, 300MHz)2.48(3H, s), 3.86(3H, s), 6.90 (3H, m), 7.10(1H, dd), 7.26(2H, d), 7.40(1H, d), 10.39(1H, s) |
| 14 | Br | H | 4-SMe | $\delta_H$(CDCl₃, 300MHz)2.50(3H, s), 7.00–7.06(3H, m), 7.29–7.34(3H, m), 7.88(2H, d), 10.46(1H, s) |
| 15 | H | H | 4-Br | $\delta_H$(CDCl₃, 300MHz)6.90(1H, d), 6.94(2H, d), 7.22(1H, t), 7.48(2H, d), 7.52(1H, m), 7.94(1H, d), 10.46(1H, s) |
| 16[a] | H | Br | 3-OMe 4-SMe | $\delta_H$(CDCl₃, 300MHz)2.46(3H, s), 3.89(3H, s), 6.65 (2H, m), 6.83(1H, d), 7.20(1H, d), 7.40(1H, dd), 8.04(1H, d), 10.46(1H, s); MSm/z(TS⁺)370/372 (MNH₄⁺) |
| 17[b] | H | Br | 3-CF₃ 4-SMe | $\delta_H$(CDCl₃, 300MHz)2.55(3H, s), 6.81(1H, d), 7.20(1H, d), 7.40(1H, s), 7.46(1H, d), 7.66(1H, d), 8.08(1H, s), 10.43(1H, s) |

-continued

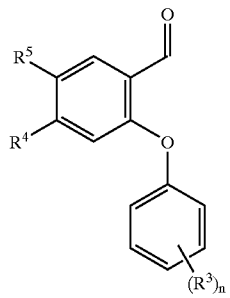

| Preparation | R⁴ | R⁵ | (R³)ₙ | Data |
|---|---|---|---|---|
| 18 | MeO | MeO | 4-SMe | $\delta_H$(CDCl₃, 400MHz)2.48(3H, s), 3.82(3H, s), 3.93 (3H, s), 6.43(1H, s), 6.95(2H, d), 7.28(2H, d), 7.38 (1H, s), 10.25(1H, 5), MSm/z(TS⁺)305(MH⁺). |

ᵃThe phenol of preparation 35 was used.
ᵇThe phenol of preparation 34 was used.

PREPARATIONS 19–20

The following diphenylethers were prepared in an analogous fashion to the reaction described for preparation 1 using 2-chloro-5-nitrobenzaldehyde with the appropriate commercially available phenol. Shorter reaction times (ca. 3 h) were sufficient to achieve good conversions in these cases.

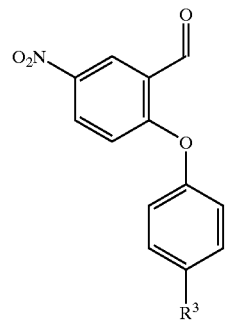

| Preparation | R³ | data |
|---|---|---|
| 19 | —SMe | $\delta_H$(CDCl₃, 400MHz)2.53(3H, s), 6.90(1H, d), 7.10(2H, m), 7.37 (2H, m), 8.30(1H, dd), 8.79(1H, d), 10.58(1H, s); MSm/z(TS⁺) 307(MNH₄⁺). |
| 20 | —CF₃ | $\delta_H$(CDCl₃, 400MHz)6.98(1H, d), 7.27(2H, d), 8.36(1H, dd), 8.83 (1H, d), 10.55(1H, s); MSm/z(TS⁺)311(MH⁺) |

PREPARATION 21

N,N-Dimethyl-N-{2-[4-(methylsulfanyl)phenoxy]benzyl}amine

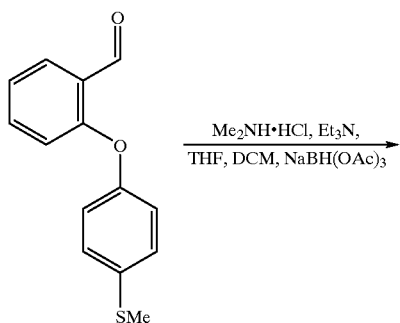

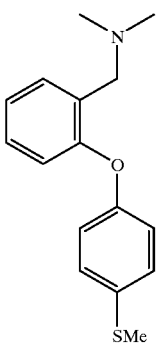

The aldehyde of preparation 1 (21.23 g, 87 mmol) was dissolved in a 1:1 mixure of THF and DCM (180 mL each) together with dimethylamine hydrochloride (7.81 g, 95.8 mmol) and triethylamine (36.4 mL, 261 mmol). Sodium triacetoxyborohydride (27.7 g, 130.7 mmol) was then added to the reaction mixture stirred at room temperature under a nitrogen atmosphere overnight. The reaction mixture was evaporated, and then partitioned between DCM and water (1000 mL each). The organic layer was separated, dried (MgSO$_4$) and then evaporated to a brown oil. The residue could be purified by flash chromatography [SiO$_2$; {(MeOH/880 NH$_3$) (9:1)} (0→5%) in DCM] to afford the desired amine free base compound as a brown oil; $\delta_H$(CDCl$_3$, 400 MHz) 2.26 (6 H, s), 2.46 (6 H, s), 3.45 (2 H, s), 6.84–6.90 (3 H, m), 7.13 (1 H, t), 7.20–7.26 (3 H, m), 7.46 (1 H, d); MS m/z (TS$^+$) 274 (MH$^+$). Alternatively, the crude reaction product could be purified by formation and crystallisation of the hydrochloride salt by dissolution in diethyl ether (150 mL) followed by addition of hydrochloric acid (1 M) in diethyl ether (150 mL) to the stirred solution. The hydrochloride salt of the desired dimethylamine compound was collected as a white solid (22.58 g, 84%); $\delta_H$(CDCl$_3$, 400 MHz) 2.43 (3 H, s), 2.80 (6 H, d), 4.32 (2 H, s), 6.86 (1 H, d), 6.93 (2 H, d), 7.20 (1 H, t), 7.25 (2 H, m), 7.36 (1 H, dt) 7.85 (1 H, dd), 12.47 (1 H, br).

Alternatively, the hydrochloride salt of the title compound can be prepared as follows.

A solution of the product from preparation 1 (390 g, 1.59 mol) in DCM (2.73 L) was added to THF (2.73 L). To that was added dimethylamine hydrochloride (143 g, 1.75 mol) and triethylamine (485 g, 4.80 mol) successively. The temperature was adjusted to 20° C. and after 1 h sodium triacetoxyborohydride (508 g, 2.93 mol) was added. After 20 h, dichloromethane (3.9 L) was added and a solution of 8% sodium bicarbonate (3.9 L) was added over 0.5 h. The layers were separated and the organic layer washed with water (2.5 L). The layers were again separated and the organic layer was concentrated to a volume of 1.65 L. Ethyl acetate (2.89 L) was added and the solvent removed replacing with fresh ethyl acetate to give a final volume of 2.92 L. The solution was then cooled to below 5° C. and 6.75 M hydrochloric acid in isopropanol (0.25 L, 1.69 mol) added maintaining the temperature below 10° C. After stirring for 1 h at below 5° C., the slurry was filtered, washed with ethyl acetate (2×0.39 L) and dried in a vacuum oven at 50° C. overnight to give the desired product as a powdery solid (308.3 g, 63%).

PREPARATIONS 22–25

The amines of Preparations 22 to 25 were prepared according to the process described in preparation 21.

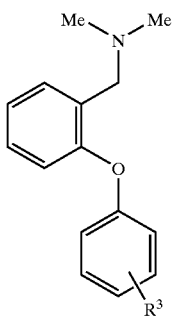

| Preparation | Starting Material | R$^3$ | Data |
|---|---|---|---|
| 22 (HCl salt) | Prep. 4 | 4-CF$_3$ | $\delta_H$(CDCl$_3$, 300MHZ)2.79(6H, s), 4.28(2H, s), 6.96(1H, d), 7.06(2H, d), 7.29(1H, t), 7.42(1H, t), 7.63(2H, d), 7.95(1H, d); MSm/z(TS$^+$)296 (MH$^+$). |
| 23 | Prep. 6 | 4-OCF$_3$ | $\delta_H$(CDCl$_3$, 300MHz)2.25(6H, s), 3.44(2H, s), 6.92(3H, m), 7.17(3H, m), 7.23(1H, m), 7.49 (1H, d); MSm/z(TS$^+$)312(MH$^+$). |

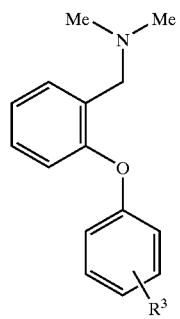

| Preparation | Starting Material | R³ | Data |
|---|---|---|---|
| 24 | Prep. 12 | 3-OCF₃ | $\delta_H$(CDCl₃, 400MHz)2.23(6H, s), 3.41(2H, s), 6.78(1H, s), 6.83(1H, d), 6.90(1H, d), 6.97(1H, d), 7.18(1H, m), 7.28(2H, m), 7.49(1H, d); MS m/z(TS⁺)312(MH⁺). |
| 25 | Prep 15 | 4-Br | HCl salt: $\delta_H$(d₆-DMSO, 400MHz)2.71(6H, s), 4.30(2H, s), 6.87(1H, d), 7.07(2H, d), 7.22(1H, t), 7.42(1H, t), 7.60(2H, d), 7.78(1H, d) |

PREPARATION 26

N-Methyl-N-{2-[4-(trifluoromethoxy)phenoxy]benzyl}amine

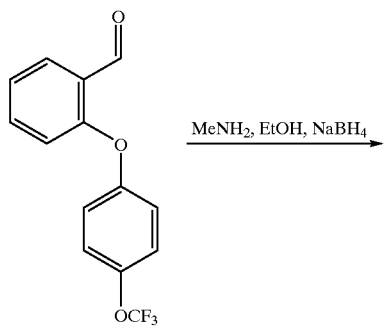

The aldehyde compound of preparation 6 (2.5 g, 8.86 mmol) was dissolved in a solution of monomethylamine in ethanol (ca. 8 M) (11 mL, 88 mmol), and the mixture stirred at room temperature overnight. THF/ ethanol (1:1) was added to the mixture to aid dissolution and sodium borohydride (3.35 g, 88.6 mmol) was added. Stirring was continued for 4 h before the reaction was quenched by cautious addition of hydrochloric acid (1 M) (until gas evolution ceased). The mixture was basified with aqueous sodium hydroxide (2 M), and then extracted with ethyl acetate (3 times). The combined organic fractions were dried (MgSO₄) and evaporated to an oil which was purified by flash chromatography [SiO₂; DCM/ MeOH/ 880 NH₃ (93:7:1)] to afford the desired amine compound as a colourless oil (2.23 g, 84%); 8H (CDCl₃, 300 MHz) 1.72 (1 H, br), 2.42 (3 H, s), 3.77 (2 H, s), 6.92 (3 H, m), 7.16 (3 H, m), 7.23 (1 H, m), 7.41 (1 H, d); MS m/z (TS⁺) 298 (MH⁺).

PREPARATION 27

N-Methyl-N-{2-[4-(trifluoromethyl)phenoxy]benzyl}amine

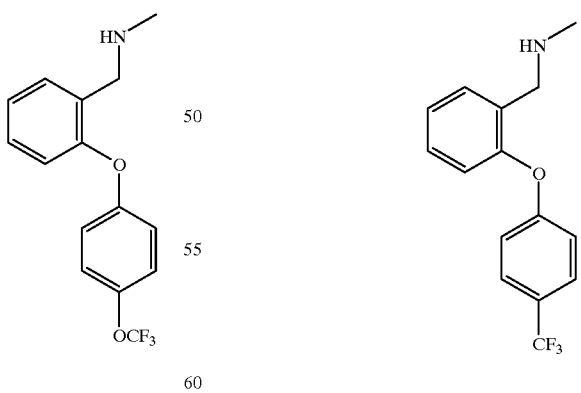

The title amine was synthesised using the conditions described for preparation 26 starting from the aldehyde compound of Preparation 4; $\delta_H$(CDCl₃, 300 MHz) 2.57 (3 H, s), 4.14 (2 H, s), 5.50 (2 H, brs), 6.88 (1 H, d), 7.18 (3 H, m), 7.34 (1 H, t), 7.61 (2 H, d), 7.70 (1 H, d); MS m/z (TS⁺) 282 (MH⁺).

PREPARATION 28

N-Methyl-N-{2-[4-(methylsulfanyl)phenoxy]benzyl}amine

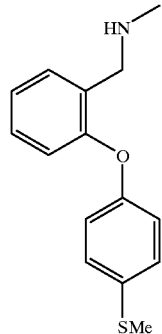

The title amine was prepared from the aldehyde of preparation 1 according to the method described for preparation 26; $\delta_H$(CD$_3$OD, 300 MHz) 2.41 (3 H, s), 2.45 (3 H, s), 3.80 (2 H, s), 6.84 (1 H, d), 6.94 (2 H, d), 7.15 (1 H, m), 7.28 (3 H, m), 7.43 (1 H, d); MS m/z (TS$^+$) 260 (MH$^+$).

PREPARATION 29

N-{2-[4-(Ethylsulfanyl)phenoxy]benzyl}-N,N-dimethylamine

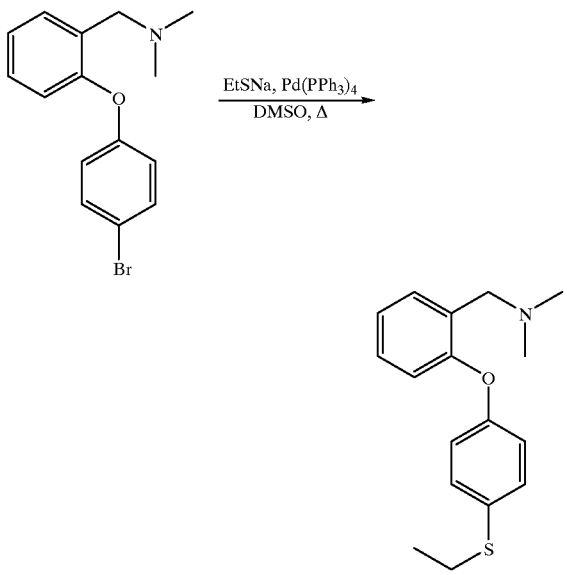

The product from preparation 25 (1.09 g, 3.18 mmol) was dissolved in DMSO (3.2 mL) and treated with sodium ethanethiolate (535 mg, 6.36 mmol) and palladium tetrakis(triphenylphosphine) (367 mg, 1155.57). The mixture was stirred and heated to 100° C. overnight. After cooling to room temperature, the mixture was partitioned between water and diethyl ether (100 mL each). The organic layer was separated and the aqueous layer re-extracted with diethyl ether (100 mL). The combined ether layers were washed with brine (100 mL), dried (MgSO$_4$) and evaporated to a bright red oil. Purification by flash chromatography [SiO$_2$; DCM/ MeOH/ 880 NH$_3$ (93:7:1)] afforded an orange oil which was dissolved in ethyl acetate (10 mL) and treated with hydrochloric acid (1 M) in diethyl ether (5 mL). The solvents were evaporated to afford a beige solid which was recrystallised from boiling ethyl acetate to give a cream powder (491 mg, 54%); 1.30 (3 H, t), 2.80 (6 H, d), 2.92 (2 H, q), 4.31 (2 H, d), 6.88 (1 H, d), 6.94 (2 H, d), 7.23 (1 H, t), 7.38 (2 H, d), 7.87 (1 H, d); MS m/z (ES$^+$) 288 (MH$^+$)

PREPARATION 30

5-(Aminosulfonyl)-2-[3-methoxy-4-(methylsulfanyl)phenoxy]-N-methylbenzamide

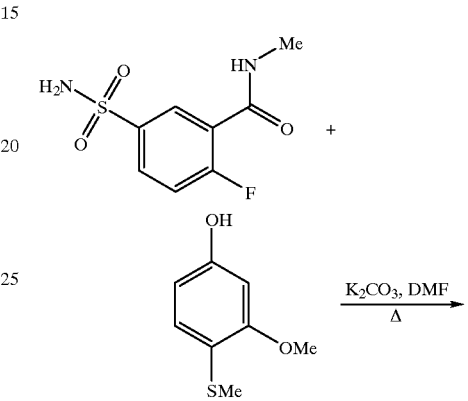

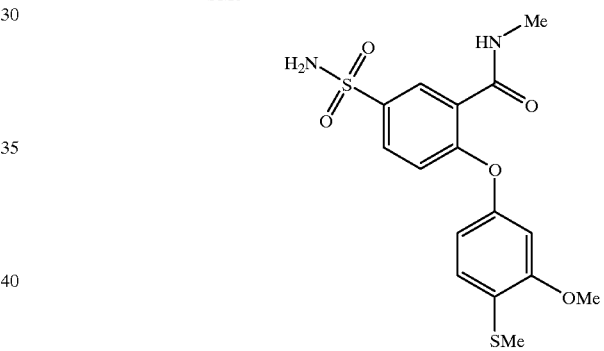

The sulfonamide from preparation 67 (405 mg, 1.7 mmol) was combined with the phenol of preparation 35 (297 mg, 1.7 mmol), potassium carbonate (362 mg, 2.6 mmol) and DMF (10 mL), and the mixture was then heated at 110° C. for 18 hours. After cooling to room temperature the reaction mixture was diluted with water, acidified to pH 3 with hydrochloric acid (2 M) and extracted with ethyl acetate (2×75 mL). The organic layers were combined, dried (MgSO$_4$) and evaporated to dryness. The residue was purified by flash chromatography [SiO$_2$; DCM/ MeOH/ 880 NH$_3$ (93:7:1→90:10:1)] to afford the title amide as a brown oil (600 mg, 90%); $\delta_H$(DMSO-d$_6$, 400 MHz) 2.33 (3 H, s), 2.75 (3 H, d), 3.75 (3 H, s), 6.69 (1 H, d), 6.82 (1 H, s), 6.86 (1 H, d), 7.16 (1 H, d), 7.30 (2 H, s), 7.75 (1 H, d), 8.07 (1 H, s), 8.25 (1 H, m); MS m/z (TS$^+$) 383 (MH$^+$).

PREPARATIONS 31–33

The amides below were prepared by the procedure described for preparation 30 using the sulfonamide of preparation 67 and the appropriate phenol as indicated.

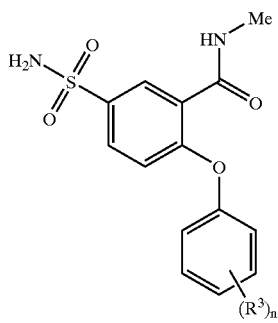

| Preparation | Starting Material | $(R^3)_n$ | $^1$H NMR Data |
|---|---|---|---|
| 31 | — | 4-SMe | $\delta_H$(CDCl$_3$, 400MHz)2.46(3H, s), 3.46(3H, s), 4.27 (2H, d), 7.64(1H, d), 11.60(1H, br); MSm/z(TS$^+$)363 (MH$^+$). |
| 32 | Prep 36 | 4-OMe 3-SMe | $\delta_H$(CD$_3$OD, 400MHz)2.36(3H, s), 2.96(3H, s), 3.87 (3H, s), 6.87(2H, m), 6.99(2H, m), 7.86(1H, d), 8.34 (1H, s); MSm/z(ES$^-$)381(MH$^+$). |
| 33 | Prep 34 | 3-CF$_3$ 4-SMe | $\delta_H$(CDCl$_3$, 400 MHz)2.56(3H, s), 3.52(3H, s), 4.39 (2H, s), 7.04(1H, d), 7.12(1H, s), 7.31(2H, d), 7.40 (1H, d), 7.71(1H, d) |

PREPARATION 34

4-(Methylsulfanyl)-3-(trifluoromethyl)phenol

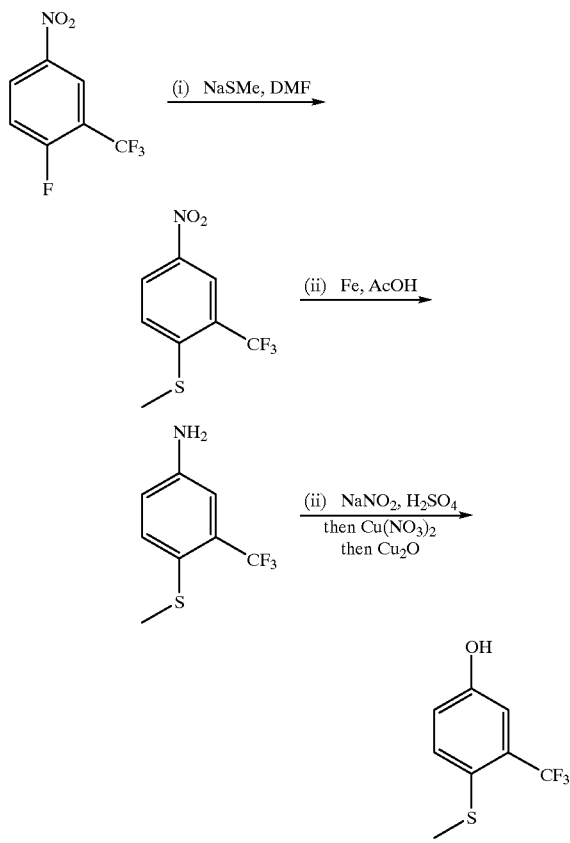

(i) Sulfide formation: 1-(methylsulfanyl)-4-nitro-2-(trifluoromethyl)benzene

2-Fluoro-5-nitrobenzotrifluoride (30 mL, 218.4 mmol) was dissolved in DMF (218 mL) and treated with 4,4'-thiobis-(6-tert-butyl-meta-cresol) (150 mg, 0.4 mmol) then sodium methanethiolate (15 g, 214 mmol). The reaction mixture was stirred at room temperature overnight, after which time it was evaporated to a low volume. The residue was partitioned between diethyl ether and water (1000 mL each). The organic fraction washed sequentially with water and brine (750 ml each), dried (MgSO$_4$) and evaporated to a yellow oil. Purification by flash chromatography [SiO$_2$; ethyl acetate/ pentane (5:95→10:90)] afforded a mixture of two compounds which was further purified by flash chromatography [SiO$_2$; DCM/ pentane (10:90→40:60)] to afford the title sulfide (7.96 g, 15%); $\delta_H$(CDCl$_3$, 400 MHz) 2.58 (3 H, s), 7.39 (1 h, d), 8.28 (1 H, dd), 8.46 (1 H, d)

(ii) Nitro reduction: 4-(methylsulfanyl)-3-(trifluoromethyl)aniline

A suspension of the sulfide from stage (i) in acetic acid (168 mL) and water (25 mL) was treated with iron powder (11.25 g, 201 mmol). The mixture was stirred at room temperature for 2 hours before being evaporated to a small volume. The residue was partitioned between saturated NaHCO$_{3(aq)}$, ethyl acetate (200 mL each) then filtered through a plug of arbocel®. The organic layer was separated and the aqueous layer re-extracted with ethyl acetate (2×100 mL). The combined organic layers were dried (MgSO$_4$) and evaporated to a brown oil of the title aniline slightly contaminated with acetic acid (8 g ca. 100%); $\delta_H$ (CDCl$_3$, 400 MHz) 2.40 (3 H, s), 6.77 (1 H, dd), 6.95 (1 H, d), 7.32 (1 H, d).

(iii) Diazonium salt formation/ hydrolysis: 4-(methylsulfanyl)-3-(trifluoromethyl)phenol A suspension of the aniline from stage (ii) (8.00 g, 38.2 mmol) in water was treated with concentrated sulfuric acid (20 mL) and cooled to 0° C. with vigorous stirring. Solution of sodium nitrite (2.9 g, 42.1 mmol) in water (15 mL) was added dropwise, and upon completion of the addition the mixture was stirred at this temperature for a further 30 minutes by which time dissolution had occurred. A solution of copper(ll) nitrate hemipentahydrate (120 g, 516 mmol) in water (900 mL) was added followed by solid copper(l) oxide (4.9 g, 34.4 mmol). Vigorous stirring was continued until nitrogen evolution subsided (10–15 minutes). The reaction mixture was extracted with diethyl ether (2×400 mL) and these combined organics were extracted with aqueous sodium hydroxide (1M) (3 x 100 mL). The combined NaOH fractions were acidified to pH 2 with concentrated hydrochloric acid, and extracted with diethyl ether (2×150 mL). The combined organic fractions were washed with brine, dried (MgSO$_4$) and evaporated to a brown oil (3.5 g, 44%): $\delta_H$(CDCI$_3$, 400 MHz) 2.44 (3 H, s), 5.50 (1 H, brs), 6.97 (1 H, dd), 7.16 (1 H, d), 7.38 (1 H, d); MS m/z (ES$^+$) 207 (M-H$^+$)

PREPARATION 35

3-Methoxy4-(methylsulfanyl)phenol

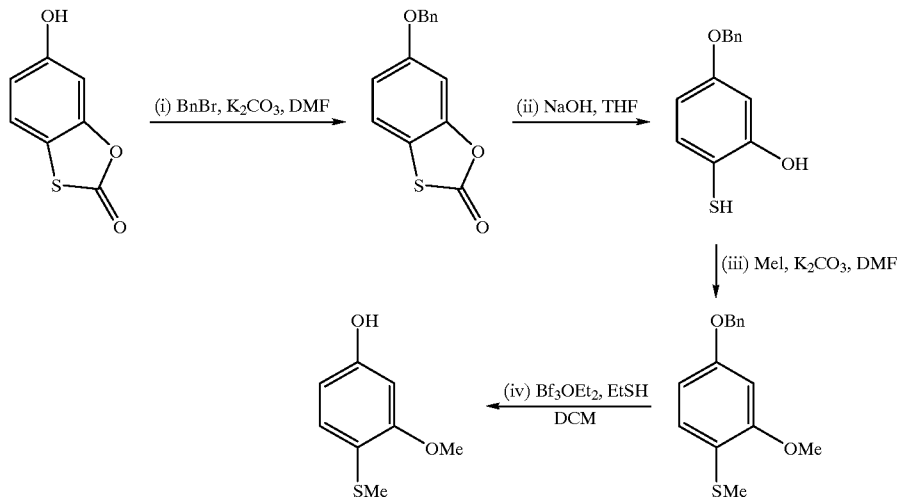

(i) Formation of benzylether: 6-(benzyloxy)-1,3-benzoxathiol-2-one

6-Hydroxy-1,3-benzoxathiol-2-one (50 g, 297 mmol) was dissolved in DMF (500 mL), and treated with benzyl bromide (53 mL, 446 mmol) and potassium carbonate (82 g, 595 mmol). The mixture was heated at 60° C. under a nitrogen atmosphere overnight before being evaporated to dryness. The residue was partitioned between diethyl ether (700 mL) and water (400 mL) and the organic layer separated. The aqueous layer was re-extracted with diethyl ether (2×800 mL) and the combined organic fractions washed with water (2×500 mL), dried (MgSO$_4$), and evaporated to a yellow oil. Purification by flash chromatography [SiO$_2$; ethyl acetate/ pentane (1:19→1:9)] gave a gummy white solid which was triturated with Et$_2$O/ pentane to give a white solid of the desired benzylether (17.65 g, 23%); $\delta_H$(CDCI$_3$, 300 MHz) 5.10 (2 H, s), 6.92 (1 H, d), 6.98 (1 H, s), 7.28 (1 H, d), 7.35–7.45 (5 H, m); MS m/z (TS$^+$) 276 (MNH$_4^+$).

(ii) Hydrolysis of the thioxolone ring: 5-(benzyloxy)-2-sulfanylphenol

The benzylether from step (i) (17.55 g, 67.9 mmol) was dissolved in THF (125 mL) and treated with aqueous sodium hydroxide (2 M; 125 mL). After stirring at room temperature for 2 hours the mixture was evaporated to remove THF and the remaining aqueous solution was washed with diethyl ether (3×10 mL). The aqueous layer was then acidified with concentrated hydrochloric acid to pH 1 causing the mixture to effervesce. The mixture was then extracted with diethyl ether (3×100 mL) and the combined extracts were washed with brine (100 mL), dried (MgSO$_4$) and evaporated to a yellow oil (13.65 g, 86 %); $\delta_H$(CDCI$_3$, 300 MHz) 5.08 (2 H, s), 6.40 (1 H, s), 6.55 (1 H, d), 6.63 (1 H, s), 7.30–7.45 (5 H, m); MS m/z (TS$^+$) 250 (MNH$_4^+$).

(iii) Methylation of the phenol and thiophenol: 4-(benzyloxy)-2-methoxy-1-(methylsulfanyl)benzene A mixture of the thiophenol-phenol from stage (ii) (13.5 g, 58.1 mmol) and potassium carbonate (9.64 g, 69.7 mmol) in DMF (150 mL) at 0° C. was treated with methyl iodide (7.97 mL, 128 mmol). The mixture was allowed to reach room temperature and stirred for 3 days The reaction was evaporated to dryness and the residue partitioned between water (150 mL) and diethyl ether (150 mL). The aqueous layer was removed and extracted further with diethyl ether (2×75 mL). the combined organic layers were washed with water (2×50 mL), brine (50 mL), dried (MgSO$_4$) and evaporated to a yellow oil. Purification by flash chromatography [SiO$_2$; ethyl acetate in pentane (2% →4%)] afforded an oil which solidified to a white solid after drying under vacuum (11.5 g, 65%); $\delta_H$(CDCI$_3$, 300 MHz) 2.40 (3 H, s), 3.90 (3 H, s), 5 08 (2 H, s), 6.57 (2 H, s), 7.20 (1 H, dd), 7.35–7.45 (5 H, m); MS m/z (TS$^+$) 261 (MH$^+$).

(iv) Cleavage of the benzylether: 3-methoxy-4-(methylsulfanyl)phenol

The benzylether from stage (iii) (9.27 g, 39.5 mmol) was dissolved in DCM (5 mL), ethanethiol (5 mL) and BF$_3$.OEt$_2$ (5 mL, 39.5 mol) were then added at room temperature under a nitrogen atmosphere. The mixture was stirred overnight before the reaction was quenched with hydrochloric acid (2 M) and stirred for a further 30 mins. The mixture was then basified by the addition of sodium hydroxide (2 M) until pH 10 was attained. The mixture was then washed with ethyl acetate (3×50 mL). The aqueous layer was reacidified by the addition of hydrochloric acid (2 M) to pH 1 and extracted with ethyl acetate (4×50 mL). The extracts were combined, dried (MgSO$_4$) and evaporated to an oil. Purification by flash chromatography [SiO$_2$; EtOAc/ pentane (1:9→1:4)] afforded the desired phenol compound as a colourless solid (1.73 g, 28%); $\delta_H$(CDCI$_3$, 400 MHz) 2.21 (3 H, s), 3.70 (3 H, s), 6.30 (1 H, d), 6.35 (1 H, s), 6.96 (1 H, d), 9.39 (1 H, brs)

PREPARATION 36

4-Methoxy-3-(methylsulfanyl)phenol

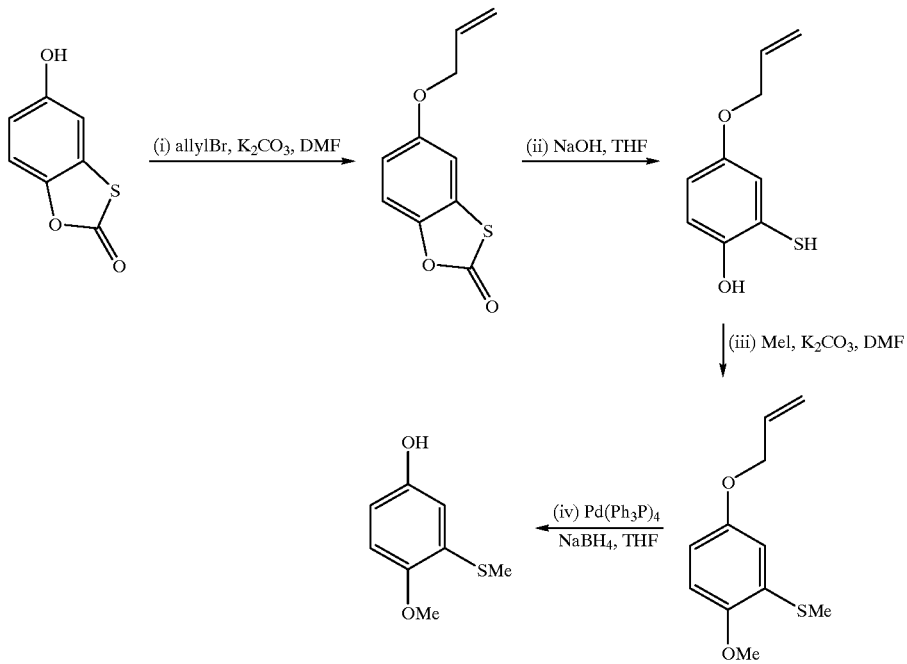

(i) Formation of allylether: 5-(allyloxy)-1,3-benzoxathiol-2-one

5-Hydroxy-1,3-benzoxathiol-2-one (2g, 11.9 mmol) [prepared according to *J. Org. Chem.* 1990, 55, 2736] was dissolved in acetone (13 mL) and treated with potassium carbonate (3.29 g, 23.8 mmol) followed by allyl bromide (1.13 mL, 13.1 mmol). The mixture was then stirred under nitrogen atmosphere for 24 hours. The reaction mixture was evaporated to dryness and the residue was partitioned between water and diethyl ether (50 mL each). The organic fraction was separated and the aqueous layer re-extracted with diethyl ether (50 mL). The combined organic fractions were dried (MgSO$_4$) and evaporated to a brown oil. Purification by flash chromatography [SiO$_2$; pentane/ethyl acetate (95:5→90:10)] afforded the desired compound as a colourless oil (1.9 g, 77%); $\delta_H$(CDCl$_3$, 400 MHz) 4.50 (2 H, d), 5.28 (1 H, d), 5.38 (1 H, d), 6.00 (1 H, ddt), 6.83 (1 H, dd), 6.91 (1 H. d), 7.15 (1 H, d)

(ii) Hydrolysis of the thiocarbonate: 4-(allyloxy)-2-sulfanylphenol

The allyl ether from stage (i) (834 mg) was dissolved in degassed THF (5 mL) and treated with degassed aqueous sodium hydroxide (2 M; 5 mL, 10 mmol). After stirring for 30 minutes the solution was acidified with hydrochloric acid (2 M) to pH 1 causing the mixture to effervesce. The mixture was extracted with diethyl ether (2×30 mL) and the combined extracts were dried (MgSO$_4$) and evaporated to a clear oil which used directly in the next stage; $\delta_H$(CDCl$_3$, 300 MHz) 3.13 (1 H, s), 4.49 (2 H, d), 5.30 (1 H, d), 5.44 (1 H, dt), 5.76 (1 H, s), 5.97–6.12 (1 H, m), 6.79–6.96 (2 H, m), 7.16–7.25 (1 H, m).

(iii) Methylation of the phenol and thiophenol: 4-(allyloxy)-1-methoxy-2-(methylsulfanyl)benzene The thiophenol from stage (ii) was added as a solution in acetone (4 mL) to a slurry of potassium carbonate (1.66 g, 12 mmol) in acetone (4 mL) and methyl iodide (623 microlitres, 10 mmol). The mixture was stirred at room temperature overnght and then evaporated to a gummy solid. This residue was partitioned between diethyl ether and water (50 mL each) and the organic layer separated. The aqueous layer was re-extracted with diethyl ether (50 mL) and the combined organic fractions were dried (MgSO$_4$) and evaporated to an oil. Purification by flash chromatography [SiO$_2$, pentanel ethyl acetate (19:1→10:1] afforded the title ally ether as an oil (556 mg, 66%); $\delta_H$(CDCl$_3$, 400 MHz) 2.38 (3 H, s), 3.81 (3 H, s), 4.44 (2 H, d), 5.23 (1 H, d), 5.36 (1 H, d), 6.00 (1 H, ddt), 6.61 (1 H, d), 6.69–6.72 (2 H, m)

(iv) Deallylation of allylether: 4-methoxy-3-(methylsulfanyl)phenol

The allyl ether from stage (iii) (556 mg, 2.64 mmol) was dissolved in dry THF (26 mL) together with palladium tetrakis(triphenylphosphine) (153 mg, 0.13 mmol) and the mixture was cooled to 0° C. Sodium borohydride (600 mg, 15.9 mmol) was added and the mixture was allowed to reach room temperature and stirred overnight. The reaction had proceeded to ca. 50% conversion as judged by TLC anlysis and so a further batch of palladium tetrakis (triphenylphosphine) (153 mg, 0.13 mmol) was added and the mixture warmed to 45 ° C. and stirred for a further 12 hours. The reaction was quenched by the cautious addition of sat. NH$_4$Cl$_{(aq)}$ (until effervescence ceased) and the resulting mixure was extracted with ethyl acetate (3×50 mL). The combined extracts were dried (MgSO$_4$) and evaporated to a yellow-orange oil. Purification by flash chromatography [SiO$_2$; DCM/ MeOHI 880 NH$_3$ (93:7:1)] afforded the desired title phenol as a colourless oil (425 mg, 90%); $\delta_H$(CDCl$_3$, 400 MHz) 2.39 (3 H, s), 3.83 (3 H, s), 4.97 (1 H, s), 6.57 (1 H, dd), 6.67 (1 H, S), 6.68 (1 H, d).

PREPARATION 37 tert-Butyl 5-bromo-2-[4-(methylsulfanyl)-3-(trifluoromethyl)phenoxy]benzyl-(methyl)carbamate

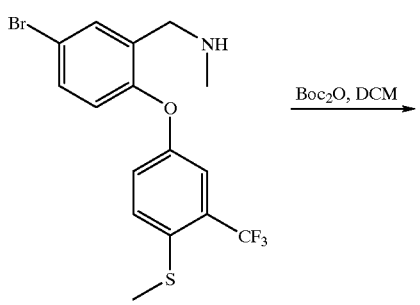

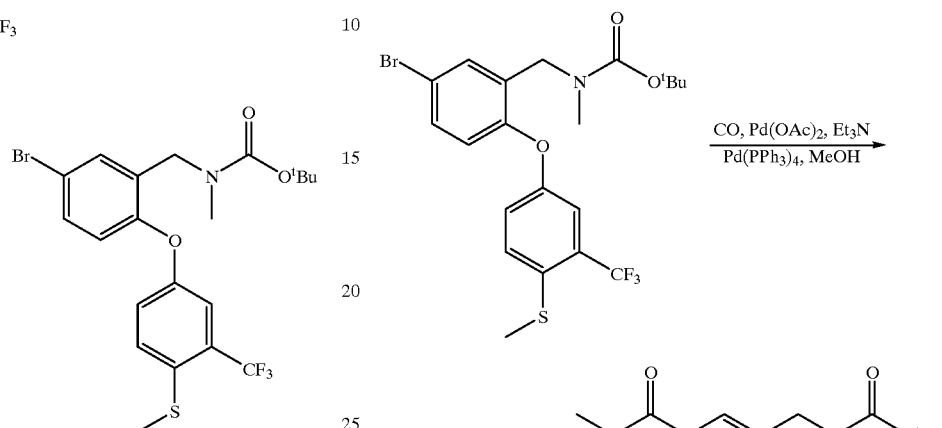

PREPARATION 40

Methyl 3-{[(tert-butoxycarbonyl)(methyl)amino]methyl}-4-[4-(methylsulfanyl)-3-(trifluoromethyl)phenoxy]benzoate A solution of the amine from example 27 (822 mg, 2.02 mmol) in DCM (10 mL) was treated with di(tert-butyl) dicarbonate (530 mg, 2.43 mmol) at room temperature. After stirring for 1 hour the reaction mixture was washed with hydrochloric acid (2M) (5 mL), saturated aqueous sodium bicarbonate (5 mL), dried (MgSO$_4$) and evaporated to a pale yellow oil (1.17 g, ca. 100%); $\delta_H$(CDCl$_3$, 300 MHz) 1.57 (9H, brs), 2.50 (3 H, brd), 2.87 (3 H, brs), 4.43 (2 H, brs), 6.78 (1 H, brt), 7.04 (1 H, brs), 7.27 (1 H, obs), 7.33–7.50 (3 H, brm); MS m/z (TS$^+$) 508 (MH$^+$)

PREPARATIONS 38–39

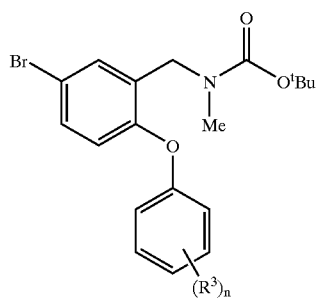

The following Boc-protected aryl bromides were prepared by the method described for Preparation 37 from the appropriate secondary amine.

| Preparation | Starting Material | (R$^3$)$_n$ | data |
|---|---|---|---|
| 38 | Example 26 | 3-OMe 4-SMe | $\delta_H$(CDCl$_3$, 400MHz)1.48 (9H, brm), 2.40(3H, s), 2.90 (3H, brm), 3.85(3H, s)4.45(2H, brm), 6.45(1H, dd), 6.54(1H, d), 6.72(1H, d), 7.14(1H, d), 7.32(1H, dd), 7.39(1H, brs); MSm/z(TS$^+$)470(MH$^+$) |
| 39 | Example 23 | 4-SMe | $\delta_H$(CDCl$_3$, 400MHz)1.39(9H, s), 2.41(3H, s), 2.83 (3H, br), 4.39(2H, brs), 6.68(1H, d), 6.80(2H, d), 7.15–7.30(3H, m), 7.35(1H, s); MSm/z(TS$^+$)440(MH$^+$), 340 ([M-Boc]H$^+$) |

The arylbromide from preparation 37 (1.02 g, 2.02 mmol) was dissolved in methanol (15 mL) and treated with triethylamine (0.85 mL, 6.60 mmol), palladium(II) acetate (45 mg, 0.202 mmol), triphenylphosphine (106 mg, 0.404 mg) in a stainless steel vessel. The mixture was placed under 100 psi of carbon monoxide and heated to 100° C. for 24 hours. The solution was then evaporated to dryness and the residue purified by flash chromatography [SiO$_2$; ethyl acetate/ pentane (1:9→1:3)] to afford the title ester as a yellow oil (412 mg, 42%), δ$_H$(CDCl$_3$, 400 MHz) 1.41 (9 H, s), 2.46 (3 H, s), 2.85 (3 H, brs), 3.87 (3 H, s), 4.50 (2 H, brs), 6.79 (1 H, d), 7.07 (1 H. d), 7.28 (1 H, s), 7.38 (1 H, d), 7.87 (1 H, d), 7.97 (1 H, brs); MS m/z 397 [M—(OMe)—(t—Bu)]

PREPARATIONS 41–42

The following esters were prepared by the method described in Preparation 40 from the requisite aryl bromide.

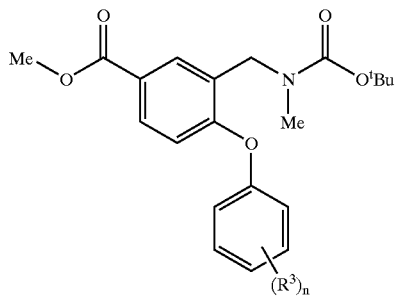

| Preparation | Starting Material | (R³)$_n$ | data |
|---|---|---|---|
| 41 | Preparation 38 | 3-OMe 4-SMe | δ$_H$(CDCl$_3$, 400MHz)1.50(9H, s), 2.46(3H, s), 2.94 (3H, brs), 3.87(3H, s), 3.92(3H, s), 4.57(2H, brm), 6.59(2H, m), 6.84(1H, d), 7.89(1H, d), 800(1H, brm); MSm/z(TS⁺)448(MH⁺) |
| 42 | Preparation 39 | 4-SMe | δ$_H$(CDCl$_3$, 400MHz)1.42(9H, s), 2.43(3H, s), 2.90 (3H, brs), 3.85(3H, s), 4.51(2H, brd), 6.76(1H, d), 6.91(2H, d), 7.28(2H, m), 7.83(1H, d), 7.95(1H, brd); MSm/z(TS⁺)418(MH⁺) |

PREPARATION 43

3-{[(tert-Butoxycarbonyl)(methyl)amino] methyl}-4-[4-(methylsulfanyl )-3-(trifluoromethyl)phenoxy]benzoic acid

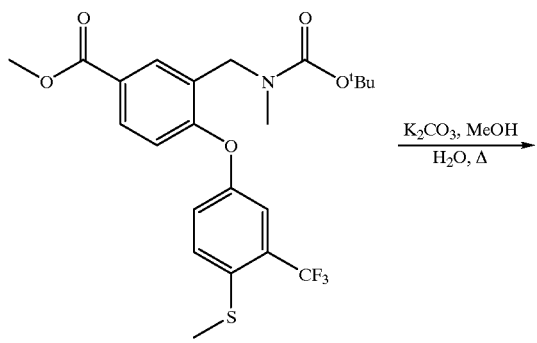

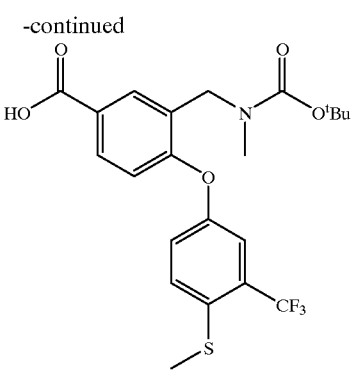

The ester from preparation 40 (400 mg, 0.82 mmol) was dissolved in methanol (5 mL) and water (2 mL), and potassium carbonate (114 mg, 0.82 mmol) was added. The reaction mixture was then heated at reflux for 18 hours. After cooling to room temperature the mixture was evaporated to dryness and the residue diluted with ethyl acetate (10 mL) and water (5 mL) and acidified with hydrochloric acid (2 M) (2–3 mL). The organic layer was separated and the aqueous layer re-extracted with ethyl acetate (5 mL). The combined organic fractions were washed with brine (5 mL), dried (MgSO$_4$) and evaporated to a yellow oil (388 mg, 100%); δ$_H$(CDCl$_3$, 300 MHz) 1.47 (9H, s), 2.54 (3 H, s), 2.95 (3 H, brs), 4.57 (2 H, brs), 6.83 (1 H, d), 7.15 (1 H, dd), 7.35 (1 H, s), 7.42 (1 H, d), 7.99 (1 H, d), 8.07 (1 H, brs); MS m/z (TS⁺) 489 (MNH$_4$⁺)

PREPARATION 44

3-{[(tert-Butoxycarbonyl)(methyl)amino]methyl}-4-[4-(methylsulfanyl)phenoxy]benzoic acid

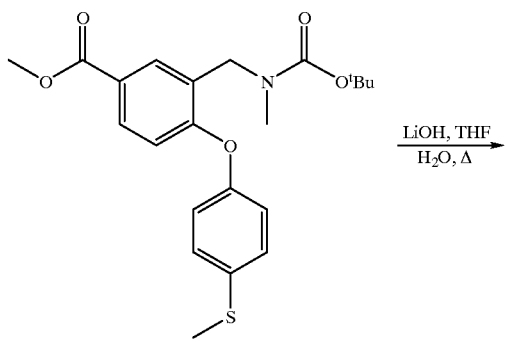

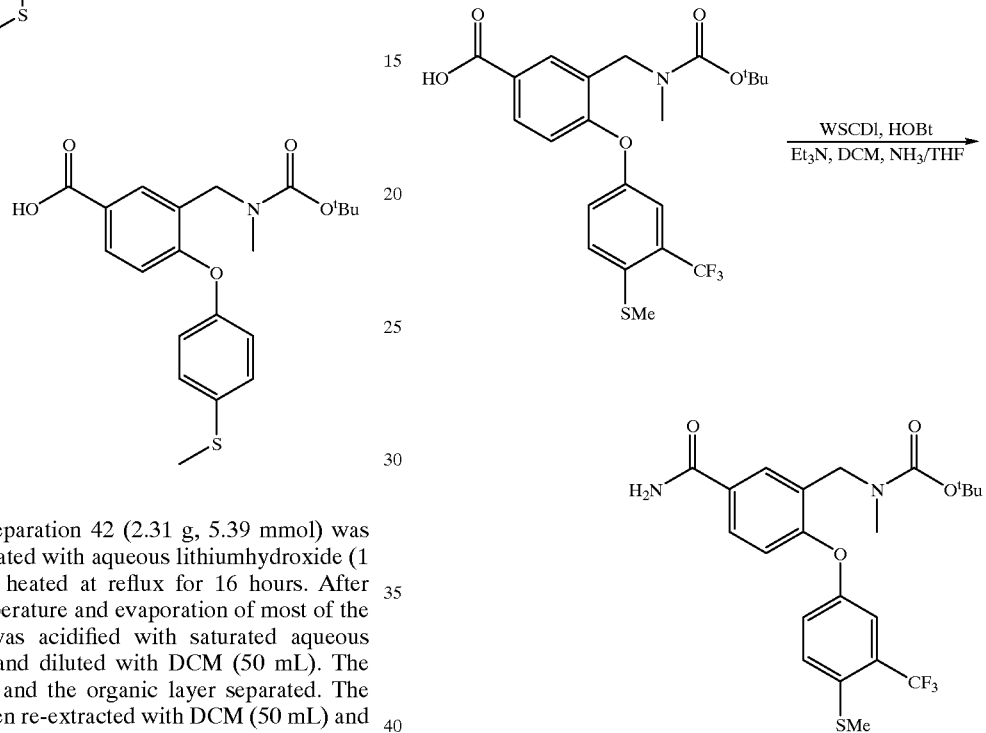

The ester from preparation 42 (2.31 g, 5.39 mmol) was dissolved in THF, treated with aqueous lithiumhydroxide (1 M) and the mixture heated at reflux for 16 hours. After cooling to room temperature and evaporation of most of the THF, the mixture was acidified with saturated aqueous ammonium choride and diluted with DCM (50 mL). The mixture was filtered and the organic layer separated. The aqueous layer was then re-extracted with DCM (50 mL) and the combined organic extracts dried (MgSO$_4$) and evaporated to white foam (ca. 2.3 g, ca. 100%) which was not purified further; $\delta_H$(CDCl$_3$, 300 MHz) 1.45 (9 H, s), 2.51 (3 H, s), 2.91 (3 H, brs), 4.55 (2 H, brd), 6.80 (1 H, d), 6.98 (2 H, d), 7.29 (2 H, d), 7.92 (1 H, d), 8.03 (1 H, brd); MS m/z (TS$^+$) 404 (MH$^+$)

PREPARATION 45

3-{[(tert-Butoxycarbonyl)(methyl)amino]methyl}-4-[3-methoxy-4-(methylsulfanyl)phenoxy]benzoic acid

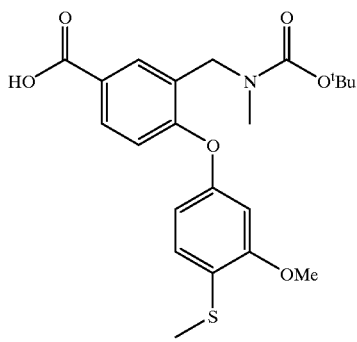

The title carboxylic acid was prepared from the ester of preparation 41 using the method described above for preparation 44. $\delta_H$(CDCl$_3$, 400 MHz) 1.43 (9 H, s), 2.39 (3 H, s), 2.87 (3 H, brs), 3.81 (3 H, s), 4.52 (2 H, brm), 6.54 (2 H, m), 6.79 (2 H, d), 7.13 (1 H, d), 7.90 (1 H, d), 8.00 (1 H, brm); MS m/z (ES$^+$) 432 (M-H$^+$)

PREPARATION 46 tert-Butyl 5-(aminocarbonyl)-2-[4-(methylsulfanyl)-3-(trifluoromethyl)phenoxy]-benzyl(methyl)carbamate The carboxylic acid from example 43 (388 mg, 0.82 mmol) was dissolved in DCM (10 mL) and treated with triethylamine (287 μL, 2.06 mmol), 1-hydroxybenzotriazole (139 mg, 1.03 mmol) and WSCDI (205 mg, 1.07 mmol). The solution was stirred at room temperature for 1 hour before the addition of saturated ammonia in THF (2 mL, excess), and then left to stir overnight. The mixture was acidified with hydrochloric acid (2 M; 5 mL) and the organic layer separated. The aqueous layer was re-extracted with DCM (10 mL with trace of methanol added) and the combined extracts were washed with brine (10 mL), dried (MgSO$_4$) and evaporated to a white solid (396 mg, 100%); $\delta_H$ (CD$_3$OD, 300 MHz) 1.41 (9 H, s), 2.54 (3 H, s), 2.90 (3 H, s), 4.58 (2 H, s), 6.95 (1 H, d), 7.21 (1 H, d), 7.30 (1 H, s), 7.60 (1 H, d), 7.83 (1 H, d), 7.91 (1 H, s); MS mlz (TS+) 488 (MNH$_4$).

PREPARATIONS 47–54

The series of amides below was prepared from the appropriate carboxylic acid using the method described in preparation 46.

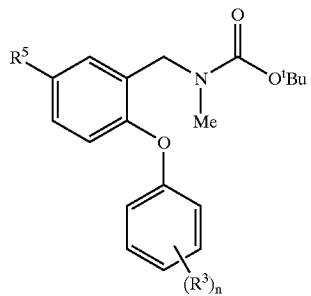

| Preparation | Starting Material | R⁵ | (R³)ₙ | data |
|---|---|---|---|---|
| 47 | Prep 44 | MeO~~~N(H)~~~C(=O)- (MeOCH₂CH₂NHC(O)-) | 4-SMe | $\delta_H$(CDCl₃, 300MHz)1.48(9H, s), 2.50(3H, s), 2.89(3H, s), 3.39(3H, s), 3.57(2H, m), 3.66(2H, m), 4.54(2H, brs), 6.45(1H, brs), 6.83(1H, d), 6.92(2H, d), 7.28(2H, d), 7.49 (1H, m), 7.72(1H, s); MSm/z(TS⁺)461 (MH⁺) |
| 48 | Prep 44 | HO-CH₂-CH(Me)-NHC(O)- (S) | 4-SMe | $\delta_H$(CDCl₃, 300MHz)1.40(9H, s), 2.45(3H, s), 2.84(3H, s), 3.53(2H, m), 3.76(2H, m), 4.46(2H, s), 6.74(1H, d), 6.87(2H, d), 7.23 (2H, d), 7.61(1H, d), 7.71(1H, s); MSm/z (TS⁺)447(MH⁺) |
| 49 | Prep 44 | H₂N-C(=O)-CH₂-NHC(O)- | 4-SMe | $\delta_H$(CDCl₃, 400MHz)1.22(2H, s), 1.42(9H, s), 2.45(3H, s), 2.86(3H brs), 4.10(2H, s), 4.51(2H, brs), 6.78(2H, d), 6.89(2H, d), 7.24(1H, m), 7.62(1H, d), 7.74(1H, s); MS m/z(TS⁺)378(MNH₄⁺) |
| 50 | Prep 44 | HO-CH₂-CH(Me)-NHC(O)- | 4-SMe | $\delta_H$(CDCl₃, 400MHz)1.25(3H, d), 1.43(9H, s), 2.46(3H, s), 2.85(3H, s), 3.61(1H, m), 3.84(1H, m), 4.23(1H, m), 4.50(2H, brs), 6.80(1H, m), 6.89(2H, d), 7.25(2H, d), 7.60 (1H, d), 7.68(1H, s); MSm/z(TS⁺)361(([M-Boc]H⁺) |
| 51 | Prep 44 | HO-CH₂-CH(Me)-NHC(O)- (R) | 4-SMe | $\delta_H$(CDCl₃, 400MHz)1.24(3H, d), 1.42(9H, s), 2.45(3H, s), 2.85(3H, s), 3.81(1H, m), 3.95(1H, m), 4.23(1H, brs), 4.49(2H, brs), 6.18(1H, brs), 6.79(1H, d), 6.88(2H, d), 7.24(2H, d), 7.60(1H, d), 7.67(1H, s); MS m/z(TS⁺)361([M-Boc]H⁺) |
| 52 | Prep 44 | MeNHC(O)- | 4-SMe | $\delta_H$(CDCl₃, 300MHz)1.44(9H, s), 2.46(3H, s), 2.87(3H, brs), 2.97(3H, d), 4.51(2H, s), 6.32(1H, brs), 6.79(1H, d), 6.90(2H, d), 7.27(2H, d), 7.46(1H, d), 7.70(1H, s); MS m/z(TS⁺)418(MH⁺) |
| 53 | Prep 45 | H₂NC(O)- | 3-OMe 4-SMe | $\delta_H$(CDCl₃, 400MHz)1.42(9H, brs), 239 (3H, s), 2.88(3H, brs), 3.82(3H, s), 4.51(2H, brs), 6.51(2H, m), 6.82(1H, d), 7.12(1H, d), 7.64(1H, dd), 7.71(1H, d); MSm/z(TS⁺)450 (MNH₄⁺) |
| 54 | Prep 45 | MeNHC(O)- | 3-OMe 4-SMe | $\delta_H$(CDCl₃, 400MHz)1.43(9H, brs), 2.39 (3H, s), 2.86(3H, brs), 2.97(3H, d), 3.80(3H, s), 4.50(2H, brs), 6.06(1H, brm), 6.46(2H, m), 6.82(1H, d), 7.12(1H, d), 7.60(1H, dd), 7.65(1H, d); MSm/z(TS⁺)464(MH₄⁺) |

PREPARATION 55

2-[4-(Methylsulfanyl)phenoxy]-5-nitrobenzonitrile

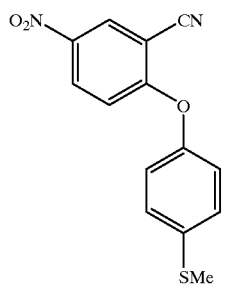

A mixture of 2-chloro-5-nitrobenzonitrile (3.75 g, 20.5 mmol), 4-(methylsulfanyl)phenol (3 g, 21.4 mmol) and potassium carbonate (3.4 g, 24.6 mmol) in DMF (50 mL) was heated at 100° C. for 2.5 h. After cooling to room temperature the solvent was removed in vacuo and the residue was partitioned between DCM (200 mL) and water (200 mL). The organic layer was washed with water (100 mL), dried (MgSO$_4$) and evaporated to give the product contaminated with traces of 4-(methylsulfanyl)phenol and DMF (6.08 g, quantitative yield); $\delta_H$(CDCl$_3$, 400 MHz) 2.53 (3 H, s), 6.90 (1 H, d), 7.08 (2 H, d), 7.36 (2 H, d), 8.30 (1 H, dd), 8.57 (1 H, d); MS m/z (TS$^+$) 304 (MNH$_4^+$).

PREPARATIONS 56–58

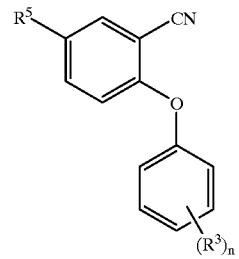

The diphenylethers below were prepared in an analogous fashion to that in preparation 55 from the appropriate ortho-chlorobenzonitrile (commercially available) and phenol components as indicated.

| Preparation | Starting Material | R$^5$ | (R$^3$)$_n$ | data |
|---|---|---|---|---|
| 56 | Prep 35 | NO$_2$ | 3-OMe, 4-SMe | $\delta_H$(CDCl$_3$, 400MHz) 2.40(3H, s), 3.85 (3H, s), 6.60(1H, d), 6.70(1H, d), 6.88(1H, d), 7.17(1H, d), 8.26(1H, d), 8.50(1H, s); MSm/z(TS$^+$)334(MNH$_4^+$) |
| 57 | Prep 34 | NO$_2$ | 3-CF$_3$, 4-SMe | $\delta_H$(CDCl$_3$, 400MHz) 2.58(3H, s), 6.90(1H, d), 7.30(1H, dd), 7.49(2H, m), 8.37(1H, dd), 8.60(1H, d); MSm/z(TS$^+$)372(MNH$_4^+$) |
| 58 | — | Cl | 4-SMe | Material used crude MSm/z(TS$^+$)293(MH$^+$). |

PREPARATION 59

5-Amino-2-[4-(methylsulfanyl)phenoxy]benzonitrile

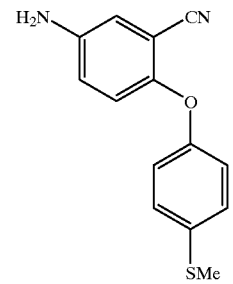

Iron powder (8.0 g, 143 mmol) was added portionwise over 10 min to a suspension of the nitrile of preparation 55 (20.5 mmol) in acetic acid (100 mL) and water (15 mL) and the resulting mixture was stirred at room temperature for 2 h. The solvent was removed in vacuo and the residue was partitioned between DCM (250 mL) and aqueous potassium carbonate (10%; 300 mL). The aqueous layer was extracted with DCM (100 mL) and the combined organic layers were dried (MgSO$_4$) and evaporated to give a pale brown solid (5.01 g, 95%); $\delta_H$(CDCl$_3$, 400 MHz) 2.47 (3 H, s), 3.71 (2 H, br), 6.81 (2 H, s), 6.92 (3 H, m), 7.25 (2 H, m); MS m/z (TS$^+$) 274 (MNH$_4^+$).

PREPARATIONS 60–61

The anilines below were prepared in an analogous fashion to that in preparation 59 from the appropriate nitro compound.

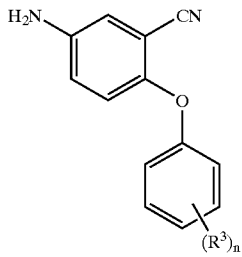

| Preparation | Starting Material | $(R^3)_n$ | data |
|---|---|---|---|
| 60 | Prep 56 | 3-OMe 4-SMe | $\delta_H$(CDCl$_3$, 400MHz)2.49(3H, s), 3.91(2H, brs), 6.88 (2H, s), 6.92(1H, d), 7.19(1H, d), 7.23(1H, d), 7.40(1H, d); MSm/z(TS$^+$)342(MNH$_4^+$) |
| 61 | Prep 57 | 3-CF$_3$ 4-SMe | $\delta_H$(CDCl$_3$, 400MHz)2.49(3H, s), 3.91(2H, brs), 6.88 (2H, s), 6.92(1H, d), 7.19(1H, d), 7.23(1H, d), 7.40(1H, d); MSm/z(TS$^+$)342(MNH$_4^+$) |

PREPARATION 62

N-{3-Cyano-4-[4-(methylsulfanyl)phenoxy]phenyl}methanesulfonamide

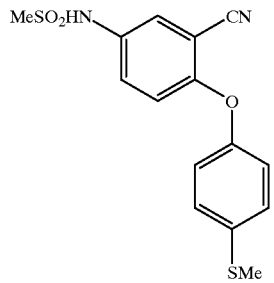

Methanesulfonyl chloride (3 mL, 38.8 mmol) was added to a solution of the nitrile of preparation 59 (5 g, 19.5 mmol) and triethylamine (5.6 mmol) in DCM (50 mL) and the mixture was stirred at room temperature for 2 h. The solvent was removed in vacuo and the residue was partitioned between DCM (50 mL) and hydrochloric acid (2 M; 50 mL). The aqueous layer was extracted with DCM (50 mL) and the combined organic extracts were concentrated in vacuo. The residue was taken up in THF (15 mL), sodium hydroxide (2 M; 50 mL) was added and the mixture was stirred for 3 h. The reaction was acidified with hydrochloric acid (2 M; 55 mL) and extracted with DCM (2×100 mL), the combined organic extracts being dried (MgSO$_4$) and evaporated to give a pale yellow crystalline solid (6.45 g, 99%); $\delta_H$(CDCl$_3$, 400 MHz) 2.50 (3 H, s), 3.03 (3 H, s), 6.47 (1 H, br), 6.86 (1 H, d), 7.02 (2 H, d), 7.32 (2 H, d), 7.37 (1 H, dd), 7.54 (1 H, d); MS m/z (ES$^+$) 357 (MNa$^+$).

PREPARATIONS 63–64

The methane sulfonamides below were prepared from the requisite aniline by the method described in preparation 62.

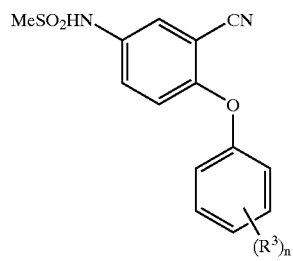

| Preparation | Starting Material | $(R^3)_n$ | data |
|---|---|---|---|
| 63 | Prep 60 | 3-OMe 4-SMe | $\delta_H$(CDCl$_3$, 400MHz)2.47(3H, s), 3.06(3H, s), 3.90(3H, s), 6.66(2H, m), 6.90(1H, d), 7.20(1H, d), 7.40(1H, dd), 7.55(1H, d) |

-continued

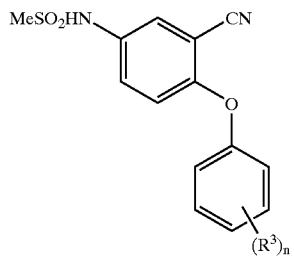

| Preparation | Starting Material | (R³)ₙ | data |
|---|---|---|---|
| 64 | Prep 61 | 3-CF₃ 4-SMe | δ_H(CDCl₃, 400MHz)2.52(3H, s), 3.08(3H, s), 6.89(1H, d), 7.21(1H, d), 7.32–7.47(3H, m), 7.58(1H, s) |

PREPARATION 65

N-{3-Cyano-4-[4-(methylsulfanyl)phenoxy]phenyl}-N-methylmethanesulfonamide

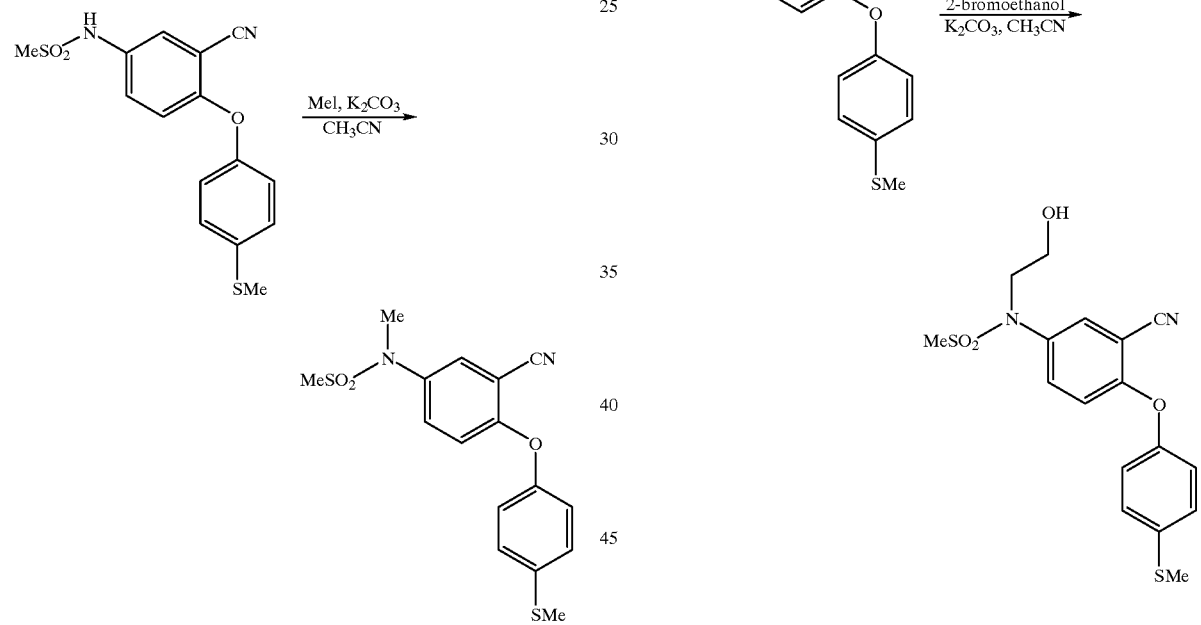

Methyl iodide (2.5 mL, 40.2 mmol) and potassium carbonate (1.25 g, 9.04 mmol) were added to a solution of the sulfonamide of preparation 62 (2.7 g, 8.07 mmol) in acetonitrile (40 mL) and the mixture was stirred at room temperature for 68 h. The reaction mixture was poured into sodium hydroxide (2 M; 50 mL) and extracted with ethyl acetate (50 mL). The organic layer was washed with brine, dried (MgSO₄) and evaporated to give the title compound (2.75 g, 98%); δ_H(CDCl₃, 300 MHz) 2.50 (3 H, s), 2.87 (3 H, s), 3.30 (3 H, s), 6.82 (1 H, d), 7.03 (2 H, d), 7.32 (2 H, d), 7.49 (1 H, dd), 7.62 (1 H, d); MS m/z (TS⁺) 366 (MNH₄⁺).

PREPARATION 66

N-{3-cyano-4-[4-(methylsulfanyl)phenoxy]phenyl}-N-(2-hydroxyethyl)methane-sulfonamide 2-Bromoethanol (2.5 mL, 35.3 mmol) and potassium carbonate (4.9 g, 35.5 mmol) were added to a solution of the sulfonamide of preparation 62 (2.7 g, 8.07 mmol) in acetonitrile (40 mL) and the mixture was stirred at room temperature for 68 h. TLC analysis indicated starting material remaining so the mixture was then heated at reflux for 20 hrs. After cooling, the reaction mixture was poured into sodiumhydroxide (2 M; 50 mL) and extracted with ethyl acetate (50 mL). The organic layer was washed with brine, dried (MgSO₄) and evaporated. Purification of the residue by multiple column chromatography (SiO₂) gave the title compound (1.90 g, 62%); δ_H(CDCl₃, 300 MHz) 2.50 (3 H, s), 3.00 (3 H, s), 3.77 (2 H, m), 3.80 (2 H, m), 6.83 (1 H, d), 7.04 (2 H, d), 7.33 (2 H, d), 7.50 (1 H, dd), 7.67 (1 H, d); MS m/z (TS⁺) 396 (MNH₄⁺).

PREPARATION 67

5-(Aminosulfonyl)-2-fluoro-N-methylbenzamide

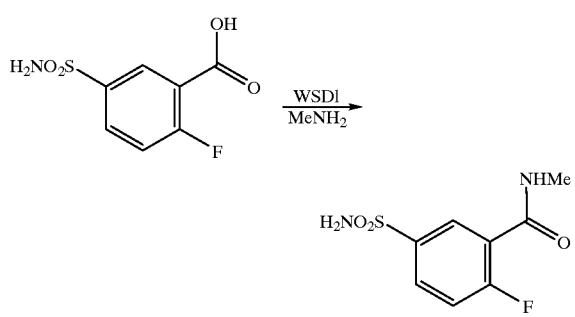

To a suspension of 5-(aminosulfonyl)-2-fluorobenzoic acid [prepared according to Chem. Pharm. Bull. 1995, 43(4), 582–7] (3.0g, 13.7mmol) in dichloromethane (100 mL) at room temperature under nitrogen was added 1-(3-dimethylaminopropyl)-3-ethylcarbodiimide hydrochloride (WSCDI) (2.89 g, 15.06 mmol) followed by a solution of methylamine in tetrahydrofuran (2 M, 8.21 mL, 16.42 mmol), dropwise and the reaction allowed to stir for 16 hours. The crude reaction mixture was then evaporated to dryness and the residue chromatographed on silica gel, eluting with dichloromethane:methanol:ammonia (84:14:2) as solvent to give the amide (732mg, 23%) as a white powder. $^1$H NMR (300 MHz, d$_4$-MeOH): δ=2.97 (3 H, s), 7.40 (1 H, t), 8.05 (1 H, m), 8.29 (1 H, d). MS m/z 250 (MNH$_4$)$^+$

PREPARATION 68

N'-(3-{3-[(Dimethylamino)methyl]-4-[4-(methylsulfanyl)phenoxy]phenyl}propanoyl)-4-methylbenzenesulfonohydrazide

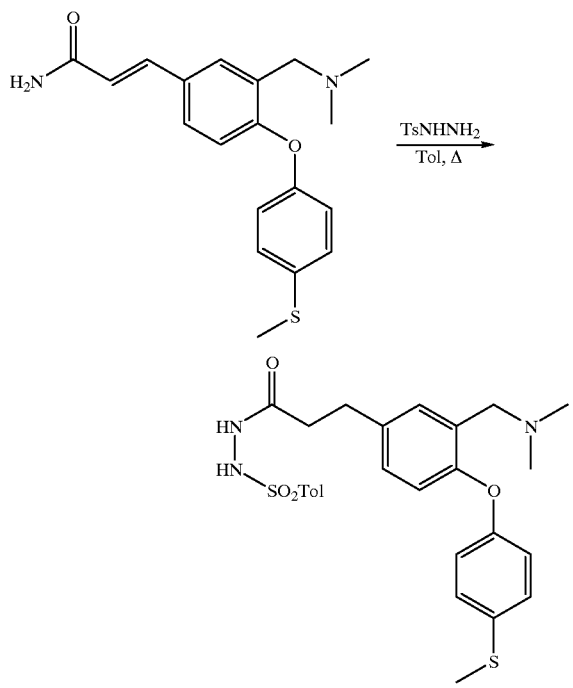

Treating the unsaturated amide formed in example 68 to the reduction conditions used for example 71 afforded the title compound; Free base: δ$_H$(CDCI$_3$, 400 MHz) 2.28 (6 H, s), 2.36 (2 H, t), 2.41 (3 H, s), 2.46 (3 H, s), 2.48–2.67 (2 H, brm), 2.77 (2 H, t), 3.48 (2 H, s), 6.74 (1 H, d), 6.84 (2 H, d), 6.91 (1 H, dd), 7.23–7.30 (5 H, m), 7.75 (2 H, d); MS m/z (TS$^+$) 514,516 (MH$^+$)

PREPARATION 69

N'-(3-{4-[(Dimethylamino)methyl]-3-[4-(methylsulfanyl)phenoxy]phenyl}propanoy)4-methylbenzenesulfonohydrazide

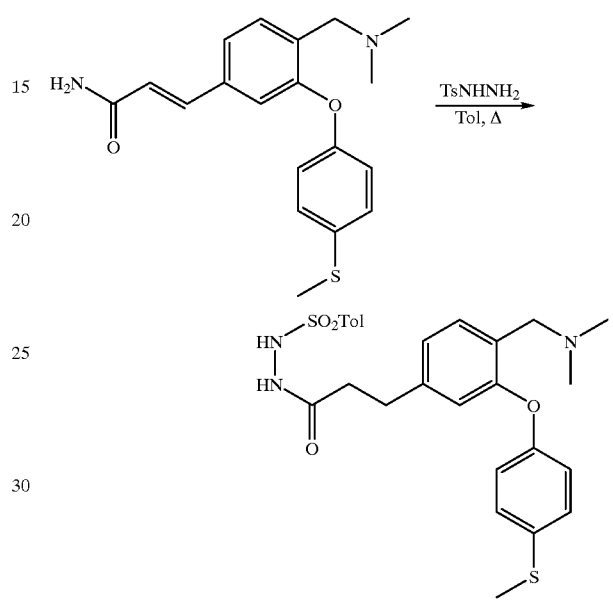

Treating the unsaturated amide formed in example 69 to the reduction conditions used for example 71 afforded the title compound; Free base: δ$_H$(CDCI$_3$, 300 MHz) 2.23 (2 H, t), 2.38 (3 H, s), 2.48 (3 H, s), 2.62 (2 H, t), 4.27 (2 H, s), 6.68 (1 H, s), 6.97 (1 H. d), 7.04 (2 H, d), 7.30–7.34 (4 H, m), 7.58 (1 H, d), 7.62 (1 H, d), 9.64 (1 H, s), 9.91 (1 H, s), 10.34 (1 H, brs); MS m/z (ES$^+$) 514 (MH$^+$)

Biological Activity

A number of compounds were tested for biological activity by their ability to inhibit the uptake of serotonin by human serotonin transporters as follows.

(i) Cell Culture

Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C and 5% CO$_2$ in DMEM-culture media (supplemented with 10% dialysed foetal calf serum (FCS), 2 mM 1-glutamine and 250 μg/ml geneticin)). Cells were harvested for the assay to yield a cell suspension of 750,000 cells/ml.

(i) Determination of inhibitor potency

All test compounds were dissolved in 100% DMSO and diluted down in assay buffer to give appropriate test concentrations. Assays were carried out in 96-well filter bottom plates. Cells (7500 cells/assay well) were pre-incubated in standard assay buffer containing either test compound, standard inhibitor or compound vehicle (1 % DMSO) for 5 minutes. Reactions were started by addition of either ³H-Serotonin, ³H-Noradrenaline or ³H-Dopamine substrates. All reactions were carried out at room temperature in a shaking incubator. Incubation times were 5 minutes for the hSERT and hDAT assays and 15 minutes for the hNET assay. Reactions were terminated by removal of the reaction mixture using a vacuum manifold followed by rapid washing with ice cold assay buffer. The quantity of ³H-substrate incorporated into the cells was then quantified.

Assay plates were dried in a microwave oven, scintillation fluid added, and radioactivity measured. Potency of test compounds was quantified as $IC_{50}$ values (concentration of test compound required to inhibit the specific uptake of radiolabelled substrate into the cells by 50%).

(iii) Standard Assay Buffer Composition:
Trizma hydrochloride (26 mM)
NaCl (124 mM)
KCl (4.5 mM)
$KH_2PO_4$ (1.2 mM)
$MgCl_2.6H_2$) (1.3 mM)
Ascorbic acid (1.136 mM)
Glucose (5.55 mM)
pH 7.40
$CaCl_2$ (2.8 mM)
Pargyline (100 μM)
Note: The pH of the buffer was adjusted to 7.40 with 1 M NaOH before addition of $CaCl_2$ and pargyline.

(iv) Summary of Assay Parameters

|  | hSERT Assay | hDAT Assay | hNET Assay |
|---|---|---|---|
| Cell concentration per assay well. | 75,000 | 75,000 | 75,000 |
| Substrate Concentration. | ³H-5HT (50 nM) | ³H-Dopamine (200 nM) | ³H-Noradrenaline (200 nM) |
| Incubation time (minutes) | 5 | 5 | 15 |

Compounds having a serotonin re-uptake inhibition (SRI) $IC_{50}$ value of less than or equal to 100nM are the title compounds of Examples 1–4, 6, 9–12, 14, 23, 25, 28–33, 35–53, 55–62, 64, 65, 71–80, 84, 85, 87, 90–92, 94–99, 101–106, 110, 112, 114–122, 125, 128–142, 145–149 and 154–191.

Compounds having an serotonin re-uptake inhibition (SRI) $IC_{50}$ value of less than or equal to 100 nM and which are more than 10-fold as potent in the inhibition of serotonin re-uptake than in the inhibition of dopamine re-uptake or noradrenaline re-uptake are the title compounds of Examples 3, 4, 6, 9–12, 14, 23, 25, 28–33, 35–40, 45–53, 55, 56, 58, 62, 64, 65, 71, 73–76, 84, 85, 87, 90–92, 94–98, 101–104, 106, 110, 112, 114–122, 128–131, 134–141, 145–148, 155–159, 161, 162,165, 167–179 and 181–191.

Compounds having an serotonin re-uptake inhibition (SRI) $IC_{50}$ value of less than or equal to 100 nM and which are more than 100-fold as potent in the inhibition of serotonin re-uptake than in the inhibition of dopamine re-uptake or noradrenaline re-uptake are the title compounds of Examples 3, 4, 6, 9–12, 14, 23, 25, 28–32, 35–40, 46–51, 53, 55, 58, 62, 64, 71, 73–76, 84, 85, 87, 90, 91, 94–98, 101–104, 106, 110, 112, 114, 116–118, 120, 121, 128–131, 135,137,139–141, 145–148,155–159, 161, 162,169–179 and 181–190.

Compounds having an serotonin re-uptake inhibition (SRI) $IC_{50}$ value of less than or equal to 100 nM and which are more than 100-fold as potent in the inhibition of serotonin re-uptake than in the inhibition of dopamine re-uptake and noradrenaline re-uptake are the title compounds of Examples 3, 4, 9, 14, 23, 25, 28–30, 35, 36, 38–40, 46, 53, 58, 74, 84, 85, 87, 90, 91, 94–98, 101, 104, 110, 114, 116, 117, 120, 121, 128, 130, 135, 140, 141, 145–148, 156, 157, 169, 170, 174–176, 181–185 and 187–190.

Compounds having an serotonin re-uptake inhibition (SRI) $IC_{50}$ value of less than or equal to 50 nM and which are more than 100-fold as potent in the inhibition of serotonin re-uptake than in the inhibition of dopamine re-uptake and noradrenaline re-uptake are the title compounds of Examples 3, 4, 9, 14, 23, 25, 28, 30, 36, 38–40, 46, 53, 58, 74, 84, 85, 87, 90, 91, 94–98, 101, 104, 110, 114, 116, 117, 120, 121, 128, 130, 135, 140, 141, 145, 147, 148, 156, 157, 169, 170, 174–176, 181–185 and 187–190.

What is claimed is:

1. A compound of general formula (I), or a pharmaceutically acceptable salt thereof:

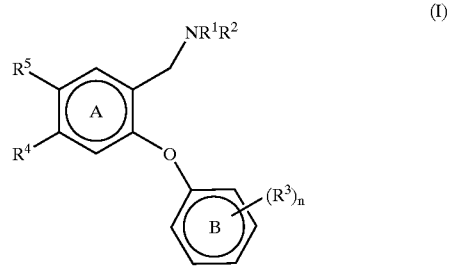

wherein;
$R^1$ and $R^2$, which may be the same or different, are hydrogen, $C_1$–$C_6$alkyl, $(CH_2)m(C_3$–$C_6$-cycloalkyl) wherein m=0 1, 2 or 3, or $R^1$ and $R^2$ together with the nitrogen to which they are attached form an azetidine ring;

each $R^3$ is independently $CF_3$, $OCF_3$, $C_{1-4}$alkylthio or $C_1$–$C_4$alkoxy;

n is1,2 or 3; and $R^4$ and $R^5$, which may be the same or different, are:

A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$ alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F, OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and 0, optionally substituted independently by one or more $R^{13}$;

wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)$_2$;

wherein when $R^1$ and $R^2$ are methyl, $R^4$ and $R^5$ are hydrogen, and n is 1, $R^3$ is not a —SMe group para to the ether linkage linking rings A and B.

2. A compound according to claim 1, or a pharmaceutically acceptable salt thereof, wherein $R^1$ and $R^2$ which may be the same or different, are hydrogen or $C_1$–$C_6$alkyl.

3. A compound according to claim 1 or a pharmaceutically acceptable salt thereof, wherein each $R^3$ is independently —$CF_3$, —$OCF_3$, methylthio, ethylthio or methoxy.

4. A compound according to claim 1, or a pharmaceutically acceptable salt thereof, wherein at least one $R^3$ is para to the ether linkage linking ring A and B.

5. A compound according to claim 1, or a pharmaceutically acceptable salt thereof, wherein at least one $R^3$ is methylthio.

6. A compound according to claim 1, or a pharmaceutically acceptable salt thereof, wherein $R^6$ and $R^7$, which may be the same or different, are hydrogen, $C_1$–$C_3$alkyl optionally substituted by hydroxy, —$CONH_2$ or $C_1$–$C_3$alkoxy.

7. A compound according to claim 1, or a pharmaceutically acceptable salt thereof, wherein $R^8$ is hydrogen, hydroxyethyl or methyl.

8. A compound according to claim 1, or a pharmaceutically acceptable salt thereof, wherein $R^9$ is methyl, ethyl, isopropyl, trifluoromethyl or methoxyethyl.

9. A compound according to claim 1, or a pharmaceutically acceptable salt thereof, wherein p is 1 or 0.

10. A compound according to claim 1, or a pharmaceutically acceptable salt thereof,
wherein $R^4$ and $R^5$, which may be the same or different, are
—$(CH_2)_p$—X, where p is 0, 1 or 2; X is hydrogen, hydroxy, $CONR^6R^7$, $SO_2NR^6R^7$, $NR^8SO_2R^9$, $SR^{10}$, $SOR^9$ or $SO_2R^{10}$; or a 5- or 6-membered heterocyclic ring containing 1, 2 or 3 heteroatoms selected from N, S and O.

11. A compound according claims 1, or a pharmaceutically acceptable salt thereof,
wherein $R^4$ and $R^5$, which may be the same or different, are: —$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen or $C_1$–$C_3$alkyl optionally substituted by hydroxy, —$CONH_2$ or $C_1$–$C_3$alkoxy; $R^8$ is hydrogen, hydroxyethyl or methyl; or $R^9$ is methyl, ethyl, isopropyl, trifluoromethyl or methoxyethyl; or triazolyl, imidazolyl or pyrazolyl.

12. A compound according to claim 1, or a pharmaceutically acceptable salt thereof, wherein $R^4$ and $R^5$ are not both hydrogen.

13. A compound according to claim 1, or a pharmaceutically acceptable salt thereof, wherein $R^4$ is hydrogen.

14. A compound according to claim 1, or a pharmaceutically acceptable salt thereof, selected from the group consisting of:

3-[(dimethylamino)methyl]-4-[4-(methylsulfanyl)phenoxy]benzene-sulfonamide;

3-[(dimethylamino)methyl]-N-methyl-4-[4-(trifluoromethyl)phenoxy]-benzenesulfonamide;

3-[(dimethylamino)methyl]-4-[4-(trifluoromethoxy)phenoxy]-benzenesulfonamide;

3-[(dimethylamino)methyl]-N-[(2 R)-2-hydroxypropyl]-4-[4-(methylsulfanyl)-phenoxy]benzenesulfonamide;

3-[(dimethylamino)methyl]-N-[(1 S)-2-hydroxy-1-methylethyl]-4-[4-(methylsulfanyl)phenoxy]benzenesulfonamide;

3-[(dimethylamino)methyl]-N-(2-hydroxyethyl)-4-[4-(methylsulfanyl)-phenoxy]benzenesulfonamide;

3-[(dimethylamino)methyl]-4-[4-(methylsulfanyl)phenoxy]benzonitrile;

3-[(dimethylamino)methyl]-4-[4-(methylsulfanyl)phenoxy]benzamide;

3-[(dimethylamino)methyl]-4-[4-(trifluoromethoxy)phenoxy]benzamide;

3-[(methylamino)methyl]-4-[4-(methylsulfanyl)phenoxy]benzamide;

N-{3-[(dimethylamino)methyl]-4-[4-(trifluoromethyl)phenoxy]phenyl}-methanesulfonamide;

4-[3-methoxy-4-(methylsulfanyl)phenoxy]-3-[(methylamino)methyl]-benzamide;

N-methyl-3-[(methylamino)methyl]-4-[4-(methylsulfanyl)phenoxy]-benzamide;

3-[(dimethylamino)methyl]-4-[3-methoxy-4-(methylsulfanyl)phenoxy]-benzamide;

N-methyl-N-[2-[4-(methylsulfanyl)phenoxy]-5-(1 H-1,2,3-triazol-1-yl)benzyl]-amine;

N-methyl-N-[2-[4-(methylsulfanyl)phenoxy]-5-(1 H-1,2,4-triazol-1-yl)benzyl]-amine;

N,N-dimethyl-N-[2-[4-(methylsulfanyl)phenoxy]-5-(1 H-1,2,4-triazol-1-yl)benzyl]-amine;

N-[2-[4-(methylsulfanyl)phenoxy]-5-(4 H-1,2,4-triazol-4-yl)benzyl]-N,N-dimethylamine; and N-{5-(3-amino-1 H-pyrazol-1-yl)-2-[4-(methylsulfanyl)phenoxy]benzyl}-N-methylamine.

15. A pharmaceutical formulation containing a compound according to claim 1, or a pharmaceutically acceptable salt thereof, and a pharmaceutically acceptable adjuvant, diluent or carrier.

16. A method of treatment or prevention of a disorder in which the regulation of monoamine transporter function is implicated, comprising the administration of an effective amount of a compound according to claim 1 or a pharmaceutically acceptable salt thereof, to a patient in need of such treatment or prevention.

17. A method of treatment or prevention of premature ejaculation, comprising the administration of an effective amount of a compound according to claim 1 or a pharmaceutically acceptable salt thereof, to a patient in need of such treatment or prevention.

18. A method of increasing ejaculatory latency which comprises the administration of an effective amount of a compound according to claim 1, or a pharmaceutically acceptable salt thereof, to a male desiring increased ejaculatory latency.

19. A method of claim 16, wherein the disorder is depression, attention deficit hyperactivity disorder, obsessive compulsive disorder, post-traumatic stress disorder, substance abuse disorders or sexual dysfunction.

20. A method according to claim 19, wherein said sexual dysfunction is premature ejaculation.

21. A process for the preparation of a compound of general formula (I);

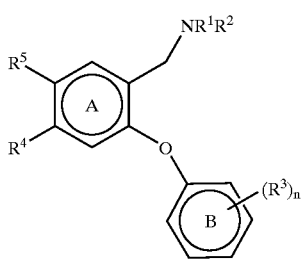
(I)

wherein $R^1$, $R^2$, $R^3$, $R^4$ and $R^5$ and n are as defined in claim 1 comprising reacting a compound of general formula II

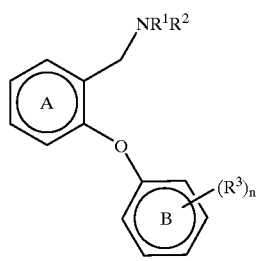
(II)

under suitable reaction conditions to form a compound of formula I, wherein the suitable reaction conditions are:

i) where $R^4/R^5$ are halogen, by reaction of (II) with a suitable halogenating agent in an inert solvent which does not adversely affect the reaction;

ii) where $R^4/R^5$ are —$NO_2$, by reaction of (II) with a suitable nitrating agent in an inert solvent which does not adversely affect the reaction at, or below, room temperature; or ii) where $R^4/R^5$ is —$SO_2NR^6R^7$ by reaction of an intermediate sulfonyl chloride with the requisite amine of formula $HNR^6R^7$ in a suitable solvent.

22. A process according to claim 21 for preparing compounds of formula Ia, i.e compounds of formula I where $R^5$ is —$SO_2NR^6R^7$;

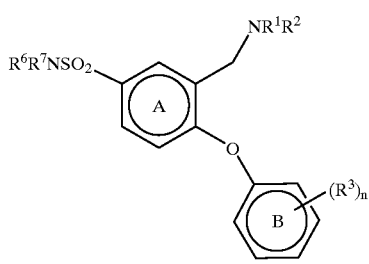
(Ia)

comprising a) reacting compounds of formula II, optioanlly in a suitable solvent, with chlorosulfonic acid to give compounds of formula (XII);

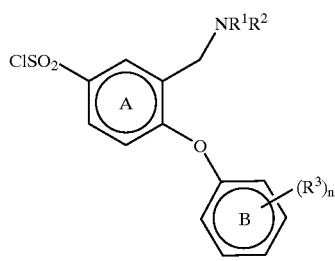
(XII)

followed by, b) reaction with $HNR^6R^7$ to give compounds of formula (Ia).

23. A process according to claim 22 wherein compounds of formula (XII) are generated in situ and reacted with $HNR^6R^7$ without isolation.

24. A process according to claim 21 which further comprises the step of preparing compounds of formula (II), by reacting compounds of formula (III)

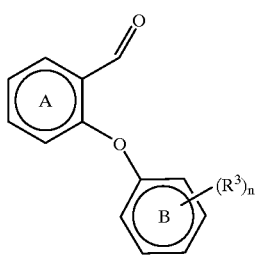
(III)

with a compound of formula $HNR^1R^2$, or with a suitable salt form thereof, together with a hydride reducing agent in a suitable solvent, to form a compound of formula (II).

25. A compound of formula (II) according to claim 21 with the proviso that in compounds of formula (II) when $R^1$ and $R^2$ are methyl, and n is 1, $R^3$is not a —SMe group para to the ether linkage linking rings A and B.

26. A compound of formula (I), or a pharmaceutically acceptable salt, solvates or polymorphs thereof, wherein $R^1$, $R^2$, $R^3$ and n are as defined in claim 1; and $R^4$ and $R^5$, which may be the same or different, are —$(CH_2)_p$—A', wherein p is 0, 1 or 2 and A' is a polar group.

27. A compound according to claim 26, wherein the polar group has a δ-value more negative than −0.1.

28. A compound of general formula (I) according to claim 1

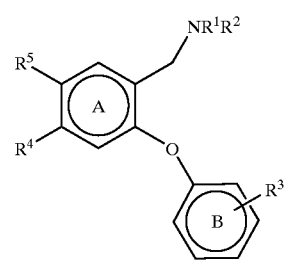
(I)

and pharmaceutically acceptable salts or solvates thereof wherein:

m=0, 1, 2 or 3, or wherein $NR^1R^2$ together represent a 4-membered ring wherein $R^1$ and $R^2$ together represent $C_3$ alkyl;

$R^3$ represents one or more groups selected from the group including. $CF_3$, $OCF_3$, $SR^{12}$ and $C_1$–$C_4$ alkoxy wherein $R^{12}$ represents $C_1$–$C_6$ alkyl; and $R^4$ and $R^5$ independently represent A—X wherein A=—$(CH_2)_n$—, wherein n represents 0, 1 or 2 and wherein X represents: H, F, Cl, Br, 1, $CONR^6R^7$ or $SO_2NR^6R^7$, OH, $NR^8SO_2R^9$, $NO_2$, $NR^6R^{11}$, CN, $CO_2R^{10}$, CHO, $S(O)_mR^{10}$ wherein m=0, 1 or 2 and wherein $R^6$, $R^7$, $R^8$ and $R^{10}$ independently represent H or $C_{1-6}$ alkyl, wherein $R^9$ represents $C_{1-6}$ alkyl, $R^{11}$ represents H, $C_{1-6}$ alkyl, $C(O)R^6$, $CO_2R^9$, $C(O)NHR^6$ or $SO_2NR^6R^6$ and wherein said $C_{1-6}$ alkyl group is optionally substituted by one or more groups selected from OH, $CO_2H$, $C_{3-6}$ cycloalkyl, $NH_2$, $CONH_2$, $C_{1-6}$ alkoxy, C16 alkoxycarbonyl and a 5- or 6-membered heterocyclic ring containing 1, 2 or 3 heteroatoms selected from N, S and O;

or $R^4$ and/or $R^5$ may be representative of a 5- or 6-membered heterocyclic ring containing 1, 2 or 3 heteroatoms selected from N, S and O; and in addition, $R^6$ and $R^7$ may, together with the N atom to which they are attached, represent a pyrrolidine or piperidine ring (which rings are optionally substituted by OH or $CONH_2$) or a morpholine ring (which is optionally substituted by $CONH_2$) with the with the proviso that both $R^4$ and $R^5$ are not H.

\* \* \* \* \*